(12) United States Patent
Iqbal et al.

(10) Patent No.: US 7,348,334 B2
(45) Date of Patent: Mar. 25, 2008

(54) MONOCYCLIC DERIVATIVES OF ARYL ALKANOIC ACIDS AND THEIR USE IN MEDICINE: PROCESS FOR THEIR PREPARATION AND PHARMACEUTICAL COMPOSITIONS CONTAINING THEM

(75) Inventors: Javed Iqbal, Hyderabad (IN); Gurram Ranga Madhavan, Hyderabad (IN); Saibal Kumar Das, Hyderabad (IN); Debnath Bhunia, Hyderabad (IN); Ranjan Chakrabarti, Hyderabad (IN); Ramanujam Rajagopalan, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 891 days.

(21) Appl. No.: 10/119,300

(22) Filed: Apr. 8, 2002

(65) Prior Publication Data
US 2003/0013729 A1 Jan. 16, 2003

(30) Foreign Application Priority Data
Apr. 9, 2001 (IN) .................. 301/MAS/2001

(51) Int. Cl.
*A61K 31/506* (2006.01)
*C07D 239/22* (2006.01)
(52) U.S. Cl. .................. 514/269; 544/314; 544/327
(58) Field of Classification Search ............ 514/269; 544/314, 327
See application file for complete search history.

(56) References Cited

U.S. PATENT DOCUMENTS 5,518,994 A * 5/1996 Kawamura et al. ......... 504/242
5,885,997 A * 3/1999 Lohray et al. .............. 514/256

* cited by examiner

*Primary Examiner*—James O. Wilson
*Assistant Examiner*—Tamthom N Truong
(74) *Attorney, Agent, or Firm*—Robert Steve Thomas

(57) ABSTRACT

The present invention relates to novel hypolipidemic, antihyperglycemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

(I)

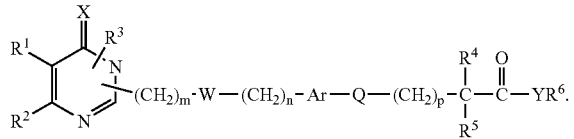

15 Claims, No Drawings

MONOCYCLIC DERIVATIVES OF ARYL ALKANOIC ACIDS AND THEIR USE IN MEDICINE: PROCESS FOR THEIR PREPARATION AND PHARMACEUTICAL COMPOSITIONS CONTAINING THEM

FIELD OF THE INVENTION

The present invention relates to novel hypolipidemic, antihyperglycemic compounds, their derivatives, their analogs, their tautomeric forms, their stereoisomers, their polymorphs, their pharmaceutically acceptable salts, their pharmaceutically acceptable solvates and pharmaceutically acceptable compositions containing them. More particularly, the present invention relates to novel β-aryl-α-oxysubstituted alkylcarboxylic acids of the general formula (I), their derivatives, their analogs, their tautomeric forms, their stereoisomers, their polymorphs, their pharmaceutically acceptable salts, their pharmaceutically acceptable solvates and pharmaceutically acceptable compositions containing them.

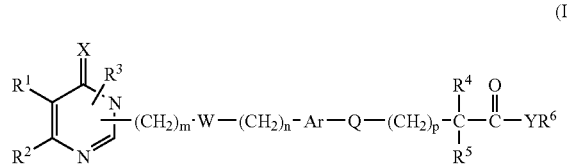

(I)

The present invention also relates to a process for the preparation of the above said novel compounds, their derivatives, their analogs, their tautomeric forms, their stereoisomers, their polymorphs, their pharmaceutically acceptable salts, pharmaceutically acceptable solvates, novel intermediates and pharmaceutical compositions containing them.

The compounds of this invention can be used to treat and/or prevent diabetes caused by insulin resistance or impaired glucose tolerance and to treat and prevent complications of diabetes caused by insulin resistance or impaired glucose tolerance. Complications of diabetes include but are not limited to dyslipidemia, stroke, hyperlipidemia, hypercholesteremia, hyperglycemia, atherosclerosis, leptin resistance, hypertension, obesity, insulin resistance, atherosclerosis, coronary artery disease and other cardiovascular disorders; renal disease, glomerulonephritis, glomerulosclerosis, nephrotic syndrome, hypertensive nephrosclerosis, nephropathy; retinopathy, disorders to related endothelial cell activation, psoriasis, polycystic ovarian syndrome (PCOS), dementia, inflammatory bowel diseases, myotonic dystrophy, pancreatitis, arteriosclerosis, xanthoma, eating disorders, cancer or osteoporosis. The compounds can be used as aldose reductase inhibitors or as an anti-inflammatory agents.

The compounds can be used to treat and/or prevent hyperlipidemia, hypercholesteremia, hyperglycemia, osteoporosis, obesity, impaired glucose tolerance, atherosclerosis, leptin resistance, insulin resistance or diseases in which insulin resistance is the underlying pathophysiological mechanism.

The compounds can be used for the treatment and/or prophylaxis of disorders related to Syndrome X such as hypertension, obesity, insulin resistance, atherosclerosis, coronary artery disease or a cardiovascular disorder.

The compounds can be used for reducing total cholesterol, body weight, blood plasma glucose, insulin, $HbA_{1C}$, triglycerides, LDL, VLDL or free fatty acids or increasing HDL in the plasma. The lowering of total cholesterol (TC), increasing high density lipoprotein (HDL) and decreasing low density lipoprotein (LDL), which have a beneficial effect on coronary heart disease and atherosclerosis.

The compounds of general formula (I) are useful in reducing body weight and for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL (very low density lipoprotein) and LDL. The compounds of the present invention can be used for the treatment of certain renal diseases including glomerulonephritis, glomerulosclerosis, nephrotic syndrome, hypertensive nephrosclerosis and nephropathy. The compounds of general formula (I) are also useful for the treatment and/or prophylaxis of insulin resistance (type II diabetes), leptin resistance, impaired glucose tolerance, dyslipidemia, disorders related to syndrome X such as hypertension, obesity, insulin resistance, coronary heart disease and other cardiovascular disorders. These compounds may also be useful as aldose reductase inhibitors, for improving cognitive functions in dementia, treating diabetic complications, disorders related to endothelial cell activation, psoriasis, polycystic ovarian syndrome (PCOS), inflammatory bowel diseases, osteoporosis, myotonic dystrophy, pancreatitis, arteriosclerosis, retinopathy, xanthoma, inflammation and for the treatment of cancer. The compounds of the present invention are useful in the treatment and/or prophylaxis of the above said diseases in combination/concomittant with one or more HMG CoA reductase inhibitors, hypolipidemic/ hypolipoproteinemic agents such as fibric acid derivatives, fibrates, ezetimibe, orlistat, nicotinic acid, cholestyramine, colestipol and probucol.

BACKGROUND OF INVENTION

Atherosclerosis and other peripheral vascular diseases effect the quality of life of millions of people. Therefore, considerable attention has been directed towards understanding the etiology of hypercholesterolemia and hyperlipidemia and the development of effective therapeutic strategies.

Hypercholesterolemia has been defined as plasma cholesterol level that exceeds arbitrarily defined value called "normal" level. Recently, it has been accepted that "ideal" plasma levels of cholesterol are much below the "normal" level of cholesterol in the general population and the risk of coronary artery disease (CAD) increases as cholesterol level rises above the "optimum" (or "ideal") value. There is clearly a definite cause and effect-relationship between hypercholesterolemia and CAD, particularly for individuals with multiple risk factors. Most of the cholesterol is present in the esterified forms with various lipoproteins such as low density lipoprotein (LDL), intermediate density lipoprotein (IDL), high density lipoprotein (HDL) and partially as very low density lipoprotein (VLDL). Studies clearly indicate that there is an inverse correlation between CAD and atherosclerosis with serum HDL-cholesterol concentrations. (Stampfer et al., *N. Engl. J. Med.,* 325 (1991), 373-381) and the risk of CAD increases with increasing levels of LDL and VLDL.

In CAD, generally "fatty streaks" in carotid, coronary and cerebral arteries, are found which are primarily free and esterified cholesterol. Miller et al., (*Br. Med. J,* 282 (1981), 1741-1744) have shown that increase in HDL-particles may decrease the number of sites of stenosis in coronary arteries of humans, and high level of HDL-cholesterol may protect against the progression of atherosclerosis. Picardo et al., (*Arteriosclerosis* 6 (1986) 434-441) have shown by in vitro experiments that HDL is capable of removing cholesterol from cells. They suggest that HDL may deplete tissues of excess free cholesterol and transfer them to the liver (Macikinnon et al., *J. Biol. Chem.* 261 (1986), 2548-2552). Therefore, agents that increase HDL cholesterol would have therapeutic significance for the treatment of hypercholesterolemia and coronary heart diseases (CHD).

Obesity is a disease highly prevalent in affluent societies and in the developing world and is a major cause of morbidity and mortality. It is a state of excess body fat accumulation. The causes of obesity are unclear. It is believed to be of genetic origin or promoted by an interaction between the genotype and environment. Irrespective of the cause, the result is fat deposition due to imbalance between the energy intake versus energy expenditure. Dieting, exercise and appetite suppression have been a part of obesity treatment. There is a need for efficient therapy to fight this disease since it may lead to coronary heart disease, diabetes, stroke, hyperlipidemia, gout, osteoarthritis, reduced fertility and many other psychological and social problems.

Diabetes and insulin resistance is yet another disease which severely effects the quality of life of a large population in the world. Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75:809-817; N. Engl. J. Med. (1987) 317:350-357; J. Clin. Endocrinol. Metab., (1988) 66: 580-583; J. Clin. Invest., (1975) 68:957-969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X.

Hyperlipidemia is the primary cause of cardiovascular (CVD) and other peripheral vascular diseases. High risk of CVD is related to the higher LDL (Low Density Lipoprotein) and VLDL (Very Low Density Lipoprotein) seen in hyperlipidemia. Patients having glucose intolerance/insulin resistance in addition to hyperlipidemia have higher risk of CVD. Numerous studies in the past have shown that lowering of plasma triglycerides and total cholesterol, in particular LDL and VLDL and increasing HDL cholesterol help in preventing cardiovascular diseases.

Peroxisome proliferator activated receptors (PPAR) are members of the nuclear receptor super family. The gamma (γ) isoform of PPAR(PPARγ) has been implicated in regulating differentiation of adipocytes (Endocrinology, (1994) 135: 798-800) and energy homeostasis (Cell, (1995) 83: 803-812), whereas the alpha (α) isoform of PPAR (PPARα) mediates fatty acid oxidation (Trend. Endocrin. Metab., (1993) 4: 291-296) thereby resulting in reduction of circulating free fatty acid in plasma (Current Biol. (1995) 5: 618-621). PPARα agonists have been found useful for the treatment of obesity (WO 97/36579). It has been recently disclosed that the hypolipidaemic effect is enhanced when the molecule has both PPARα and PPARγ agonist activity and suggested to be useful for the treatment of syndrome X (WO 97/25042). Synergism between the insulin sensitizer (PPARγ agonist) and HMG CoA reductase inhibitor has been observed which may be useful for the treatment of atherosclerosis and xanthoma. (EP 0 753 298).

It is known that PPARγ plays an important role in adipocyte differentiation (Cell, (1996) 87, 377-389). Ligand activation of PPAR is sufficient to cause complete terminal differentiation (Cell, (1994) 79, 1147-1156) including cell cycle withdrawal. PPARγ is consistently expressed in certain cells and activation of this nuclear receptor with PPARγ agonists would stimulate the terminal differentiation of adipocyte precursors and cause morphological and molecular changes characteristics of a more differentiated, less malignant state (Molecular Cell, (1998), 465-470; Carcinogenesis, (1998), 1949-53; Proc. Natl. Acad. Sci., (1997) 94, 237-241) and inhibition of expression of prostate cancer tissue (Cancer Research (1998), 58:3344-3352). This would be useful in the treatment of certain types of cancer, which express PPARγ and could lead to a quite nontoxic chemotherapy.

Leptin resistance is a condition wherein the target cells are unable to respond to leptin signals. This may give rise to obesity due to excess food intake and reduced energy expenditure and cause impaired glucose tolerance, type 2 diabetes, cardio-vascular diseases and such other interrelated complications. Kallen et al (Proc. Natl. Acad. Sci., (1996) 93, 5793-5796) have reported that insulin sensitizers which perhaps due to their PPAR agonist expression and lower plasma leptin concentrations. However, it has been recently disclosed that compounds having insulin sensitizing property also possess leptin sensitization activity. They lower the circulating plasma leptin concentrations by improving the target cell response to leptin (WO 98/02159).

A few aryloxy alkanoic acids, their derivatives, and their analogs have been reported to be useful in the treatment of hyperglycemia and hypercholesterolemia. Some of such compounds described in the prior art are outlined below:

i) International publication No. WO 00/49005 disclose the compounds of general formula (II a)

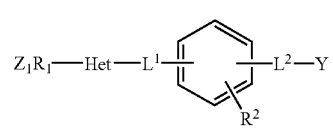

(IIa)

wherein Het is an optionally substituted, saturated partially saturated or fully unsaturated 8 to 10 membered bicyclic ring, $R^1$ is optionally substituted aryl or optionally substituted heteroaryl, $R^2$ is hydrogen halogen, lower alkyl or lower alkoxy, $L^1$ is an —$R^3$-$R^4$=linkage where $R^3$ is alkylene, alkenylene or alkynylene and $R^4$ is a direct bond, cycloalkylene, heterocycloalkylene, arylene, heteroarylidiyl, —C(=$Z^2$)-$NR^5$, $NR^5$—C(=$Z^2$), -$Z^2$-, —C(=O), —C(=$NOR^5$)—, —$NR^5$—, $N^5$—C(=$Z^2$)-$NR^5$, $SO_2$—$NR^5$ $NR^5$—$SO_2$, —O—C(=O)—, —C(=O)—O, —O—C (=O)—$NR^5$, —$NR^5$—C(=O)—O—; $L^2$ is optionally substituted alkylene or alkenylene, Y is carboxy or an acid bioisostere and $Z^1$ is $NR^5$ and the corresponding N-oxides and their prodrugs and pharmaceutically acceptable salts and solvates.

An example of these compounds is shown in formula (IIb)

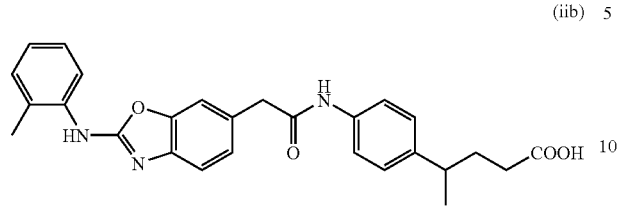

(iib)

ii) International publication No. WO 98/31359 disclose the compounds of general formula (IIc)

X—Y-Z-Aryl-A-B   (IIc)

wherein X represents $NH_2$, $NH-C(=NH)-$, and the like or 5 or 6 membered monocyclic aromatic or nonaromatic ring system containing 0, 1, 2, 3 or 4 heteroatoms selected from N, O or S wherein the mono or bicyclic ring system either substituted or unsubstituted, or a 9 to 14 membered polycyclic ring system, wherein one or more of the rings is aromatic and wherein the polycyclic ring system contains 0, 1, 2, 3 or 4 heteroatoms selected from N, O or S, wherein the polycyclic ring system either substituted or unsubstituted; Y is selected from $C_{0-8}$ alkylene, $C_{0-8}$cycloalkyl, $C_{0-8}$ alkylene-$NR^{10}$—CO—$C_{0-8}$ alkylene, $C_{0-8}$alkylene-$CONR^{10}$—$C_{0-8}$ alkylene, $C_{0-8}$ alkylene-O—$C_{0-8}$ alkylene, $C_{0-8}$ alkylene-$NR^{10}$—$C_{0-8}$ alkylene, $C_{0-8}$ alkylene-$S(O)_{0-2}$—$C_{0-8}$ alkylene, $C_{0-8}$ alkylene-$S(O)_{0-2}$—$NR^{10}$—$C_{0-8}$ alkylene, $C_{0-8}$ alkylene-$NR^{10}$—$S(O)_{0-2}$—$C_{0-8}$ alkylene, $C_{0-8}$ alkylene-CO—$C_{0-8}$ alkylene, $(CH_2)_{0-6}$-aryl$(CH_2)_{0-6}$, $(CH_2)_{0-6}$-aryl-CO—$(CH_2)_{0-6}$, $(CH_2)_{0-6}$-aryl-CO—$NR^{10}$-$(CH_2)_{0-6}$, $(CH_2)_{0-6}$-aryl$NR^{10}CO(CH_2)_{0-6}$, or $(CH_2)_{0-8}$—$CH(OR^1)$ $(CH_2)_{0-8}$; Z and A are each independently selected from $(CH_2)_m$, $(CH_2)_mO(CH_2)_n$, $(CH_2)_mNR^{11}(CH_2)_n$, $(CH_2)_m$ $NR^{11}CONR^{12}(CH_2)_n$, $(CH_2)_mCONR^{11}(CH_2)_n$, $(CH_2)_mCO$ $(CH_2)_n$, $(CH_2)_mCS(CH_2)$, $(CH_2)_mNR^{11}SO_2(CH_2)_n$, $(CH_2)_m$ $SNR^{11}(CH_2)_n$, $(CH_2)_mSO_2NR^{11}(CH_2)_n$, $(CH_2)_mNR^{11}SO_{12}$ $(CH_2)_n$, $(CH_2)_mCR^{11}=CR^2(CH_2)_n$, $(CH_2)_mC\equiv C(CH_2)_n$; where m and n are each independently an integer from 0 to 6; Aryl is a 6 membered aromatic ring containing 0, 1, 2 or 3 nitrogen atoms and either unsubstituted or substituted with $R^8$ and $R^9$; B is

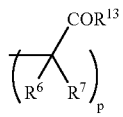

where p is an integer from 1 to 3, $R^6$ is selected from hydrogen, fluorine, $(C_{1-8})$ alkyl, hydroxy, hydroxy $(C_{1-6})$ alkyl, carboxy $(C_{0-6})$alkyl, $(C_{1-6})$ alkyloxy, $(C_{1-6})$alkylcarbonyl, aryl $(C_{1-8})$ alkylcarbonyl, $(C_{1-6})$alkylcarbonyloxy, aryl $(C_{0-6})$ alkylcarbonyloxy, $(C_{1-6})$ alkylaminocarbonyloxy, $(C_{3-8})$cycloalkyl, aryl $(C_{0-6})$ alkyl, $(C_{0-6})$ alkylamino $(C_{0-6})$ alkyl, $(C_{0-6})$ dialkylamino $(C_{0-6})$ alkyl, $(C_{0-6})$ dialkylamino $(C_{0-6})$ alkyl, $(C_{1-8})$ alkylsulfonylamino $(C_{0-6})$ alkyl, aryl $(C_{0-6})$ alkylsulfonylamino $(C_{06})$ alkyl, $(C_{1-8})$ alkoxycarbonylamino $(C_{0-8})$ alkyl, aryl $(C_{0-8})$ alkyloxycarbonylamino $(C_{0-8})$ alkyl, $(C_{1-8})$ alkylcarbonylamino $(C_{0-6})$ alkyl, aryl $(C_{0-6})$ alkylcarbonylamino $(C_{0-6})$ alkyl and the like; $R^7$ is selected from $(C_{7-20})$ polycyclyl $(C_{1-8})$ alkylsulfonylamino $(C_{0-8})$ alkyl and the like, $R^{13}$ is selected from hydroxy, $(C_{1-8})$ alkyloxy and the like;

An example of these compounds is shown in formula (IId)

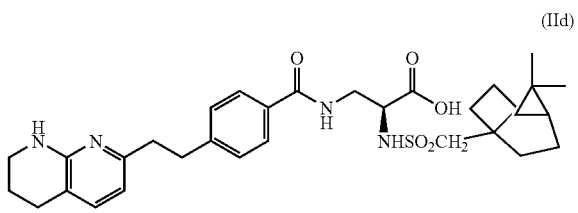

(IId)

iii) International publication No. WO 94/12181 disclose the compounds of general formula (IIe)

X—Y-Z-Ary-A-B   (IIe)

aryl is a 6 membered aromatic ring containing 0, 1, 2 or 3 nitrogen atoms and either unsubstituted or substituted with $R^8$ and $R^9$; X represents $NH_2$, $NH-C(=NH)-$, and the like or 4 to 10 membered mono or polycyclic aromatic or nonaromatic ring system and containing 0, 1, 2, 3 or 4 heteroatoms selected from N, O or S either unsubstituted or substituted; Y is selected from $C_{0-8}$ alkyl, $C_{4-10}$ cycloalkyl, $C_{0-8}$ alkyl-$NR^3$—CO—$C_{0-8}$ alkyl, $C_{0-8}$alkyl-$CONR^3$—$C_{0-8}$ alkyl, $C_{0-8}$ alkyl-O—$C_{0-8}$ alkyl, $C_{0-8}$ alkyl-$S(O)_n$—$C_{0-8}$ alkyl, $(CH_2)_{0-8}$ aryl-$(CH_2)_{0-8}$, $(CH_2)_{0-6}$ aryl-$SO_n$—, $(CH_2)_{0-8}$ aryl-CO—$(CH_2)_{0-8}$, $(CH_2)_{0-6}$ aryl-$SO_2$—$(CH_2)_{0-6}$—, $(CH_2)_{0-6}$ $NR^3$—$(CH_2)_{0-6}$—, $(CH_2)_{0-6}$ aryl-CH (OH)—$(CH_2)_{0-6}$—, $(CH_2)_{0-8}$—CONH—$(CH_2)_{0-8}$—, $C_{0-8}$ alkyl-$SO_2$—$NR^3$—$C_{0-8}$ alkyl, $C_{0-8}$ alkyl-CO—$C_{0-8}$ alkyl, $C_{0-8}$ alkyl-CH(OH)-$C_{0-8}$ alkyl, where n is an integer from 0-2; Z and A are independently chosen from $(CH_2)_m$, $(CH_2)_m$ $O(CH_2)_n$, $(CH_2)_mNR^3(CH_2)_n$, $(CH_2)_mNR^3(CH_2)_n$, $(CH_2)_m$ $CONR^{11}(CH_2)_n$, $(CH_2)_mCO(CH_2)_n$, $(CH_2)_mCS(CH_2)_n$, $(CH_2)_mSO_2(CH_2)_n$, $(CH_2)_mS(CH_2)_n$, $(CH_2)_mSO_2(CH_2)_n$, $(CH_2)_mSO(CH_2)_n$, $(CH_2)_mSO_2NR^3(CH_2)_n$, $(CH_2)_mNR^3SO_2$ $(CH_2)_n$, $(CH_2)_mCR^3=CR^4(CH_2)_n$, $(CH_2)_mC\equiv C(CH_2)_n$, $(CH_2)_mCH(OH)(CH_2)_n$; where m and n are each independently an integer from 0 to 6; Aryl is a 6 membered aromatic ring system containing 0, 1, 2, 3 or 4 N atoms and either unsubstituted or substituted with $R^5$, provided that when A is $(CH_2)_m$, the Aryl ring, bonded by Z and A must contain at least one heteroatom;

B is

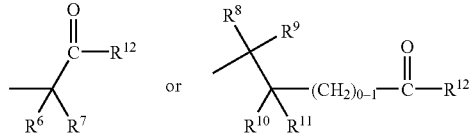

$R^6$, $R^7$, $R^8$, $R^9$, $R^{10}$ and $R^{11}$, are independently selected from hydrogen, fluorine, $(C_{1-8})$ alkyl, hydroxy, hydroxy $(C_{1-6})$ alkyl, carboxy $(C_{0-6})$alkyl, $(C_{1-6})$ alkyloxy, aryl $(C_{0-6})$ alkyloxy, $(C_{3-8})$cycloalkyl, aryl $(C_{0-6})$ alkyl, $(C_{1-6})$alkylcarbonyloxy, $(C_{0-6})$ alkylamino $(C_{0-6})$ alkyl and the like;

$R^{12}$ is selected from hydroxy, $(C_{1-8})$ alkyloxy, aryl $(C_{0-6})$ alkyl and the like;

An example of these compounds is shown in formula (IIf)

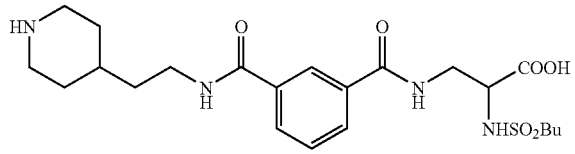

(IIf)

iv) International publication No. WO 93/16697 and U.S. Pat. No. 5,227,490 disclose the compounds of general formula (IIg)

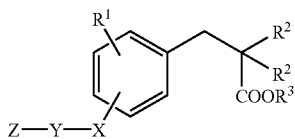

(IIg)

wherein $R^1$ is chosen independently from $(C_1-C_6)$alkyl, aryl$(C_4-C_{10})$alkyl, aryl, carboxy, $(C_1-C_6)$alkyloxy, carboxy $(C_0-C_6)$alkyl, hydroxy$(C_0-C_6)$alkyl, $(C_1-C_4)$alkylsulfonyl $(C_0-C_6)$alkyl, $(C_0-C_4)$alkylamino$(C_0-C_6)$alkyl, aryl$(C_0-C_{10})$alkylamino$(C_0-C_6)$alkyl, $(C_2-C_{10})$acylamino$(C_0-C_6)$alkyl, $(C_1-C_4)$carboalkoxy$(C_0-C_6)$alkyl or halogen atom; $R^2$ is chosen from hydrogen, halogen, hydroxy, $(C_1-C_6)$alkyloxy, aryl$(C_0-C_4)$alkyl, aryl$(C_0-C_6)$alkyloxy, $(C_1-C_6)$alkyl wherein the alkyl group is unsubstituted or substituted with one or more groups chosen from hydroxy, $(C_1-C_4)$alkyloxy, amino$(C_1-C_{10})$ alkylcarbonyl, aryl$(C_0-C_{10})$alkylcarbonyl, aryl$(C_0-C_{10})$alkylcabonylamino, $(C_1-C_6)$ alkylsulfonyl, aryl$(C_0-C_6)$alkylsulfonyl, $(C_1-C_6)$alkylsulfonylamino, aryl$(C_0-C_{10})$ alkylsulfonylamino, $(C_1-C_{10})$alkyloxycarbonylamino, aryl$(C_0-C_6)$alkylamino, aryl$(C_0-C_6)$alkylcarbonylamino, amino, carboxy, aryl, carbonyl-P-or $SO_2$—P wherein P is a single L or D amino acid or a sequence of 2-4 L or D amino acids connected by amide linkage; or $R_2$ represents carboxyl, $(C_1-C_6)$alkylcarbonyl, aryl$(C_1-C_{10})$alkylcarbonyl, $(C_1-C_6)$alkyloxycarbonylamino$(C_1-C_6)$alkyl, $(C_1-C_6)$alkylaminocarbonylamino$(C_1-C_6)$alkyl, aryl$(C_0-C_6)$alkylaminocarbonylamino$(C_1-C_6)$alkyl, aryl$(C_0-C_6)$alkyloxycarbonylamino $(C_1-C_6)$alkyl, $(C_1-C_6)$alkoxycarbonyl or aryl$(C_0-C_6)$alkyloxycarbonyl and provided that when there is more than one $R^2$ on the same carbon atom they may be the same or different; $R^3$ is hydrogen, $(C_1-C_6)$alkyl, aryl$(C_1-C_{10})$alkyl; Z is $NR^4R^5$ wherein $R^4$ and $R^5$ are independently hydrogen, $(C_1-C_6)$alkyl, aryl$(C_1-C_{10})$alkyl wherein said alkyl groups are unsubstituted or substituted with $(C_1-C_4)$ alkyloxy, carboxy $(C_0-C_6)$alkyl, hydroxy, halogen or Z represents a 4-9 membered mono or bicyclic ring system containing 1, 2 or 3 heteroatoms chosen from N, O or S and either unsubstituted or substituted with $R^4$ or $R^5$ or

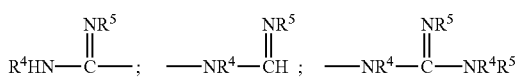

Y is $(C_1-C_{10})$alkyl either unsubstituted or unsubstituted with one or more groups selected from $R^4$ or $R^5$; or Y represents $(C_4-C_8)$cycloalkyl, aryl, $(C_0-C_3)$alkylaryl$(C_0-C_3)$ alkyl, $(C_0-C_3)$alkylaryl$(C_0-C_3)$alkylcarbonyl, $(C_0-C_3)$alkylaryl $(C_0-C_3)$alkylcarboxamido, $(C_0-C_3)$alkylaryloxy$(C_0-C_3)$alkyl, $(C_0-C_3)$alkyloxy$(C_0-C_6)$alkyl,

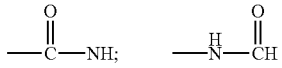

or $—(CH_2)_m—Q—(CH)_n$ where Q is a $C_2-C_8$ membered heterocyclic ring containing 1, 2 or 3 heteroatoms chosen from N, O or S and substituted or unsubstituted with oxo, thio, or $(C_1-C_6)$alkyl and m and n are chosen from the integers 0, 1, 2 or 3; X is O, S, SO, $SO_2$, CO, $—NR^4CO—$, $CONR^4—$, $—CH_2—$, $—CH=CH—$, $—C≡C—$, $—NR^4CS—$, $—CSNR^4—$ or $SO_2NR^4$ or $NR^4SO_2$; An example of these compounds is shown in formula (IIh)

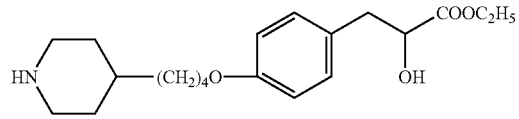

(IIh)

v) International publication No. WO 00/05223 disclose the compounds of general formula (IIi)

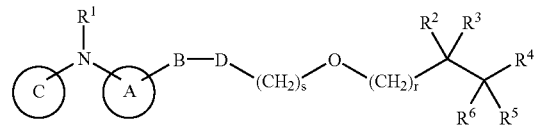

(IIi)

where A is a bicyclic heteroaryl, optionally substituted with one or more substituents; B is linker group connecting group A to groups D and comprising a 3 or 4 atom linker where each atom is independently selected from carbon, oxygen, nitrogen and sulphur and is optionally substituted with one or more $C_{1-6}$ alkyl groups or two of such adjacent alkyl substituents may form a ring; C is aryl or mono or bicyclic heteroaryl, each or which can be optionally substituted; D is an aryl or heteroaryl, both or which are optionally substituted, $R^1$ is hydrogen, $C_{1-5}$ alkyl, $C_{1-3}$ alkanoyl, or $C_{1-3}$ alkoxycarbonyl, $R^2$ to $R^5$ are each independently selected from hydrogen, $C_{1-6}$ alkyl, aryl and heteroaryl containing up to 2 heteroatoms chosen from oxygen, sulphur and nitrogen, the aryl and heteroaryl optionally substituted with $C_{1-6}$ alkyl, $C_{2-6}$ alkenyl, $C_{2-6}$ alkynyl, $C_{1-4}$ alkoxy, $C_{1-4}$ alkanoyl, $C_{1-6}$ alkylamino, $C_{1-4}$ alkyl$C_{1-6}$ alkyloxy, $C_{1-6}$alkylamino$C_{1-6}$alkyl, nitro, cyano, halogen, trifluoromethyl, hydroxy, $(CH_2)_pOH$ where p is 1 or 2, $—COR^a$ and $—CONR^aR^b$, where $R^a$ and $R^b$ are independently selected from hydrogen and $C_{1-6}$ alkyl or two of $R^2$ to $R^5$ can be taken together to form a 3 to 7 membered ring, $R^6$ is an acidic functional group, r and s are each independently 0 or with the proviso that r and s cannot both be 0.

An example of these compounds is shown in formula (IIj)

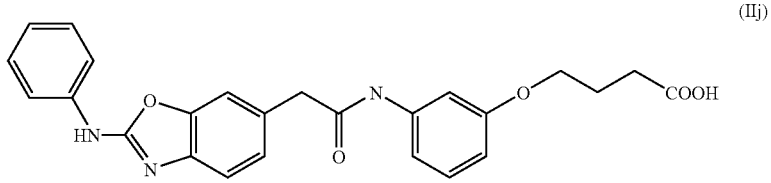

vi) International publication No. WO 00/64888 disclose the compounds of general formula (IIk)

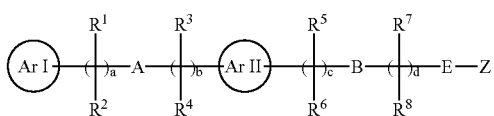

$Ar^1$ and $Ar^2$ are independently aryl, fused arylcycloalkenyl, fused arylcycloalkyl, fused arylheterocyclenyl, fused arylheterocyclyl, heteroaryl, fused heteroarylcycloalkenyl, fused heteroarylcycloalkyl, fused heteroarylcyclenyl or fused heteroarylheterocyclyl; A is O, S, SO, $OS_2$, $NR^{13}C$(O), $NR^{14}C(O)$, $C(O)NR^{14}$, $NR^{14}C(O)N(R^{15})$, $C(R^{14})$=N; chemical bond and the like; B is O, S, $NR^{19}$, a chemical bond, C(O), $N(R^{20})C(O)$ or $C(O)N(R^{20})$; E is a chemical bond or an ethylene groups; a is 0-6; b is 0-4; c is 0-4; d is 0-6; g is 1-5; h is 1-4; $R^1$, $R^3$, $R^5$ and $R^7$ are independently hydrogen, halogen alkyl, carbonyl, alkoxycarbonyl, or aralkyl; $R^2$, $R^4$, $R^6$ and $R^8$ are independently —$(CH_2)_q$—X; q is 0-3; X is hydrogen, halogen, alkyl, alkenyl, cycloalkyl, heterocyclyl, aryl, heteroaryl, aralkyl, heteroaralkyl, hydroxy, alkoxy, aralkoxy, heteroaralkoxy, carbonyl, alkoxycarbonyl, tetrazolyl, acyl, acylHNSO$_2$, and the like; Z is $R^{21}O2C$, $R^{21}OC$, cyclo-imide; CN, $R^{21}O_2SHNCO$, $R^{21}O_2SNH$, $R^{21}NCO$, $R^{21}O$-2,4-thiazolidinonyl or tetrazolyl.

An example of these compounds is shown in formula (III)

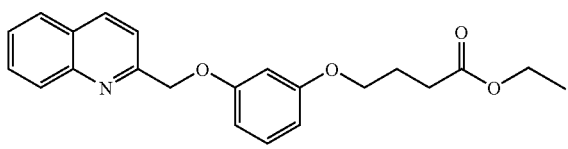

SUMMARY OF THE INVENTION

The present invention provides novel compounds of the formula (I), their derivatives, their analogs, their tautomeric forms, their stereoisomers, their polymorphs, their pharmaceutically acceptable salts, their pharmaceutically acceptable solvates and pharmaceutical compositions containing them or their mixtures having good stability and solubility, which can be used for the treatment and/or prophylaxis of diseases related to increased levels of lipids, especially to treat hyperlipidemia, and for the treatment of type II diabetes, impaired glucose intolerance, leptin resistance, atherosclerosis, disorders related to Syndrome X such as hypertension, obesity, insulin resistance, coronary artery disease and other cardiovascular disorders, renal diseases including glomerulonephritis, glomerulosclerosis, nephrotic syndrome, hypertensive nephrosclerosis, nephropathy; retinopathy, disorders related to endothelial cell activation, psoriasis, polycystic ovarian syndrome (PCOS), dementia, diabetic complications, eating disorders, osteoporosis, inflammatory bowel diseases, myotonic dystrophy, pancreatitis, retinopathy, arteriosclerosis, xanthoma or cancer with better efficacy, potency and lower toxicity.

The present invention provides novel compounds of the formula (I) and their derivatives, their analogs, their tautomeric forms, their stereoisomers, their polymorphs, their pharmaceutically acceptable salts, their pharmaceutically acceptable solvates and pharmaceutical compositions containing them or their mixtures which may have agonist activity against PPARα and/or PPARγ, and optionally inhibit HMG CoA reductase, in addition to agonist activity against PPARα and/or PPARγ.

The present invention provides novel compounds of the formula (I) and their derivatives, their analogs, their tautomeric forms, their stereoisomers, their polymorphs, their pharmaceutically acceptable salts, their pharmaceutically acceptable solvates and pharmaceutical compositions containing them or their mixtures having enhanced activities, without toxic effect or with reduced toxic effect.

The present invention provides a process for the preparation of novel compounds of the formula (I) as defined above, their analogs, their tautomeric forms, their stereoisomers, their pharmaceutically acceptable salts, their polymorphs and their pharmaceutically acceptable solvates.

The present invention provides pharmaceutical compositions containing novel compounds of the general formula (I), their analogs, their derivatives, their tautomers, their stereoisomers, their polymorphs, their pharmaceutically acceptable salts, solvates or their mixtures in combination with suitable carriers, solvents, diluents and other media normally employed in preparing such compositions.

DETAILED DESCRIPTION OF THE INVENTION

The present invention relates to compounds having the general formula (I)

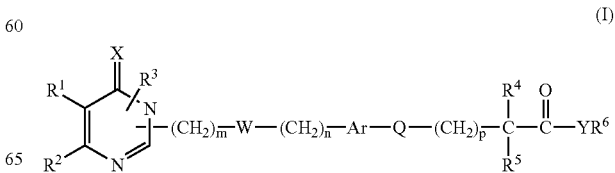

their derivatives, their analogs, their tautomeric forms, their stereoisomers, their polymorphs, their pharmaceutically acceptable salts, their pharmaceutically acceptable solvates and pharmaceutical compositions containing them or their mixtures wherein X represents O or S; the groups $R^1$, $R^2$ and the group $R^3$ when attached to the carbon atom, may be same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its derivatives, or sulfonic acid or its derivatives; $R^3$ when attached to nitrogen atom represents hydrogen, hydroxy, formyl or substituted or unsubstituted groups selected from alkyl, cycloalkyl, alkoxy, cycloalkoxy, aryl, aralkyl, heterocyclyl, heteroaryl, heteroaralkyl, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl groups, carboxylic acid or its derivatives, or sulfonic acid or its derivatives; the linking group represented by $-(CH_2)_m-W-(CH_2)_n-$ is attached either through nitrogen atom or through carbon atom; W represents O, S, $NR^7$, $-C(=O)$, $-O-C(=O)$, $C(=O)-O$, $C(=O)-NR^7$, $-O-C(=O)-NR^7$, $NR^7-(CH_2)_nC(=O)-NR^7$, $NR^7-C(=O)-O-$, $NR^7-C(=O)-NR^7$, $NR^7-C(=O)$, $SO_2-NR^7$, $NR^7-SO_2$, where $R^7$ represents hydrogen, $(C_1-C_{12})$ alkyl, or substituted or unsubstituted aryl, aralkyl group; m and n are integers ranging from 0-4; Ar represents substituted or unsubstituted divalent single or fused aromatic or heterocyclic group; $R^4$ and $R^5$ may be same or different and represent hydrogen, hydroxy, alkoxy, halogen or substituted or unsubstituted groups selected from $(C_1-C_{12})$ alkyl, aralkyl or heteroaralkyl groups; $R^6$ may be hydrogen or substituted or unsubstituted groups selected from $(C_1-C_{12})$ alkyl, cycloalkyl, aryl, aralkyl, heterocyclyl, heteroaryl or heteroaralkyl groups; Y represents oxygen or $NR^8$, where $R^8$ represents hydrogen or substituted or unsubstituted groups selected from alkyl, aryl, hydroxyalkyl, aralkyl heterocyclyl, heteroaryl, or heteroaralkyl groups; $R^6$ and $R^8$ together may form a substituted or unsubstituted 5 or 6 membered cyclic structure containing carbon atoms, one or two nitrogen atoms and may optionally contain one or more heteroatoms selected from oxygen, or sulfur; Q represents O, S, SO, $SO_2$ or $NR^9$ wherein $R^9$ represents hydrogen, substituted or unsubstituted groups selected from $(C_1-C_{12})$ alkyl, cycloalkyl, aryl, hydroxyalkyl, aralkyl heterocyclyl, heteroaryl, or heteroaralkyl groups; p is an integer of 0 or 1;

Suitable groups represented by $R^1$, $R^2$ and the group $R^3$ when attached to carbon atom, may be selected from hydrogen, halogen atom such as fluorine, chlorine, bromine or iodine; hydroxy, cyano, nitro, formyl, substituted or unsubstituted $(C_1-C_{12})$alkyl group, especially, linear or branched $(C_1-C_{10})$alkyl group, such as methyl, ethyl, n-propyl, isopropyl, n-butyl, iso-butyl, t-butyl, n-pentyl, iso-pentyl, hexyl, heptyl, octyl and the like; cyclo($C_3-C_6$)alkyl group such as cyclopropyl, cyclobutyl, cyclopentyl, cyclohexyl and the like, the cycloalkyl group may be substituted; $(C_1-C_6)$alkoxy such as methoxy, ethoxy, propyloxy, butyloxy, iso-propyloxy and the like, which may be substituted; cyclo($C_3-C_6$)alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aryloxy group such as phenoxy, naphthyloxy and the like, the aryloxy group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, pyridinemethyl, furanethyl, pyridineethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; acyl group such as acetyl, propionyl, benzoyl and the like, the acyl group may be substituted; acyloxy group such as OOCMe, OOCEt, OOCPh and the like, which may be substituted; acylamino groups such as $NHCOCH_3$, $NHCOC_2H_5$, $NHCOC_3H_7$, $NHCOC_6H_5$ and the like, which may be substituted; monoalkylamino group such as $NHCH_3$, $NHC_2H_5$, $NHC_3H_7$,$NHC_6H_{13}$, and the like, which may be substituted; dialkylamino group such as $N(CH_3)_2$, $NCH_3(C_2H_5)$, $N(C_2H_5)_2$ and the like, which may be substituted; arylamino group such as $HNC_6H_5$, $NCH_3(C_6H_5)$, $NHC_6H_4CH_3$, $NHC_6H_4$-Hal and the like, which may be substituted; aralkylamino group such as $C_6H_5CH_2NH$, $C_6H_5CH_2CH_2NH$, $C_6H_5CH_2NCH_3$ and the like, which may be substituted; amino group; amino($C_1-C_6$) alkyl such as aminomethyl, aminoethyl, aminopropyl and the like, which may be substituted; $(C_1-C_6)$hydroxyalkyl, which may be substituted; alkoxyalkyl group such as methoxymethyl, ethoxymethyl, methoxyethyl, ethoxyethyl and the like, the alkoxyalkyl group may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH2$, $C_6H_5CH_2OCH_2CH_2$ and the like, which may be substituted; alkoxycarbonyl such as methoxycarbonyl, ethoxycarbonyl and the like, which may be substituted; aryloxycarbonyl group such as phenoxycarbonyl, naphthyloxycarbonyl and the like, the aryloxycarbonyl group may be substituted; aralkoxycarbonyl group such as benzyloxycarbonyl, phenethyloxycarbonyl, naphthylmethoxycarbonyl and the like, which may be substituted; thio($C_1-C_6$)alkyl, which may be substituted; $(C_1-C_6)$alkylthio which may be substituted; alkoxycarbonylamino group such as $NHCOOC_2H_5$, $NHCOOCH_3$ and the like, which may be substituted; aryloxycarbonylamino group such as $NHCOOC_6H_5$, $NCH_3COOC_6H_5$, $NC_2H_5COOC_6H_5$, $NHCOOC_6H_4CH_3$, $NHCOOC_6H_4OCH_3$ and the like, which may be substituted; aralkoxycarbonylamino group such as $NHCOOCH_2C_6H_5$, $NHCOOCH_2CH_2C_6H_5$, $N(CH_3)COOCH_2C_6H_5$, $N(C_2H_5)COOCH_2C_6H_5$, $NHCOOCH_2C_6H_4CH_3$, $NHCOOCH_2C_6H_4OCH_3$ and the like, which may be substituted; carboxylic acid or its derivatives such as amides, like $CONH_2$, CONHMe, $CONMe_2$, CONHEt, $CONEt_2$, CONHPh and the like, the carboxylic acid derivatives may be substituted; sulfonic acid or its derivatives such as amides, like $SO_2NH_2$, $SO_2NHMe$, $SO_2NMe_2$, $SO_2NHCF_3$ and the like, the sulfonic acid derivatives may be substituted.

When the groups represented by $R^1$, $R^2$ and the group $R^3$ when attached to carbon atom are substituted, the substituents may be selected from halogen, hydroxy, nitro, thio or unsubstituted or substituted groups selected from alkyl, cycloalkyl, alkoxy, cycloalkoxy, aryl, aralkyl, aryloxy, aralkoxy, alkoxyalkyl, aryloxyalkyl, aralkoxyalkyl, heterocyclyl, heteroaryl, heteroaralkyl, acyl, acyloxy, hydroxyalkyl, amino, acylamino, arylamino, aminoalkyl, alkoxycarbonyl, monoalkylamino, dialkyamino, alkylthio, carboxylic acid or its derivatives or sulfonic acid or its derivatives. These groups are as defined above.

It is preferred that the substituents on by $R^1$, $R^2$ and the group $R^3$ represents halogen atom such as fluorine, chlorine or bromine; alkyl group such as methyl, ethyl, iso-propyl, n-propyl, n-butyl; cycloalkyl group such as cyclopropyl; aryl group such as phenyl; aralkyl group such as benzyl; ($C_1$-$C_3$)alkoxy, benzyloxy, hydroxy group, acyl or acyloxy groups.

Suitable groups represented by $R^3$ when attached to nitrogen atom may be selected from hydrogen, hydroxy, formyl; substituted or unsubstituted ($C_1$-$C_{12}$)alkyl group, especially, linear or branched ($C_1$-$C_6$)alkyl group, such as methyl, ethyl, n-propyl, isopropyl, n-butyl, iso-butyl, t-butyl, n-pentyl, isopentyl, hexyl and the like; ($C_1$-$C_6$)alkoxy such as methoxy, ethoxy, propyloxy, butyloxy, iso-propyloxy and the like, which may be substituted; cyclo($C_3$-$C_6$)alkyl group such as cyclopropyl, cyclobutyl, cyclopentyl, cyclohexyl and the like, the cycloalkyl group may be substituted; cyclo($C_3$-$C_6$)alkoxy group such as cyclopropyloxy, cyclobutyloxy, cyclopentyloxy, cyclohexyloxy and the like, the cycloalkoxy group may be substituted; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted and the substituted aralkyl is a group such as $CH_3C_6H_4CH_2$, $Hal-C_6H_4CH_2$, $CH_3OC_6H_4CH_2$, $CH_{3O}C_6H_4CH_2CH_2$ and the like; aryloxy group such as phenoxy, naphthyloxy and the like, the aryloxy group may be substituted; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, pyridinemethyl, furanethyl, pyridineethyl, oxazolemethyl, oxazolethyl and the like, the heteroaralkyl group may be substituted; heteroaryloxy and heteroaralkoxy, wherein heteroaryl and heteroaralkyl moieties are as defined earlier and may be substituted; monoalkylamino group such as $NHCH_3$, $NHC_2H_5$, $NHC_3H_7$, $NHC_6H_{13}$ and the like, which may be substituted; dialkylamino group such as $N(CH_3)_2$, $NCH_3(C_2H_5)$, $N(C_2H_5)_2$ and the like, which may be substituted; acylamino groups such as $NHCOCH_3$, $NHCOC_2H_5$, $NHCOC_3H_7$, $NHCOC_6H_5$ and the like, which may be substituted; arylamino group such as $HNC_6H_5$, $NCH_3(C_6H_5)$, $NHC_6H_4CH_3$, $NHC_6H_4$-Hal and the like, which may be substituted; amino group; aralkylamino group such as $C_6H_5CH_2NH$, $C_6H_5CH_2CH_2NH$, $C_6H_5CH_2NCH_3$ and the like, which may be substituted; amino($C_1$-$C_6$) alkyl such as aminomethyl, aminoethyl, aminopropyl and the like, which may be substituted; ($C_1$-$C_6$)hydroxyalkyl, which may be substituted; alkoxyalkyl group such as methoxymethyl, ethoxymethyl, methoxyethyl, ethoxyethyl and the like, the alkoxyalkyl group may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; alkoxycarbonyl group such as methoxycarbonyl, ethoxycarbonyl and the like, which may be substituted; aryloxycarbonyl group such as phenoxycarbonyl, naphthyloxycarbonyl and the like, which may be substituted; aralkoxycarbonyl group such as benzyloxycarbonyl, phenethyloxycarbonyl, naphthylmethoxycarbonyl and the like, which may be substituted; carboxylic acid or its derivatives such as amides, like $CONH_2$, $CONHMe$, $CONMe_2$, $CONHEt$, $CONEt_2$, $CONHPh$ and the like, the carboxylic acid derivatives may be substituted; sulfonic acid derivatives such as amides, like $SO_2NH_2$, $SO_2NHMe$, $SO_2NMe_2$, $SO_2NHCF_3$ and the like, the sulfonic acid derivatives may be substituted.

When the groups represented by $R^3$ attached to nitrogen are substituted, substituents may be selected from halogen such as fluorine or chlorine; hydroxy, acyl, acyloxy or amino groups. These groups are as defined above.

Suitable groups represented by $R^4$ and $R^5$ may be selected from hydrogen, hydroxy, ($C_1$-$C_3$)alkoxy group such as methoxy, ethoxy, propoxy and the like; halogen atom such as fluorine, chlorine, bromine or iodine; ($C_1$-$C_{12}$)alkyl groups such as methyl, ethyl, propyl, isopropyl, butyl, isobutyl, pentyl, hexyl, heptyl, and the like, which may be substituted; aralkyl such as benzyl, phenethyl and the like, which may be substituted or heteroaralkyl such as pyridinemethyl, pyridineethyl, furanmethyl, oxazolemethyl, oxazolethyl, furanethyl and the like, the heteroaralkyl group may be substituted. The substituents are selected from halogen, hydroxy or ($C_1$-$C_6$)alkyl groups.

Suitable groups represented by $R^6$ may be selected from hydrogen, linear or branched ($C_1$-$C_{16}$)alkyl, preferably ($C_1$-$C_{12}$)alkyl group such as methyl, ethyl, n-propyl, iso-propyl, n-butyl, iso-butyl, pentyl, hexyl, octyl and the like, the alkyl group may be substituted; ($C_3$-$C_7$)cycloalkyl such as cyclopropyl, cyclopentyl, cyclohexyl and the like, the cycloalkyl group may be substituted; aryl group such as phenyl, naphthyl and the like, the aryl group may be substituted; heteroaryl group such as pyridyl, thienyl, pyrrolyl, furyl and the like, the heteroaryl group may be substituted; heteroaralkyl group such as furanmethyl, furanethyl, pyridinemethyl, pyridineethyl, oxazolemethyl, oxazolethyl and the like, the heteroaralkyl group may be substituted; aralkyl group such as benzyl, phenethyl and the like, the aralkyl group may be substituted; heterocyclyl group such as aziridinyl, pyrrolidinyl, piperidinyl and the like, the heterocyclyl group may be substituted. The substituents on $R^6$ may be selected from halogen, hydroxy, nitro or unsubstituted or substituted groups selected from ($C_1$-$C_6$)alkyl, ($C_3$-$C_7$)cycloalkyl, ($C_1$-$C_6$)alkoxy, ($C_3$-$C_7$)cycloalkoxy, aryl, aralkyl, aralkoxy ($C_1$-$C_6$)alkyl, heterocyclyl, heteroaryl, heteroaralkyl, ($C_1$-$C_6$) acyl, ($C_1$-$C_6$)acyloxy, hydroxy ($C_1$-$C_6$)alkyl, amino, ($C_1$-$C_6$) acylamino, arylamino, amino ($C_1$-$C_6$)alkyl, aryloxy, aralkoxy, ($C_1$-$C_6$) alkoxycarbonyl, ($C_1$-$C_6$)alkylamino, ($C_1$-$C_6$)alkoxyalkyl, ($C_1$-$C_6$)alkylthio, thio ($C_1$-$C_6$)alkyl groups, carboxylic acid or its derivatives, or sulfonic acid or its derivatives. The substituents are as defined above.

Suitable groups represented by $R^7$ may be selected from hydrogen, linear or branched ($C_1$-$C_{12}$)alkyl group, such as methyl, ethyl, n-propyl, iso-propyl, n-butyl, iso-butyl, t-butyl, n-pentyl, iso-pentyl, hexyl, heptyl, octyl, nonyl and the like; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted. The substituents may be selected from hydroxy, halogen, linear or branched $(C_1-C_{10})$alkyl such as methyl, ethyl, iso-propyl, n-butyl, iso-butyl, t-butyl, n-pentyl, iso-pentyl, hexyl, heptyl, octyl and the like; $(C_1-C_6)$alkoxy such as methoxy, ethoxy, propyloxy, isopropyloxy, butyloxy and the like; aryl group such as phenyl, naphthyl and the like; aralkyl group such as benzyl, phenethyl, naphthylmethyl and the like.

Suitable groups represented by $R^8$ may be selected from hydrogen, linear or branched $(C_1-C_{16})$alkyl, preferably $(C_1-C_{12})$alkyl group such as methyl, ethyl, n-propyl, iso-propyl, n-butyl, iso-butyl, pentyl, hexyl, octyl and the like, the alkyl group may be substituted; hydroxy$(C_1-C_6)$alkyl, the hydroxy $(C_1-C_6)$alkyl group may be substituted; aryl group such as phenyl, naphthyl and the like, the aryl group may be substituted; aralkyl group such as benzyl, phenethyl and the like, the aralkyl group may be substituted; heterocyclyl group such as aziridinyl, pyrrolidinyl, piperidinyl and the like, the heterocyclyl group may be substituted; heteroaryl group such as pyridyl, thienyl, pyrrolyl, furyl and the like, the heteroaryl group may be substituted; heteroaralkyl group such as furanmethyl, furanethyl, pyridinemethyl, pyridineethyl, oxazolemethyl, oxazolethyl and the like, the heteroaralkyl group may be substituted. The substituents may be selected from hydroxy, halogen, linear or branched $(C_1-C_{10})$alkyl such as methyl, ethyl, iso-propyl, n-butyl, iso-butyl, t-butyl, n-pentyl, iso-pentyl, hexyl, heptyl, octyl and the like; $(C_1-C_6)$alkoxy such as methoxy, ethoxy, propyloxy, isopropyloxy, butyloxy and the like; aryl group such as phenyl, naphthyl and the like; aralkyl group such as benzyl, phenethyl, naphthylmethyl and the like.

Suitable ring structures formed by $R^6$ and $R^8$ together may be selected from pyrrolidinyl, piperidinyl, morpholinyl, piperazinyl and the like.

Suitable groups represented by $R^9$ may be selected from hydrogen, substituted or unsubstituted $(C_1-C_{12})$alkyl group, especially, linear or branched $(C_1-C_{10})$alkyl group, such as methyl, ethyl, n-propyl, iso-propyl, n-butyl, iso-butyl, t-butyl, n-pentyl, iso-pentyl, hexyl, heptyl, octyl, nonyl and the like; cyclo$(C_3-C_6)$alkyl group such as cyclopropyl, cyclobutyl, cyclopentyl, cyclohexyl and the like, the cycloalkyl group may be substituted; aryl group such as phenyl, naphthyl and the like, the aryl group may be substituted; aralkyl such as benzyl, phenethyl, $C_6H_5CH_2CH_2CH_2$, naphthylmethyl and the like, the aralkyl group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, thiazolyl, imidazolyl, oxadiazolyl, tetrazolyl, benzopyranyl, benzofuryl and the like, the heteroaryl group may be substituted; heteroaralkyl group such as furanmethyl, furanethyl, pyridinemethyl, pyridineethyl, oxazolemethyl, oxazolethyl and the like, the heteroaralkyl group may be substituted; hydroxy$(C_1-C_6)$alkyl, which may be substituted. The substituents may be selected from hydroxy, halogen, $(C_1-C_6)$ alkyl or $(C_1-C_6)$alkoxy groups.

Suitable groups represented by Ar may be selected from substituted or unsubstituted groups selected from divalent phenylene, naphthylene, pyridyl, quinolinyl, benzofuryl, dihydrobenzofuryl, benzopyranyl, dihydrobenzopyranyl, indolyl, indolinyl, azaindolyl, azaindolinyl, pyrazolyl, benzothiazolyl, benzoxazolyl and the like. The substituents on the group represented by Ar may be selected from linear or branched optionally halogenated $(C_1-C_6)$alkyl, optionally halogenated $(C_1-C_3)$alkoxy, halogen, nitro, acyl, amino, acylamino, thio or carboxylic or sulfonic acids and their derivatives. The substituents are defined as they are for $R^1$—$R^4$.

It is more preferred that Ar represent substituted or unsubstituted divalent, phenylene, naphthylene, benzofuryl, indolyl, indolinyl, quinolinyl, azaindolyl, azaindolinyl, benzothiazolyl or benzoxazolyl groups.

It is still more preferred that Ar is represented by divalent phenylene, naphthylene or benzofuryl, which may be unsubstituted or substituted by alkyl, haloalkyl, methoxy or haloalkoxy groups.

Suitable n is an integer ranging from 0 to 4, preferably n represents an integer 0 to 2.

Suitable m is an integer ranging from 1 to 2.

Suitable p is an integer ranging of 0 or 1.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids such as D-isomers or substituted amino acids; guanidine, substituted guanidine wherein the substituents are selected from nitro, amino, alkyl, alkenyl, or alkynyl; ammonium or substituted ammonium salts and aluminum salts. Salts may include acid addition salts where appropriate which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the present invention include:

(±) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(+) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(−) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(+) Ethyl 2-{4-[2-(2-ethyl-6-oxo-4-phenyl-1,6-dihydropyrimidin-1-yl)ethyl(heptyl)carbamoyl]phenoxy}-2-methyl propanoate;

(+) Ethyl 2-{4-[2-(2-ethyl-6-oxo-4-phenyl-1,6-dihydropyrimidin-1-yl)ethyl(heptyl)carbamoyl]phenoxy}-2-methyl propanoate;

(−) Ethyl 2-{4-[2-(2-ethyl-6-oxo-4-phenyl-1,6-dihydropyrimidin-1-yl)ethyl(heptyl)carbamoyl]phenoxy}-2-methyl propanoate;
(±) Ethyl 2-{4-[2-(2-ethyl-6-oxo-4-phenyl-1,6-dihydropyrimidin-1-yl) ethylcarbamoyl]phenoxy}-2-methyl propanoate;
(+) Ethyl 2-{4-[2-(2-ethyl-6-oxo-4-phenyl-1,6-dihydropyrimidin-1-yl) ethylcarbamoyl]phenoxy}-2-methyl propanoate;
(−) Ethyl 2-{4-[2-(2-ethyl-6-oxo-4-phenyl-1,6-dihydropyrimidin-1-yl) ethylcarbamoyl]phenoxy}-2-methyl propanoate;
(±) Ethyl 2-[4-(2-ethyl-6-oxo-4-phenyl-1,6-dihydropyrlmidin-1-ylmethylcarboxamido)phenoxyl}-2-methyl propanoate;
(+) Ethyl 2-[4-(2-ethyl-6-oxo-4-phenyl-1,6-dihydropyrimidin-1-ylmethylcarboxamido)phenoxy}-2-methyl propanoate;
(−) Ethyl 2-[4-(2-ethyl-6-oxo-4-phenyl-1,6-dihydropyrimidin-1-ylmethylcarboxamido)phenoxy}-2-methyl propanoate;
(±) Ethyl 2-[4-(2-Ethyl-6-oxo-4-phenyl-1,6-dihydropyrimidin-1-ylmethyl(heptyl)carboxamido)phenoxy]-2-methyl propanoate;
(+) Ethyl 2-[4-(2-Ethyl-6-oxo-4-phenyl-1,6-dihydropyrimidin-1-ylmethyl(heptyl)carboxamido)phenoxy]-2-methyl propanoate;
(−) Ethyl 2-[4-(2-Ethyl-6-oxo-4-phenyl-1,6-dihydropyrimidin-1-ylmethyl(heptyl)carboxamido)phenoxy]-2-methyl propanoate;
(±) Ethyl 2-[4-(2-ethyl-6-oxo-4-phenyl-1,6-dihydropyrimidin-1-ylmethyl(heptyl)carboxamido)phenyl sulfanyl]-2-methyl propanoate;
(+) Ethyl 2-[4-(2-ethyl-6-oxo-4-phenyl-1,6-dihydropyrlmidin-1-ylmethyl(heptyl)carboxamido)phenyl sulfanyl]-2-methyl propanoate;
(−) Ethyl 2-[4-(2-ethyl-6-oxo-4-phenyl-1,6-dihydropyrimidin-1-ylmethyl(heptyl)carboxamido)phenyl sulfanyl]-2-methyl propanoate;
(±) Ethyl 2-[4-(2-ethyl-6-oxo-4-phenyl-1,6-dihydropyrimidin-1-ylmethyl(heptyl)carboxamido)phenoxy]-2-methyl butanoate;
(+) Ethyl 2-[4-(2-ethyl-6-oxo-4-phenyl-1,6-dihydropyrimidin-1-ylmethyl(heptyl)carboxamido)phenoxy]-2-methyl butanoate;
(−) Ethyl 2-[4-(2-ethyl-6-oxo-4-phenyl-1,6-dihydropyrimidin-1-ylmethyl(heptyl)carboxamido)phenoxy]-2-methyl butanoate;
(±) Ethyl 2-[4-(2-ethyl-6-oxo-4-phenyl-1,6-dihydropyrimidin-1-ylmethyl(heptyl)carboxamido)phenyl sulfanyl]pentanoate;
(+) Ethyl 2-[4-(2-ethyl-6-oxo-4-phenyl-1,6-dihydropyrimidin-1-ylmethyl(heptyl)carboxamido)phenyl sulfanyl]pentanoate;
(−) Ethyl 2-[4-(2-ethyl-6-oxo-4-phenyl-1,6-dihydropyrimidin-1-ylmethyl(heptyl)carboxamido)phenyl sulfanyl]pentanoate;
(±) Ethyl 2-[4-(2-ethyl-6-oxo-4-phenyl-1,6-dihydropyrimidin-1-ylmethylcarboxamido)phenoxy]octanoate;
(+) Ethyl 2-[4-(2-ethyl-6-oxo-4-phenyl-1,6-dihydropyrimidin-1-ylmethylcarboxamido)phenoxy]octanoate;
(−) Ethyl 2-[4-(2-ethyl-6-oxo-4-phenyl-1,6-dihydropyrimidin-1-ylmethylcarboxamido)phenoxy]octanoate;
(±) Ethyl 2-[4-(2-ethyl-6-oxo-4-phenyl-1,6-dihydropyrimidin-1-ylmethyl(heptyl)carboxamido)phenyl sulfanyl]butanoate;
(+) Ethyl 2-[4-(2-ethyl-6-oxo-4-phenyl-1,6-dihydropyrimidin-1-ylmethyl(heptyl)carboxamido)phenyl sulfanyl]butanoate;
(−) Ethyl 2-[4-(2-ethyl-6-oxo-4-phenyl-1,6-dihydropyrimidin-1-ylmethyl(heptyl)carboxamido)phenyl sulfanyl]butanoate;
(±) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(+) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(−) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(±) Ethyl 2-[4-(2-ethyl-6-oxo-4-phenyl-1,6-dihydropyrimidin-1-ylmethyl(heptyl)carboxamido) phenoxy}pentanoate;
(+) Ethyl 2-[4-(2-ethyl-6-oxo-4-phenyl-1,6-dihydropyrimidin-1-ylmethyl(heptyl)carboxamido) phenoxy}pentanoate;
(−) Ethyl 2-[4-(2-ethyl-6-oxo-4-phenyl-1,6-dihydropyrimidin-1-ylmethyl(heptyl)carboxamido) phenoxy}pentanoate;
(±) Ethyl 2-[4-(2-ethyl-6-oxo-4-phenyl-1,6-dihydropyrimidin-1-ylmethylcarboxamido)phenyl sulfanyl}-3-methyl butanoate;
(+) Ethyl 2-[4-(2-ethyl-6-oxo-4-phenyl-1,6-dihydropyrimidin-1-ylmethylcarboxamido)phenyl sulfanyl}-3-methyl butanoate;
(−) Ethyl 2-[4-(2-ethyl-6-oxo-4-phenyl-1,6-dihydropyrimidin-1-ylmethylcarboxamido)phenyl sulfanyl}-3-methyl butanoate;
(±) Ethyl 2-{4-[2-(2-ethyl-6-oxo-4-phenyl-1,6-dihydropyrimidin-1-yl)ethoxy]phenoxy}-2-methyl propanoate;
(+) Ethyl 2-{4-[2-(2-ethyl-6-oxo-4-phenyl-1,6-dihydropyrimidin-1-yl)ethoxy]phenoxy}-2-methyl propanoate;
(−) Ethyl 2-{4-[2-(2-ethyl-6-oxo-4-phenyl-1,6-dihydropyrimidin-1-yl)ethoxy]phenoxy}-2-methyl propanoate;
(±) Ethyl 2-{4-[2-(2-ethyl-6-oxo-4-phenyl-1,6-dihydropyrimidin-1-yl)ethoxy]phenoxy}-2-methyl butanoate;
(+) Ethyl 2-{4-[2-(2-ethyl-6-oxo-4-phenyl-1,6-dihydropyrimidin-1-yl)ethoxy]phenoxy}-2-methyl butanoate;
(−) Ethyl 2-{4-[2-(2-ethyl-6-oxo-4-phenyl-1,6-dihydropyrimidin-1-yl)ethoxy]phenoxy}-2-methyl butanoate;
(±) Ethyl 2-{4-[2-(2-ethyl-6-oxo-4-phenyl-1,6-dihydropyrimidin-1-yl)ethoxy]phenoxy}pentanoate;
(+) Ethyl 2-{4-[2-(2-ethyl-6-oxo-4-phenyl-1,6-dihydropyrimidin-1-yl)ethoxy]phenoxy}pentanoate;
(−) Ethyl 2-{4-[2-(2-ethyl-6-oxo-4-phenyl-1,6-dihydropyrimidin-1-yl)ethoxy]phenoxy}pentanoate;
(±) Ethyl 2-{4-[2-(2-ethyl-6-oxo-4-phenyl-1,6-dihydropyrimidin-1-yl)ethyl amino]phenylsulfanyl}-3-methyl butanoate;
(+) Ethyl 2-{4-[2-(2-ethyl-6-oxo-4-phenyl-1,6-dihydropyrimidin-1-yl)ethyl amino]phenylsulfanyl}-3-methyl butanoate;
(−) Ethyl 2-{4-[2-(2-ethyl-6-oxo-4-phenyl-1,6-dihydropyrimidin-1-yl)ethyl amino]phenylsulfanyl}-3-methyl butanoate;
(±) Ethyl 2-{4-[2-(2-ethyl-6-oxo-4-phenyl-1,6-dihydropyrimidin-1-yl)ethylamino]phenyl sulfanyl}butanoate;
(+) Ethyl 2-{4-[2-(2-ethyl-6-oxo-4-phenyl-1,6-dihydropyrimidin-1-yl)ethylamino]phenyl sulfanyl}butanoate;
(−) Ethyl 2-{4-[2-(2-ethyl-6-oxo-4-phenyl-1,6-dihydropyrimidin-1-yl)ethylamino]phenyl sulfanyl}butanoate;

(±) Ethyl 2-{4-[2-(2-ethyl-6-oxo-4-phenyl-1,6-dihydropyrimidin-1-yl)ethoxy]phenyl sulfanyl}-3-methyl butanoate;

(+) Ethyl 2-{4-[2-(2-ethyl-6-oxo-4-phenyl-1,6-dihydropyrimidin-1-yl)ethoxy]phenyl sulfanyl}-3-methyl butanoate;

(−) Ethyl 2-{4-[2-(2-ethyl-6-oxo-4-phenyl-1,6-dihydropyrimidin-1-yl)ethoxy]phenyl sulfanyl}-3-methyl butanoate;

(±) Ethyl 2-{4-[2-(2-ethyl-6-oxo-4-phenyl-1,6-dihydropyrimidin-1-yl)ethylamino]phenyl sulfanyl}-4-methyl pentanoate;

(+) Ethyl 2-{4-[2-(2-ethyl-6-oxo-4-phenyl-1,6-dihydropyrimidin-1-yl)ethylamino]phenyl sulfanyl}-4-methyl pentanoate;

(−) Ethyl 2-{4-[2-(2-ethyl-6-oxo-4-phenyl-1,6-dihydropyrimidin-1-yl)ethylamino]phenyl sulfanyl}-4-methyl pentanoate;

(±) Ethyl 2-{4-[2-(2-ethyl-6-oxo-4-phenyl-1,6-dihydropyrimidin-1-yl)ethylsulfanyl]phenoxy}acetate;

(+) Ethyl 2-{4-[2-(2-ethyl-6-oxo-4-phenyl-1,6-dihydropyrimidin-1-yl)ethylsulfanyl]phenoxyl acetate;

(−) Ethyl 2-{4-[2-(2-ethyl-6-oxo-4-phenyl-1,6-dihydropyrimidin-1-yl)ethylsulfanyl]phenoxy}acetate;

(±) Ethyl 2-{4-[2-(2-ethyl-6-oxo-4-phenyl-1,6-dihydropyrimidin-1-yl)ethoxy]anilino}propanoate;

(+) Ethyl 2-{4-[2-(2-ethyl-6-oxo-4-phenyl-1,6-dihydropyrimidin-1-yl)ethoxy]anilino}propanoate;

(−) Ethyl 2-{4-[2-(2-ethyl-6-oxo-4-phenyl-1,6-dihydropyrimidin-1-yl)ethoxy]anilino}propanoate;

(±) Ethyl 2-{4-[2-(2-ethyl-6-oxo-4-phenyl-1,6-dihydropyrimidin-1yl)ethoxy]anilino}-2-methyl propanoate;

(+) Ethyl 2-{4-[2-(2-ethyl-6-oxo-4-phenyl-1,6-dihydropyrimidin-1-yl)ethoxy]anilino}-2-methyl propanoate;

(−) Ethyl 2-{4-[2-(2-ethyl-6-oxo-4-phenyl-1,6-dihydropyrimidin-1-yl)ethoxy]anilino}-2-methyl propanoate;

(±) Ethyl 2-{4-[2-(2-ethyl-6-oxo-4-phenyl-1,6-dihydropyrimidin-1-yl)ethoxy]anilino}pentanoate;

(+) Ethyl 2-{4-[2-(2-ethyl-6-oxo-4-phenyl-1,6-dihydropyrimidin-1-yl)ethoxy]anilino}pentanoate;

(−) Ethyl 2-{4-[2-(2-ethyl-6-oxo-4-phenyl-1,6-dihydropyrimidin-1-yl)ethoxy]anilino}pentanoate;

(±) Ethyl 2-{4-[2-(2-ethyl-6-oxo-4-phenyl-1,6-dihydropyrimidin-1-yl)ethoxy](heptyl)anilino}propanoate;

(+) Ethyl 2-{4-[2-(2-ethyl-6-oxo-4-phenyl-1,6-dihydropyrimidin-1-yl)ethoxy](heptyl) anilino}propanoate;

(−) Ethyl 2-{4-[2-(2-ethyl-6-oxo-4-phenyl-1,6-dihydropyrimidin-1-yl)ethoxy](heptyl)anilino}propanoate;

(±) 2-[4-(2-Ethyl-6-oxo-4-phenyl-1,6-dihydropyrimidin-1-ylmethyl heptyl)carboxamido)phenyl sulfanyl]-3-methyl butanoic acid or its salts;

(+) 2-[4-(2-Ethyl-6-oxo-4-phenyl-1,6-dihydropyrimidin-1-ylmethyl heptyl)carboxamido)phenyl sulfanyl]-3-methyl butanoic acid or its salts;

(−) 2-[4-(2-Ethyl-6-oxo-4-phenyl-1,6-dihydropyrimidin-1-ylmethyl heptyl)carboxamido)phenyl sulfanyl]-3-methyl butanoic acid or its salts;

(±) 2-{4-[2-(2-Ethyl-6-oxo-4-phenyl-1,6-dihydropyrimidin-1-yl)ethylcarbamoyl]phenoxy}-2-methyl propanoic acid or its salts;

(+) 2-{4-[2-(2-Ethyl-6-oxo-4-phenyl-1,6-dihydropyrimidin-1-yl)ethylcarbamoyl]phenoxy}-2-methyl propanoic acid or its salts;

(−) 2-{4-[2-(2-Ethyl-6-oxo-4-phenyl-1,6-dihydropyrimidin-1-yl)ethylcarbamoyl]phenoxy}-2-methyl propanoic acid or its salts;

(±) 2-{4-[2-(2-Ethyl-6-oxo-4-phenyl-1,6-dihydropyrimidin-1yl)ethyl(heptyl)carbamoyl]phenoxy}-2-methyl propanoic acid or its salts;

(+) 2-{4-[2-(2-Ethyl-6-oxo-4-phenyl-1,6-dihydropyrimidin-1yl)ethyl(heptyl)carbamoyl]phenoxy}-2-methyl propanoic acid or its salts;

(−) 2-{4-[2-(2-Ethyl-6-oxo-4-phenyl-1,6-dihydropyrimidin-1yl)ethyl(heptyl)carbamoyl]phenoxy}-2-methyl propanoic acid or its salts;

(±) 2-[4-(2-Ethyl-6-oxo-4-phenyl-1,6-dihydropyrimidin-1-ylmethylcarboxamido)phenoxy]-2-methyl propanoic acid or its salts;

(+) 2-[4-(2-Ethyl-6-oxo-4-phenyl-1,6-dihydropyrimidin-1-ylmethylcarboxamido)phenoxy]-2-methyl propanoic acid or its salts;

(−) 2-[4-(2-Ethyl-6-oxo-4-phenyl-1,6-dihydropyrimidin-1-ylmethylcarboxamido)phenoxy]-2-methyl propanoic acid or its salts;

(±) 2-[4-(2-Ethyl-6-oxo-4-phenyl-1,6-dihydropyrimidin-1-ylmethyl(heptyl)carboxamido)phenoxy]-2-methyl propanoic acid or its salts;

(+) 2-[4-(2-Ethyl-6-oxo-4-phenyl-1,6-dihydropyrimidin-1-ylmethyl(heptyl)carboxamido)phenoxy]-2-methyl propanoic acid or its salts;

(−) 2-[4-(2-Ethyl-6-oxo-4-phenyl-1,6-dihydropyrimidin-1-ylmethyl(heptyl)carboxamido)phenoxy]-2-methyl propanoic acid or its salts;

(±) 2-{4-[2-(2-Ethyl-6-oxo-4-phenyl-1,6-dihydropyrimidin-1-yl)ethoxy]phenoxy}-2-methyl propanoic acid or its salts;

(+) 2-{4-[2-(2-Ethyl-6-oxo-4-phenyl-1,6-dihydropyrimidin-1-yl)ethoxy]phenoxy}-2-methyl propanoic acid or its salts;

(−) 2-{4-[2-(2-Ethyl-6-oxo-4-phenyl-1,6-dihydropyrimidin-1-yl)ethoxy]phenoxy}-2-methyl propanoic acid or its salts;

(±) 2-{4-[2-(2-Eethyl-6-oxo-4-phenyl-1,6-dihydropyrimidin-1-yl)ethoxy]phenoxy}pentanoic acid or its salts;

(+) 2-{4-[2-(2-Eethyl-6-oxo-4-phenyl-1,6-dihydropyrimidin-1-yl)ethoxy]phenoxy}pentanoic acid or its salts;

(−) 2-{4-[2-(2-Eethyl-6-oxo-4-phenyl-1,6-dihydropyrimidin-1-yl)ethoxy]phenoxy}pentanoic acid or its salts;

(±) 2-{4-[2-(2-Ethyl-6-oxo-4-phenyl-1,6-dihydropyrimidin-1-yl)ethoxy]phenoxy}-2-methyl butanoic acid or its salts;

(+) 2-{4-[2-(2-Ethyl-6-oxo-4-phenyl-1,6-dihydropyrimidin-1-yl)ethoxylphenoxy}-2-methyl butanoic acid or its salts;

(−) 2-{4-[2-(2-Ethyl-6-oxo-4-phenyl-1,6-dihydropyrimidin-1-yl)ethoxy]phenoxy}-2-methyl butanoic acid or its salts;

(±) 2-[4-(2-Ethyl-6-oxo-4-phenyl-1,6-dihydropyrimidin-1-ylmethyl(heptyl)carboxamido)phenyl sulfanyl]-2-methyl propanoic acid or its salts;

(+) 2-[4-(2-Ethyl-6-oxo-4-phenyl-1,6-dihydropyrimidin-1-ylmethyl(heptyl)carboxamido)phenyl sulfanyl]-2-methyl propanoic acid or its salts;

(−) 2-[4-(2-Ethyl-6-oxo-4-phenyl-1,6-dihydropyrimidin-1-ylmethyl(heptyl)carboxamido)phenyl sulfanyl]-2-methyl propanoic acid or its salts;

(±) 2-{4-[2-(2-Ethyl-6-oxo-4-phenyl-1,6-dihydropyrimidin-1-yl)ethoxy]anilino}propanoic acid or its salts;

(+) 2-{4-[2-(2-Ethyl-6-oxo-4-phenyl-1,6-dihydropyrimidin-1-yl)ethoxy]anilino}propanoic acid or its salts;

(−) 2-{4-[2-(2-Ethyl-6-oxo-4-phenyl-1,6-dihydropyrimidin-1-yl)ethoxy]anilino}propanoic acid or its salts;

(±) 2-[4-(2-Ethyl-6-oxo-4-phenyl-1,6-dihydropyrimidin-1-ylmethyl(heptyl)carboxamido)phenoxy]-2-methyl butanoic acid or its salts;

(+) 2-[4-(2-Ethyl-6-oxo-4-phenyl-1,6-dihydropyrimidin-1-ylmethyl(heptyl)carboxamido)phenoxy]-2-methyl butanoic acid or its salts;

(−) 2-[4-(2-Ethyl-6-oxo-4-phenyl-1,6-dihydropyrimidin-1-ylmethyl(heptyl)carboxamido)phenoxy]-2-methyl butanoic acid or its salts;

(±) 2-[4-(2-Ethyl-6-oxo-4-phenyl-1,6-dihydropyrimidin-1-ylmethyl(heptyl)carboxamido)phenoxy]methyl pentanoic acid or its salts;

(+) 2-[4-(2-Ethyl-6-oxo-4-phenyl-1,6-dihydropyrimidin-1-ylmethyl(heptyl)carboxamido)phenoxy]methyl pentanoic acid or its salts;

(−) 2-[4-(2-Ethyl-6-oxo-4-phenyl-1,6-dihydropyrimidin-1-ylmethyl(heptyl)carboxamido)phenoxy]methyl pentanoic acid or its salts;

(±) 2-{4-[2-(2-Ethyl-6-oxo-4-phenyl-1,6-dihydropyrimidin-1-yl)ethoxy]anilino}-2-methyl propanoic acid or its salts;

(+) 2-{-[2-(2-Ethyl-6-oxo-4-phenyl-1,6-dihydropyrimidin-1-yl)ethoxy]anilino}-2-methyl propanoic acid or its salts;

(−) 2-{4-[2-(2-Ethyl-6-oxo-4-phenyl-1,6-dihydropyrimidin-1-yl)ethoxy]anilino}-2-methyl propanoic acid or its salts;

(±) 2-{4-[2-(2-Ethyl-6-oxo-4-phenyl-1,6-dihydropyrimidin-1-yl)ethoxy]anilino}pentanoic acid or its salts;

(+) 2-{4-[2-(2-Ethyl-6-oxo-4-phenyl-1,6-dihydropyrimidin-1-yl)ethoxy]anilino}pentanoic acid or its salts;

(−) 2-{4-[2-(2-Ethyl-6-oxo-4-phenyl-1,6-dihydropyrimidin-1-yl)ethoxy]anilino}pentanoic acid or its salts;

(±) 2-[4-(2-Ethyl-6-oxo-4-phenyl-1,6-dihydropyrimidin-1-ylmethyl(heptyl)carboxamido)phenyl sulfanyl]pentanoic acid or its salts;

(+) 2-[4-(2-Ethyl-6-oxo-4-phenyl-1,6-dihydropyrimidin-1-ylmethyl(heptyl)carboxamido)phenyl sulfanyl]pentanoic acid or its salts;

(−) 2-[4-(2-Ethyl-6-oxo-4-phenyl-1,6-dihydropyrimidin-1-ylmethyl(heptyl)carboxamido)phenyl sulfanyl]pentanoic acid or its salts;

(±) 2-{4-[2-(2-Ethyl-6-oxo-4-phenyl-1,6-dihydropyrimidin-1-yl)ethylsulfanyl]phenoxy}acetic acid or its salts;

(+) 2-{4-[2-(2-Ethyl-6-oxo-4-phenyl-1,6-dihydropyrimidin-1-yl)ethylsulfanyl]phenoxy}acetic acid or its salts;

(−) 2-{4-[2-(2-Ethyl-6-oxo-4-phenyl-1,6-dihydropyrimidin-1-yl)ethylsulfanyl]phenoxy}acetic acid or its salts;

(±) 2-[4-(2Ethyl-6-oxo-4-phenyl-1,6-dihydropyrimidin-1-ylmethyl(heptyl)carboxamido)phenyl sulfanyl]butanoic acid or its salts;

(+) 2-[4-(2-Ethyl-6-oxo-4-phenyl-1,6-dihydropyrimidin-1-ylmethyl(heptyl)carboxamido)phenyl sulfanyl]butanoic acid or its salts;

(−) 2-[4-(2-Ethyl-6-oxo-4-phenyl-1,6-dihydropyrimidin-1-ylmethyl(heptyl)carboxamido)phenyl sulfanyl]butanoic acid or its salts;

(±) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(+) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(−) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(±) 2-{4-[2-(2-Ethyl-6-oxo-4-phenyl-1,6-dihydropyrimidin-1-yl)ethoxy]phenylsulfanyl]-2-methyl butanoic acid or its salts;

(+) 2-{4-[2-(2-Ethyl-6-oxo-4-phenyl-1,6-dihydropyrimidin-1-yl)ethoxy]phenylsulfanyl}-2-methyl butanoic acid or its salts;

(−) 2-{4-[2-(2-Ethyl-6-oxo-4-phenyl-1,6-dihydropyrimidin-1-yl)ethoxy]phenylsulfanyl}-2-methyl butanoic acid or its salts;

(±) 2-[4-(2-Ethyl-6-oxo-4-phenyl-1,6-dihydropyrimidin-1-ylmethylcarboxamido)phenyl sulfanyl]-3-methyl butanoic acid or its salts;

(+) 2-[4-(2-Ethyl-6-oxo-4-phenyl-1,6-dihydropyrimidin-1-ylmethylcarboxamido)phenyl sulfanyl]-3-methyl butanoic acid or its salts;

(−) 2-[4-(2-Ethyl-6-oxo-4-phenyl-1,6-dihydropyrimidin-1-ylmethylcarboxamido)phenyl sulfanyl]-3-methyl butanoic acid or its salts;

(±) 2-{4-[2-(2-Ethyl-6-oxo-4-phenyl-1,6-dihydropyrimidin-1-yl)ethylamino]phenyl sulfanyl}butanoic acid or its salts;

(+) 2-{4-[2-(2-Ethyl-6-oxo-4-phenyl-1,6-dihydropyrimidin-1yl)ethylamino]phenyl sulfanyl}butanoic acid or its salts;

(−) 2-{4-[2-(2-Ethyl-6-oxo-4-phenyl-1,6-dihydropyrimidin-1-yl)ethylamino]phenyl sulfanyl}butanoic acid or its salts;

(±) 2-{4-[2-(2-Ethyl-6-oxo-4-phenyl-1,6-dihydropyrimidin-1-yl)ethylamino]phenylsulfanyl}-4-methyl pentanoic acid or its salts;

(+) 2-{4-[2-(2-Ethyl-6-oxo-4-phenyl-1,6-dihydropyrimidin-1-yl)ethylamino]phenylsulfanyl}-4-methyl pentanoic acid or its salts;

(−) 2-{4-[2-(2-Ethyl-6-oxo-4-phenyl-1,6-dihydropyrimidin-1-yl)ethylamino]phenylsulfanyl}-4-methyl pentanoic acid or its salts;

(±) 2-{4-[2-(2-Ethyl-6-oxo-4-phenyl-1,6-dihydropyrimidin-1-yl)ethylamino]phenylsulfanyl}-3-methyl butanoic acid or its salts;

(+) 2-{4-[2-(2-Ethyl-6-oxo-4-phenyl-1,6-dihydropyrimidin-1-yl)ethylamino]phenylsulfanyl}-3-methyl butanoic acid or its salts;

(−) 2-{4-[2-(2-Ethyl-6-oxo-4-phenyl-1,6-dihydropyrimidin-1-yl)ethylamino]phenylsulfanyl}-3-methyl butanoic acid or its salts;

According to another embodiment of the present invention there is provided a process for the preparation of the compound of formula (I) where all the symbols are as defined earlier which comprises, reacting a compound of formula (IIIa)

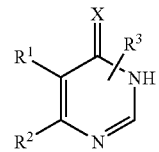

(IIIa)

where $R^1$, $R^2$, $R^3$ and X are as defined above with a compound of general formula (IIIb)

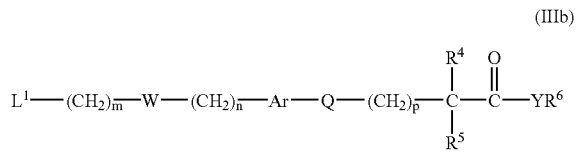

(IIIb)

where $L^1$ is a leaving group and all other symbols are as defined earlier to produce a compound of formula (I) where all symbols are as defined earlier.

The leaving group represented by $L^1$ in formula (IIIb) may be halogen atom like chlorine, bromine or iodine or other leaving groups such as p-toluenesulfonate, methanesulfonate, trifluoromethanesulfonate and the like, The reaction of compound of formula (IIIa) with a compound of formula (IIIb) where all symbols are as defined earlier to produce a compound of formula (I) where all symbols are as defined earlier may be carried out in the presence of solvents such as DMSO, DMF, DME, THF, dioxane, ether and the like or a combination thereof The reaction may be carried out in an inert atmosphere which may be maintained by using inert gases such as $N_2$, Ar, He and the like. The reaction may be effected in the presence of a base such as alkalis like sodium hydroxide, potassium hydroxide, alkali metal carbonates like sodium carbonate or potassium carbonate; alkali metal hydrides such as sodium hydride or potassium hydride; organometallic bases like n-butyl lithium; alkali metal amides like sodamide or mixtures thereof. The amount of base may range from 1 to 5 equivalents, based on the amount of the compound of formula (IIIa), preferably the amount of base ranges from 1 to 3 equivalents. The reaction may be carried out at a temperature in the range of 0° C. to 150° C., preferably at a temperature in the range of 15° C. to 100° C. The duration of the reaction may range from 0.25 to 24 hours, preferably from 0.25 to 12 hours.

In yet another embodiment of the present invention, there is provided a process for the preparation of compound of formula (I) where all the symbols are as defined earlier, which comprises, reacting a compound of formula (IIIc)

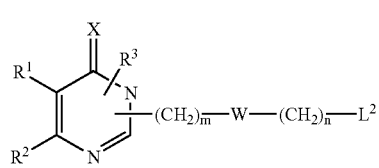

where $L^2$ represents a halogen atom such as Cl, Br or I, W represents C=O and all other symbols are as defined earlier with a compound of formula (IIId)

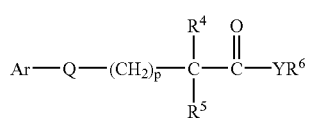

where all symbols are as defined earlier.

The reaction of the compound of the formula (IIIc) with a compound of formula (IIId) where all symbols are as defined earlier to produce a compound of formula (I) defined above may be carried out in the presence of solvents such as dioxane, DME, carbon disulfide, nitrobenzene and the like or mixtures thereof. The reaction may be carried out in the presence of a catalyst such as $FeCl_3$, $AlCl_3$, $I_2$, $ZnCl_2$, iron and the like. The reaction may be carried out in inert atmosphere which may be maintained by using inert gases such as $N_2$, Ar, He and the like. The reaction temperature may range from 25° C. to 180° C. The reaction time may range from 1 to 24 hours.

In still another embodiment of the present invention there is provided a process for the preparation of compound of formula (I) defined above which comprises, reacting a compound of formula (IIIe)

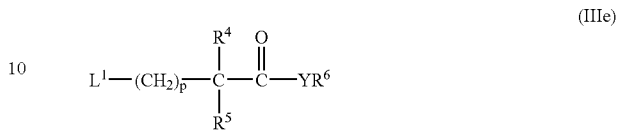

where $L^1$ is a leaving group and all other symbols are as defined earlier with a compound of formula (IIIf)

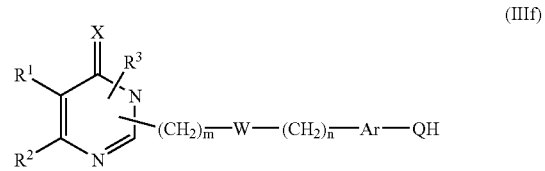

where all symbols are as defined earlier.

The leaving represented by $L^1$ in formula (IIIe) may be halogen atom like chlorine, bromine or iodine or other leaving groups such as p-toluenesulfonate, methanesulfonate, trifluoromethanesulfonate and the like.

The reaction of compound of formula (IIIe) with compound of formula (IIIf) to produce a compound of the formula (I) defined above may be carried out in the presence of aprotic solvents such as THF, DMF, DMSO, DME and the like or mixtures thereof. The reaction may be carried out in an inert atmosphere which may be maintained by using inert gases such as $N_2$, Ar, He and the like. The reaction may be effected in the presence of a base such as $K_2CO_3$, $Na_2CO_3$ or NaH or mixtures thereof. Acetone may be used as solvent when $Na_2CO_3$ or $K_2CO_3$ is used as a base. The reaction temperature may range from 0° C.-120° C., preferably at a temperature in the range of 30° C. -100° C. The duration of the reaction may range from 1 to 24 hours, preferably from 2 to 12 hours.

In yet another embodiment of the present invention, there is provided a process for the preparation of compound of formula (I), where W represents $NR^7$ and all other symbols are as defined above, which comprises, reacting the compound of formula (IIIg)

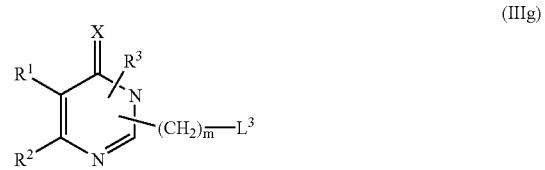

where L³ is a leaving group such as halogen atom, p-toluenesulfonate, methanesulfonate, trifluoromethanesulfonate and the like, or L³ represents COOH, COCl, with compound of formula (IIIh)

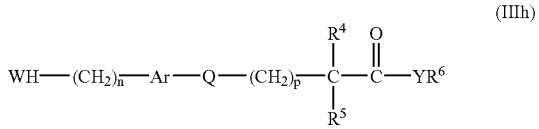
(IIIh)

where all symbols are as defined above.

The reaction of compound of formula (IIIg) with compound of formula (IIIh) where all symbols are as defined earlier to produce a compound of the formula (I) defined above may be carried out in the presence of aprotic solvents such as THF, DMF, DMSO, DME, DCM, CHCl₃ and the like or mixtures thereof. The reaction may be carried out in an inert atmosphere that may be maintained by using inert gases such as $N_2$, Ar, He and the like. The reaction may be effected in the presence of a base such as $K_2CO_3$, $Na_2CO_3$ or NaH, KH, triethyl amine and the like or mixtures thereof or diisopropyl carbodiimide, 1-(3-dimethylaminopropyl)-3-ethyl carbodiimide (EDC), diisopropyl azodicarboxylate (DIAD), DEAD when L³ is a COOH or COCl. The reaction temperature may range from 0° C. -120° C., preferably at a temperature in the range of 25° C. -100° C. The duration of the reaction may range from 1 to 72 hours, preferably from 2 to 24 hours.

In yet another embodiment of the present invention, there is provided a novel intermediate of formula (IIIh)

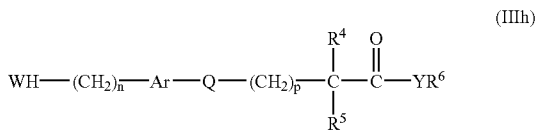
(IIIh)

wherein n is from 0-4; W represents $NR^7$, where $R^7$ represents hydrogen, $(C_1-C_{12})$ alkyl, aryl, or aralkyl group; Ar represents substituted or unsubstituted divalent single or fused aromatic or heterocyclic group; $R^4$ and $R^5$ may be same or different and represent hydrogen, hydroxy, alkoxy, halogen or substituted or unsubstituted groups selected from $(C_1-C_{12})$alkyl, aralkyl or heteroaralkyl groups; $R^6$ may be hydrogen or substituted or unsubstituted groups selected from $(C_1-C_{12})$alkyl, cycloalkyl, aryl, aralkyl, heterocyclyl, heteroaryl or heteroaralkyl groups; Y represents oxygen or $NR^8$, where $R^8$ represents hydrogen or substituted or unsubstituted groups selected from alkyl, aryl, hydroxyalkyl, aralkyl heterocyclyl, heteroaryl, or heteroaralkyl groups; $R^6$ and $R^8$ together may form a substituted or unsubstituted 5 or 6 membered cyclic structure containing carbon atoms, one or two nitrogen atoms and may optionally contain one or more heteroatoms selected from oxygen, or sulfur; Q represents O, S, SO, $SO_2$ or $NR^9$ wherein $R^9$ represents hydrogen, substituted or unsubstituted groups selected from $(C_1-C_{12})$alkyl, cycloalkyl, aryl, hydroxyalkyl, aralkyl, heterocyclyl, heteroaryl, or heteroaralkyl groups; and p is an integer of 0 or 1.

The compound of formula (IIIh) where all symbols are as defined above may be prepared by reacting a compound of formula (IIIi)

WH—(CH₂)ₙ—Ar—QH (IIIi)

where all symbols are as defined above with compound of formula (IIIj)

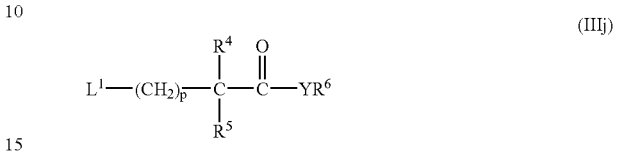
(IIIj)

where L¹ is a leaving group and all other symbols are as defined above

The reaction of compound of formula (IIIi) with a compound of formula (IIIj) to produce a compound of the formula (IIIh) may be carried out in the presence of solvents such as THF, DMF, DMSO, DME, acetonitrile and the like or mixtures thereof. The reaction may be effected in the presence of a base such as $K_2CO_3$, $Na_2CO_3$, NaOH, KOH, NaOEt, K⁺BuO⁻, NaH and the like. The reaction temperature may range from 0° C.-120° C., preferably at a temperature in the range of 30° C.-100° C. The duration of the reaction may range from 1 to 24 hours, preferably from 2 to 12 hours.

It is appreciated that in any of the above mentioned reactions, any reactive group in the substrate molecule may be protected according to conventional chemical practice. Suitable protecting groups in any of the above mentioned reactions are those used conventionally in the art. The methods of formation and removal of such protecting groups are those conventional methods appropriate to the molecule being protected.

The pharmaceutically acceptable salts are prepared by reacting the compound of formula (I) with 1 to 4 equivalents of a base such as sodium hydroxide, sodium methoxide, sodium hydride, potassium hydroxide, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixtures of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley Interscience, 1981). More specifically the compound of formula (I) where $YR^6$ represents OH may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (I) may be prepared by hydrolyzing the pure diastereomeric amide.

Various polymorphs of a compound of general formula (I) forming part of this invention may be prepared by crystallization of compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides a pharmaceutical composition, containing the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like, useful for the treatment and/or prophylaxis of diseases such as hypertension, coronary heart disease, atherosclerosis, stroke, peripheral vascular diseases and related disorders. These compounds are useful for the treatment of familial hypercholesterolemia, hypertriglyceridemia, lowering of atherogenic lipoproteins, VLDL and LDL. The compounds of the present invention can be used for the treatment of certain renal diseases including glomerulonephritis, glomerulosclerosis, nephrotic syndrome, hypertensive nephrosclerosis, nephropathy. The compounds of general formula (I) are also useful for the treatment and or prophylaxis of insulin resistance (type II diabetes), leptin resistance, impaired glucose tolerance, dyslipidemia, disorders related to syndrome X such as hypertension, obesity, insulin resistance, coronary heart disease, and other cardiovascular disorders. These compounds may also be useful as aldose reductase inhibitors, for improving cognitive functions in dementia, as inflammatory agents, treating diabetic complications, disorders related to endothelial cell activation, psoriasis, polycystic ovarian syndrome (PCOS), inflammatory bowel diseases, osteoporosis, myotonic dystrophy, pancreatitis, retinopathy, arteriosclerosis, xanthoma and for the treatment of cancer. The compounds of the present invention are useful in the treatment and/or prophylaxis of the above said diseases in combination/concomittant with one or more HMG CoA reductase inhibitors, hypolipidemic/hypolipoproteinemic agents such as ezetimibe, orlistat, fibrate, fibric acid derivatives, nicotinic acid, cholestyramine, colestipol, probucol or their combination. The compounds of the present invention in combination with HMG CoA reductase inhibitors, hypolipidemic/hypolipoproteinemic agents can be administered together or within such a period to act synergistically or additively. The HMG CoA reductase inhibitors may be selected from those used for the treatment or prevention of hyperlipidemia such as lovastatin, provastatin, simvastatin, fluvastatin, atorvastatin, cerivastatin and their analogs thereof. Suitable fibric acid derivative may be gemfibrozil, clofibrate, fenofibrate, ciprofibrate, benzafibrate and their analogs thereof.

The present invention also provides a pharmaceutical compositions, containing one or more of the compounds of the general formula (I) as defined above, their derivatives, their analogs, their tautomeric forms, their stereoisomers, their polymorphs, their pharmaceutically acceptable salts or their pharmaceutically acceptable solvates in combination with the usual pharmaceutically employed carriers, diluents and the like.

The present invention also provides a pharmaceutical composition, containing one or more of the compounds of the general formula (I) as defined above, their derivatives, their analogs, their tautomeric forms, their stereoisomers, their polymorphs, their pharmaceutically acceptable salts or their pharmaceutically acceptable solvates and one or more HMG CoA reductase inhibitors, hypolipidemic/hypolipoproteinemic agents such as fibric acid derivatives, fibrates, nicotinic acid, cholestyramine, colestipol, probucol, ezetimibe and orlistat in combination with the usual pharmaceutically employed carriers, diluents and the like.

The pharmaceutical composition of this invention may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. The injectable solutions prepared in this manner can then be administered intravenously, intraperitoneally, subcutaneously, or intramuscularly, with intramuscular administration being preferred in humans.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 50 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

The invention is explained in detail in the examples given below which are provided by way of illustration only and therefore should not be construed to limit the scope of the invention.

Preparation 1

Ethyl 2-methyl-2-(4-nitrophenyloxy)propanoate

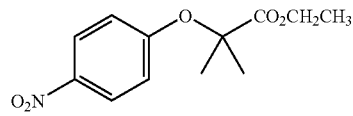

To a stirred solution of 4-Nitro phenol (2 g, 14.0 mmol) in ethanol (40 ml) was added potassium hydroxide (2.4 g) and stirred for 10 min. To this ethyl 2-bromo isobutyrate (4.2 g, 21 mmol) was added and the mixture heated to reflux for 15 h. The mixture, was filtered, washed with EtOAc and the combined filtrates were added to water (100 ml) and extracted with EtOAc. The combined organic layers were washed with water, 50% sodium carbonate solution and then with brine. The organic layer was dried over $Na_2SO_4$ and evaporated under reduced pressure to give the title compound as a thick gummy mass (2 g, 56%).

$^1$H NMR (200 MHz, $CDCl_3$): δ 8.13 (d, J=9.28 Hz, 2H), 6.83 (d, J=9.28 Hz, 2H), 4.21 (q, J=4.21 Hz, 2H), 1.92 (s, 6H), 1.21 (t, 4.21 Hz, 3H).

The compounds given in Table I were also prepared using a similar method described in preparation 1.

TABLE I

| Preparation No. | Structure | mp/Nature | Yield | $^1$H NMR ($CDCl_3$): δ |
|---|---|---|---|---|
| 2 | (4-nitrophenyloxy ethyl propanoate derivative) | Liquid | 30% | 8.14 (d, J = 9.28 Hz, 2H), 6.85 (d, J = 9.28 Hz, 2H), 4.23 (q, J = 7.33 Hz, 2H), 2.11-1.96 (m, 2H), 1.22 (s, 3H), 1.26 (t, J = 6.84 Hz, 3H), 0.98 (t, J = 7.33 Hz, 3H). |
| 3 | (4-nitrophenyloxy ethyl butanoate derivative) | Gummy liquid | 92% | 8.20 (d, J = 9.28 Hz, 2H), 6.93 (d, J = 9.28 Hz, 2H), 4.72 (t, J = 6.35 Hz, 1H), 4.23 (q, J = 6.84 Hz, 2H), 2.10-1.90 (m, 2H), 1.65-1.50 (m, 2H), 1.26 (t, J = 6.84 Hz, 3H), 0.99 (t, J = 7.33 Hz, 3H). |
| 4 | (4-aminophenyloxy ethyl propanoate derivative) | 70–72° C. | 50% | 6.78 (d, J = 8.79 Hz, 2H), 6.68 (d, J = 8.79 Hz, 2H), 4.24 (q, J = 6.84 Hz, 2H), 1.52 (s, 6H), 1.27 (t, J = 6.84 Hz, 3H). |
| 5 | (4-hydroxyphenyloxy ethyl propanoate derivative) | 68° C. | 26% | 6.79 (d, J = 9.28 Hz, 2H), 6.69 (d, J = 9.28 Hz, 2H), 4.71 (bs, 1H, $D_2O$ exchangeable), 4.25 (q, J = 7.33 Hz, 2H), 1.94 (q, J = 7.32 Hz, 2H), 1.42 (s, 3H), 1.28 (t, J = 7.33 Hz, 3H), 0.98 (t, J = 7.32 Hz, 3H). |
| 6 | (4-carboxyphenyloxy ethyl propanoate derivative) | | | 8.00 (d, J = 8.79 Hz, 2H), 8.79 (d, J = 8.79 Hz, 2H), 4.23 (q, J = 7.33 Hz, 2H), 1.66 (s, 6H), 1.22 (t, J = 7.33 Hz, 3H). |

Preparation 7

Ethyl-2-methyl-2-(4-amino phenyloxy)propanoate

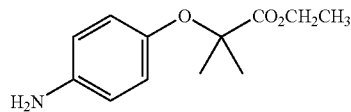

The title compound (1.2 g, 68%) was prepared from ethyl 2-methyl-2-(4-nitrophenyloxy)propanoate (2 g, 7.9 mmol) by hydrogenation with 10% Pd/C (1 g) in methanol at 50 psi and room temperature for 2 h.

$^1$H NMR (CDCl$_3$, 200 MHz): δ 6.75 (d, J=8.30 Hz, 2H), 6.57 (d, J=8.30 Hz, 2H), 4.23 (q, J=6.84 Hz, 2H), 1.52 (s,6H), 1.29 (t, J=6.84 Hz, 3H).

The compounds given in Table II were also prepared using a similar method described in preparation 7.

Preparation 7

Ethyl-2-methyl2-(4-amino phenyloxy)propanoate

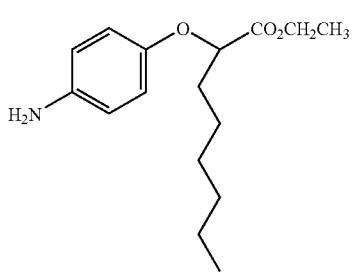

To suspension of sodium hydride (0.458 g, 19.08 mmol) in dry DMF (10 ml) p-aminophenol (1 g, 9.174 mmol) in dry DMF (10 ml) was added at 0° C. and stirred at that temperature for 15 min. To this ethyl-2-bromo octanoate (3.454 g, 13.7 6 mmol) was added and stirred the mixture at room temperature for 12 h. The reaction mixture was quenched with ice and added water (100 ml) and extracted with EtOAc (50×3 mL). The combined extracts were washed with water, brine and dried over Na$_2$SO$_4$ to give the title compound (0.4 g, 16%).

$^1$H NMR (CDCl$_3$, 200 MHz): δ 6.74 (d, J=8.79 Hz, 2H), 6.62 (d, J=8.79 Hz, 2H), 4.46 (t, J=6.35 Hz, 1H), 4.20 (q, J=6.83 Hz, 2H), 3.48 (bs, 2H, D$_2$O exchangeable), 2.00-1.82 (m, 2H), 1.60-1.21 (m, 11H), 0.89 (t, J=5.86 Hz, 3H).

The compounds given in Table III were also prepared using a similar method described in preparation 10.

TABLE II

| Preparation No. | Structure | mp/Nature | Yield | $^1$H NMR (CDCl$_3$): δ |
|---|---|---|---|---|
| 8 | 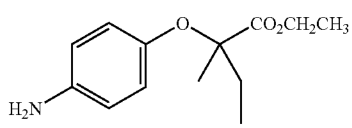 | Liquid | 79% | 6.75 (d, J = 8.79 Hz, 2H), 6.58 (d, J = 8.79 Hz, 2H), 4.25 (q, J = 6.84 Hz, 2H), 1.93 (q, J = 7.33 Hz, 2H), 1.41 (s, 3H), 1.30 (t, J = 6.84 Hz, 3H), 0.98 (t, J = 7.33 Hz, 3H). |
| 9 | 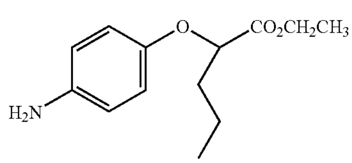 | Liquid | 97% | 6.76 (d, J = 8.79 Hz, 2H), 6.69 (d, J = 8.79 Hz, 2H), 4.48 (t, J = 5.86 Hz, 1H), 4.20 (q, J = 6.84 Hz, 2H), 3.78 (bs, 2H, D$_2$O exchangeable), 1.96-1.83 (m, 2H), 1.61-1.44 (m, 2H), 1.25 (t, J = 6.84 Hz, 3H), 0.97 (t, J = 7.33 Hz, 3H). |

TABLE III

| Preparation No. | Structure | mp/Nature | Yield | $^1$H NMR (CDCl$_3$): δ |
|---|---|---|---|---|
| 11 | H$_2$N-C$_6$H$_4$-S-C(CH$_3$)$_2$-CO$_2$CH$_2$CH$_3$ | Gummy oil | 40% | 6.655 (d, J = 9.28 Hz, 2H), 6.55 (d, J = 9.28 Hz, 2H), 4.21 (q, J = 6.83 Hz, 2H), 1.50 (s, 6H), 1.27 (t, J = 6.83 Hz, 3H). |
| 12 | H$_2$N-C$_6$H$_4$-S-CH(Pr)-CO$_2$CH$_2$CH$_3$ | Gummy | 25% | 7.28 (d, J = 8.30 Hz, 2H), 6.61 (d, J = 8.30 Hz, 2H), 4.11 (q, J = 7.33 Hz, 2H), 3.76 (bs, 2H, D$_2$O exchangeable), 3.44 (t, J = 7.33 Hz, 1H), 1.91-1.57 (m, 2H), 1.49-1.32 (m, 2H), 1.20 (t, 7.33 Hz, 3H), 0.921 (t, 7.33 Hz, 3H). |
| 13 | H$_2$N-C$_6$H$_4$-S-CH(iPr)-CO$_2$CH$_2$CH$_3$ | Gummy | 69% | 7.27 (d, J = 8.30 Hz, 2H), 6.59 (d, J = 8.30 Hz, 2H), 3.77 (bs, 2H, D$_2$O exchangeable), 3.19(d, J = 8.79 Hz, 1H), 2.10-1.95 (m, 1H), 1.22-1.12 (m, 6H), 0.99 (d, J = 6.35 Hz, 3H). |
| 14 | H$_2$N-C$_6$H$_4$-S-CH(Et)-CO$_2$CH$_2$CH$_3$ | Gummy | 68% | 7.26 (d, J = 8.30 Hz, 2H), 6.59 (d, J = 8.30 Hz, 2H), 4.10 (q, J = 7.32 Hz, 2H), 3.78 (bs, 2H, D$_2$O exchangeable), 3.34 (t, J = Hz, 1H) 1.90-1.63 (m, 2H), 1.19 (t, J = 7.32 Hz, 3H), 0.99 (t, J = 7.53 Hz, 3H). |
| 15 | H$_2$N-C$_6$H$_4$-S-CH(iBu)-CO$_2$CH$_2$CH$_3$ | Gummy | 72% | 7.26 (d, J = 8.30 Hz, 2H), 6.60 (d, J = 8.30 Hz, 2H), 4.08 (q, J = 7.33 Hz, 2H), 3.80 (bs, 2H, D$_2$O exchangeable), 3.50 (t, J = 6.84 Hz, 1H), 1.81-1.43 J = 7.33 Hz, 3H), 0.91 (d, J = 1.95 Hz, 3H), 0.88 (d, J = 1.95 Hz, 3H). |
| 16 | HO-C$_6$H$_4$-S-CH(iPr)-CO$_2$Et | Gummy | 56% | 7032 (d, J = 8.79 Hz, 2H), 6.70 (d, J = 8.79 Hz, 2H), 6.09 (S, 1H, D$_2$O exchangeable) 4.12 (q, J = 7.32 Hz, 2H), 3.25 (d, J = 9.27 Hz, 2H), 2.10-1.95 (m,1H), 1.29-1.15 (m,6H), 1.00 (d, J = 6.84 Hz, 3H). |

Preparation 17

Ethyl-3-methyl-2-(4-heptylamino phenylthio)butanoate

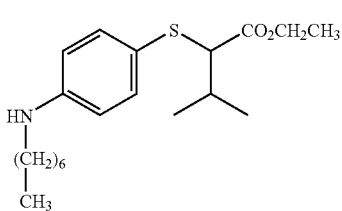

To ethyl-3-methyl-2-(4-amino phenylthio)octanoate obtained from preparation 13, (2.57 g, 0.01015 mol) was added K$_2$CO$_3$ (2.8 g, 0.02 mol), tetrabutyl ammonium bromide (TBAB) (3.27 g, 0.01 mol), heptylbromide (1.756 ml, 0.011 mol) in toluene (50 ml) and heated at 100° C. for 16 h. The reaction mixture was cooled to room temperature, filtered and washed with EtOAc (100 ml). The combined organic layers were washed with water, brine and dried over Na$_2$SO$_4$ and concentrated under reduced pressure. The crude compound was purified by column chromatography, using 1:2 EtOAc:pet. ether as eluent to give the title compound (2.4 g, 67.4%).

$^1$H NMR (CDCl$_3$, 200 MHz): δ 7.28 (d, J=8.79 Hz, 2H), 6.49 (d, J=8.79 Hz, 2H), 4.09 (q, 7.32 Hz, 2H), 3.74 (bs, 1H, D$_2$O exchangeable), 3.18 (d, J=9.28 Hz, 1H), 3.08 (t, J=7.32

Hz, 2H), 2.13-1.95 (m, 1H), 1.60-1.51 (m, 2H), 1.31-1.13 (m, 14H), 0.99 (d, J=6.83 Hz, 3H), 0.89 (t, J=6.84 Hz, 3H).

The compounds given in Table IV were also prepared using a similar method described in Preparation 17.

To a suspension of NaH (1.25 g, 0.04 mol) in dry DMF (100 mL) 2-ethyl-4-phenyl-4(3H)pyrimidinone (4 g, 0.02 mol) was added at 0° C. and stirred for 30 min. To this anhydrous LiBr (2.5 g, 0.024 mol) was added at 0° C. and

TABLE IV

| Preparation No. | Structure | mp/ Nature | Yield | $^1$H NMR (CDCl$_3$): δ |
|---|---|---|---|---|
| 18 | 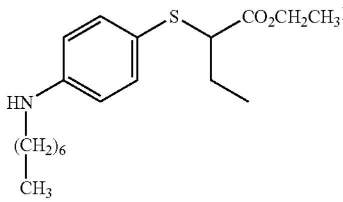 | Liquid | 50% | 7.28 (d, J = 7.3 Hz, 2H), 6.50 9d, J = 7.30 Hz, 2H), 4.11 (q, J = 7.3 Hz, 2H), 3.33 (t, J = 6.83 Hz, 1H), 3.08 (t, J = 6.84 Hz, 2H), 1.87-1.57 (m, 4H), 1.4-1.2 (m, 11H), .99 (t, J = 7.33 Hz, 3H), 0.89 (t, J = 6.35 Hz, 3H). |
| 19 | 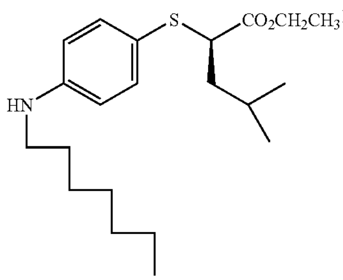 | Liquid | 33% | 7.26 9(d, J = 8.3 Hz, 2H), 6.49 (d, J = 8.3 Hz, 2H), 4.08 (q, J = 6.84 Hz, 2H), 3.47 (t, J = 7.84 Hz, 1H), 3.08 (t, J = 6.84, 2H), 1.80-1.45 (m, 6H), 1.40-1.10 (m, 11H), 1.00-0.89 (m, 9H). |
| 20 | 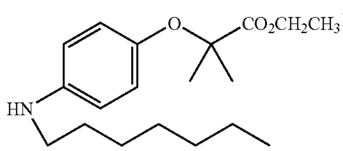 | Liquid | 56% | 6.77 (d, J = 8.79 Hz, 2H), 6.48 (d, J = 8.79 Hz, 2H), 4.23 (q, J = 7.33 Hz, 2H), 3.04 (t, J = 6.83 Hz, 2H), 1.6-1.50 (m, 19H), 0.88 (t, J = 6.35 Hz, 3H). |
| 21 | 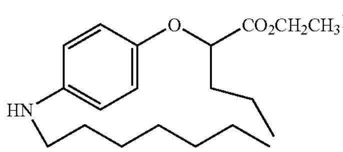 | Liquid | 32% | 6.77 (d, J = 8.79 Hz, 2H), 6.55 (d, J = 8.79 Hz, 2H), 4.46 (t, J = 6.45 Hz, 1H), 4.20 (q, J = 6.8 Hz, 2H), 3.04 (t, J = 7.04 Hz, 2H), 1.95-1.82 (m, 2H), 1.57-1.45 (m, 4H), 1.42-1.2 (m, 11H), 1.05-0.8 (m, 6H). |
| 22 | 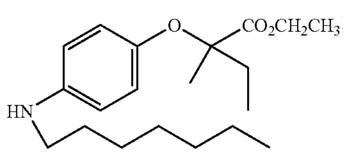 | Liquid | 66% | 6.77 (d, J = 8.79 Hz, 2H), 6.48 (d, J = 8.79 Hz, 2H), 4.24 (q, J = 7.32 Hz, 2H), 3.04 (t, J = 6.83 Hz, 2H), 1.92 (q, J = 7.33 Hz, 2H), 1.60-1.40 (m, 4H), 1.98-1.15 (m, 11H), 0.97 (t, J = 7.33 Hz, 3H), 0.88 (t, J = 6.35 Hz, 3H). |

Preparation 23

2-(2-Ethyl-6-oxo-4-phenyl-1,6-dihydro-1-pyrimidinyl)acetic acid

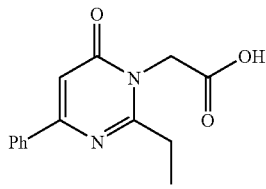

stirred at RT for further 10 min. Ethyl bromoacetate (4 g, 0.024 mol) was added and the mixture was heated to 80° C. for 16 h. The reaction mixture was quenched with ice-water, extracted with EtOAc and the combined layers were washed with water, brine and dried over Na$_2$SO$_4$ to get 'O' and 'N' alkyl mixtures (a mixture of O-alkylated product and N-alkalyted product), which were separated by column chromatography using 30% EtOAc:pet. ether as eluent to yield 'N' alkylated compound, ethyl-2-(2-ethyl-6-oxo-4-phenyl-1,6-dihydro-1-pyrimidinyl)acetate (2.8 g, 49%) as a solid. The N-alkylated compound as hydrolyzed using aq. NaOH (2.8 g, 5 ml of H$_2$O) in methanol (15 ml) at RT for 2 h to give the title compound as white solid (mp: 201-203° C., (2.3 g, 91%).

¹H NMR (CDCl₃+CD₃OD, 200 MHz): δ 8.04-7.99 (m, 2H), 7.68-7.40 (m, 3H), 6.80 (s, 1H), 4.87 (s, 2H), 4.82 (q, J=7.32 Hz, 2H), 1.40 (t, J=7.32 Hz, 3H).

Preparation 24

2-(2-Ethyl-6-oxo-4-phenyl-1,6-dihydro-1-pyrimidinyl)ethylamine

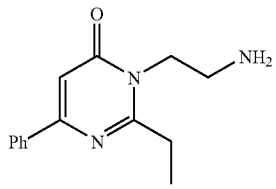

To a suspension of 60% NaH (0.625 g, 0.026 mol) in DMF (30 mL), 2-ethyl-4-phenyl-4(3H)pyrimidinone (2 g, 0.01 mol) was added at 0° C. and stirred at RT for 30 min. The reaction mixture was cooled to 0° C. and added LiBr (1.7 g, 0.0195 mol) and the temperature was raised to RT and added 2-benzyloxycarbonyl amino ethylbromide (2.58 g, 0.01 mol) and tetrabutyl ammonium bromide (3.3 g, 0.01 mol), and heated at 80° C. for 16 h. The reaction mixture was quenched with ice-water, extracted with EtOAC, washed with water, brine and dried over Na₂SO₄, concentrated the solvent to give 2-(2-ethyl-6-oxo-4-phenyl-1,6-dihydro-1-pyrimidinyl)N-benzyloxycarbonyl aminoethyl bromide (1.1 g, 30%). This compound was hydrogenated over 10% Pd/C with ethanol as the solvent at 1 atm pressure of H₂ gas, filtered and evaporated the solvent to give the title compound (0.48 g, 98%) as a liquid.

¹H NMR (CDCl₃, 200 MHz): δ 8.08-8.037 (m, 2H), 7.48-7.32 (m, 3H), 6.81 (s, 1H), 4.17 (t, J=7.32 Hz, 2H), 3.03-2.87 (m, 4H), 1.39 (t, J=8.30 Hz, 3H)

Preparation 25

2-Ethyl-1-[2-(4-hydroxyphenylsulfanyl)ethyl]-4-phenyl-1,6-dihydropyrimidin-6-one

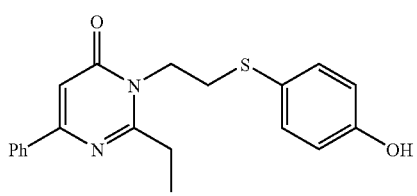

To 4-hydroxy thiophenol (2.016 g, 0.016 mol) in DMF (50 ml) K₂CO₃ (4.416 g, 0.032 mol) was added and stirred for 30 min. and then added 1-(2-chloroethyl)-2-ethyl-4-phenyl-1,6-dihydropyrimidin-6-one (4.3 g, 0.016 mol). The resulting mixture was stirred at room temperature for 15 h, filtered, washed with EtOAc and the combined filtrates were partitioned between water and EtOAc. The EtOAc layer was washed with water, brine, dried over Na₂SO₄ and evaporated the solvent to get the title compound as a gummy mass (1.25 g, 26%).

¹H NMR (CDCl₃, 200 MHz): δ 9.64 (s, 1H, D₂O exchangeable), 8.08-8.05 (m, 2H), 7.50-7.35 (m, 3H), 7.27 (d, J=9.28 Hz, 2H), 6.83 (s, 3H), 6.76 (d, J=9.28 Hz, 2H), 4.08 (t, J=81 Hz, 2H), 3.11 (t, J=7.81 Hz, 2H), 2.72 (q, J=6.84 Hz, 2H), 1.22 (t, J=7.32 Hz, 3H).

Example 1

Ethyl 2-[4-(2-ethyl-6-oxo-4-phenyl-1,6-dihydropyrimidin-1-ylmethyl(heptyl)carboxamido)phenyl sulfanyl}-3-methyl butanoate

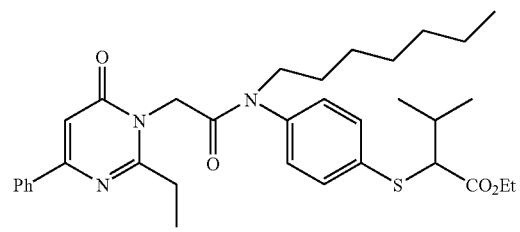

To a mixture of 2-(2-ethyl-6-oxo-4-phenyl-1,6-dihydro-1-pyrimidinyl)acetic acid obtained from preparation 23, (1.77 g, 6.89 mmol), ethyl-3-methyl-2-(4-heptylamino phenylthio)butanoate, obtained from preparation 17, (2.2 g, 6.26 mmol) and HOBt (0.85 g, 6.89 mmol) in dry DCM (30 mL) was added N,N-diisopropyl carbodiimide (DIC) (1.72 mL, 6.89 mmol) at RT and stirred at that temperature for 24 h. The reaction mixture was diluted with more DCM (100 mL) and washed with water, saturated NaHSO₄ solution, brine and the DCM layer was dried over Na₂SO₄ and evaporated the solvent. The crude ester was purified over silica gel column by eluting with 20% EtOAc:pet. ether to obtain the title compound as gummy mass (1.8 g, 49%).

¹H NMR (CDCl₃, 200 MHz): δ 8.02-7.97 (m, 2H), 7.55 (d, J=8.30 Hz, 2H), 7.46-7.42 (m, 3H), 7.32 (d, 2H), 6.75 (s, 1H), 4.49 (s, 2H), 4.17 (q, J=6.84 Hz, 2H), 4.17 (q, J=6.84 Hz, 2H), 3.69 (t, J=7.32 Hz, 2H), 3.51 (d, J=8.31 Hz, 1H), 2.70 (q, J=7.33 Hz, 2H), 2.24-2.13 (m, 1H), 1.40-1.20 (m, 2H), 1.35 (t, J=7.33 Hz, 3H), 1.25-1.06 (m, 17H), 0.85 (t, J=6.83 Hz, 3H).

The compounds given in Table V were also prepared using a similar method described in Example 1.

TABLE V

| Example No. | Structure | mp/Nature | Yield | ¹H NMR (CDCl$_3$): δ |
|---|---|---|---|---|
| 2 | (structure) | 148-150° C. | 20% | 8.1-7.98 (m, 2H), 7.70 (d, J = 8.79 Hz, 2H), 7.50-7.4 (m, 3H), 6.84 (d, J = 8.79 Hz, 2H), 6.83 (s, 1H), 4.38 (t, J = 5.86 Hz, H), 4.22 (q, J = 6.84 Hz, 2H), 3.79 (t, J = 5.86 Hz, 2H), 2.97 (q, J = 7.33 Hz, 2H), 1.45 (t, J = 7.33 Hz, 3H), 1.36 (s, sH), 1.30 (s, 3H), 1.26 (t, J = 6.84 Hz, 3H). |
| 3 | (structure) | Liquid | 54% | 8.10-7.95 (m, 2H), 7.5-7.4 (m, 3H), 7.28 (d, J = 8.30 Hz, 2H), 6.84 (d, J = 8.3 Hz, 2H), 6.78 (s, 1H), 4.36 (t, J = 5.84 Hz, 2H), 4.23 (q, J = 7.3 Hz, 2H), 3.71 (t, J = 5.84 Hz, 2H), 3.28 (t, J = 6.83 Hz, 2H), 3.08 (q, J = 6.84 Hz, 2H), 1.62 (s, 6H), 1.5-1.3 (m, 2H), 1.28-1.0 (m, 14H), 0.84 (t, J = 6.32 Hz, 3H). |
| 4 | (structure) | 128-130° C. | 31% | 8.89 (s, 1H, D$_2$O exchangeable), 8.10-8.00 (m, 2H), 7.50-7.45 (m, 3H), 7.38 (d, J = 8.79 Hz, 2H), 6.87 (s, 1H), 6.81 (d, J =8.79 Hz, 2H), 4.85 (s, 2H), 4.22 (q, J = 6.84 Hz, 2H), 3.08 (d, J = 7.32 Hz, 2H), 1.55 (s, 6H), 1.45 (t, J = 7.32 Hz, 3H), 1.25 (t, J = 6.84 Hz, 3H). |
| 5 | (structure) | Liquid | 55% | 8.02-7.95 (m, 2H), 7.45-7.40 (m, 3H), 7.24 (d, J = 8.30 Hz, 2H), 6,74 (s, 1H), 4.48 (s, 2H), 4.26 (q, J = 7.33 Hz, 2H), 3.66 (t, J = 6.84 Hz, 2H), 2.68 (q, J = 7.32 Hz, 2H), 1.64 (s, 6H), 1.37 (q, J = 7.32 Hz, 2H), 1.25-1.10 (m, 16H), 0.85 (t, J = 5.86 Hz, 3H). |
| 6 | (structure) | Liquid | 47% | 8.10-8.00 (m, 2H), 7.60 (d, J = 8.31 Hz, 2H), 7.50-7.40 (m, 3H), 7.36 (d, J = 8.31 Hz, 2H), 6,78 (s, 1H), 4.48 (s, 2H), 4.16 (q, J = 6.84 Hz, 2H), 3.76 (t, J = 6.84 Hz, 2H), 2.70 (q, J = 7.33 Hz, 2H), 1.61 (s, 6H), 1.38 (t, J = 7.33 Hz, 3H), 1.25 (t, J = 6.84 Hz, 3H), 1.20-1.00 (m, 10H), 0.84 (t, J = 6.94 Hz, 3H). |

TABLE V-continued

| Example No. | Structure | mp/Nature | Yield | $^1$H NMR (CDCl$_3$): δ |
|---|---|---|---|---|
| 7 | 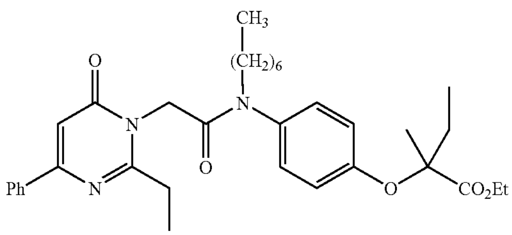 | Liquid | 48% | 8.05-7.95 (m, 2H), 7.50-7.40 (m, 3H), 7.26 (d, J = 8.30 Hz, 2H), 6.95 (d, J = 8.30 Hz, 2H), 6,78 (s, 1H), 4.50 (s, 2H), 4.28 (q, J = 6.84 Hz, 2H), 3.67 (t, J = 7.33 Hz, 2H), 2.69 (q, J = 7.32 Hz, 2H), 2.04 (q, J = 7.32 Hz, 2H), 1.58 (s, 3H), 1.39 (t, J = 7.32 Hz, 3H), 1.30-1.10 (m, 13H), 1.02 (t, J = 7.32 Hz, 3H), 0.86 (t, J = 5.37 Hz, 3H. |
| 8 | 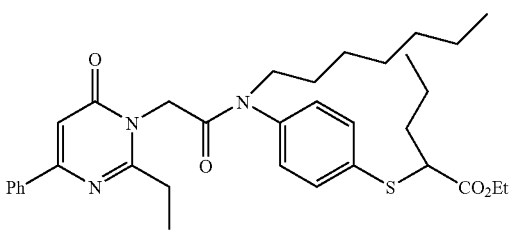 | Liquid | 76% | 8.05-7.97 (m, 2H), 7.56 (d, J = 8.30 Hz, 2H), 7.47-7.40 (m, 3H), 7.34 (d, J = 8.30 Hz, 2H), 7.27 (s, 1H), 4.50 (s, 2H), 4.18 (q, J = 6.83 Hz, 2H), 3.80-3.60 (m, 3H), 2.71 (q, J = 6.84 Hz, 2H), 2.40-2.15 (m, 2H), 2.10-1.50 (m, 4H), 1.39 (t, 16.84 Hz, 3H), 1.35-1.10 (m, 11H), 0.99-0.70 (m, 6H). |
| 9 | 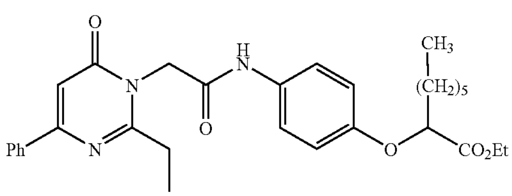 | 140-143° C. | 30% | 8.91(s, 1H, D$_2$O exchangeable), 8.10-8.00 (m, 2H), 7.50-7.46 (m, exchangeable), 8.10-8.00 3H), 7.41 (d, J = 8.79 Hz, 2H), 6,87 (s, 1H), 6.81 (d, J = 8.79 Hz, 2H), 4.85 (s, 2H), 4.53 (t, J = 6.35 Hz, 1H), 4.19 (q, J = 7.33 Hz, 2H), 3.07 (d, J = 7.33 Hz, 2H), 2.05-1.85 (m, 2H), 1.44 (t, J = 7.33 Hz, 3H), 1.35-1.15 (m, 11H), 0.85 (t, J = 4.99 Hz, 3H). |
| 10 | 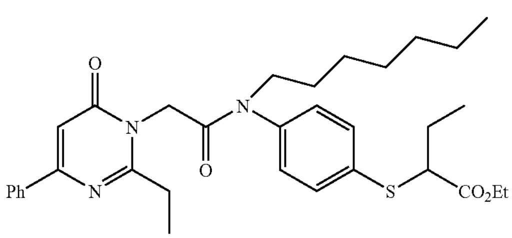 | Liquid | 35% | 8.05-8.00 (m, 2H), 7.57 (d, J = 8.31 Hz, 2H). 750-7.40 (m, 3H), 7.33 (d, J = 8.31 Hz, 2H), 6.75 (s, 1H), 4.49 (s, 2H), 4.18 (q, J = 7.32 Hz, 2H), 3.80-3.60 (m, 3H), 2.70 (q, J = 7.33 Hz, 2H), 2.05-1.80 (m, 2H), 1.60-1.58 (m, 2H), 1.30-1.20 (m, 14H), 1.07 (t, J = 7.33 Hz, 3H), 0.85 t, J = 6.34 Hz, 3H).. |
| 11 | 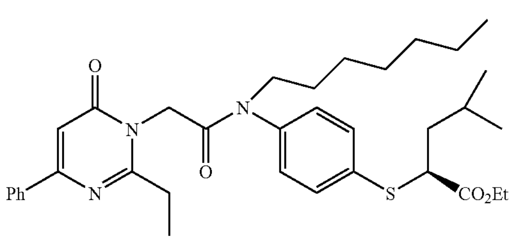 | Gummy oil | 22% | 8.05-7.95 (m, 2H), 7.55 (d, J = 8.79 Hz, 2H), 7.50-7.40 (m, 3H), 7.33 (d, J = 8.79 Hz, 2H), 6.74 (s, 1H), 4.49 (s, 2H), 4.15 (q, J = 7.33 Hz, 2H), 3.79 (t, J = 8.30 Hz, 1H), 3.69 (t, J = 7.82 Hz, 2H), 2.70 (q, J = 6.84 Hz, 2H), 2.30-2.20 (m, 1H), 1.90-1.60 (m, 2H), 1.60-1.50 (m, 2H), 1.45-1.10 (m, 17H), 1.00-0.8(m, 6H). |

TABLE V-continued

| Example No. | Structure | mp/Nature | Yield | $^1$H NMR (CDCl$_3$): δ |
|---|---|---|---|---|
| 12 | 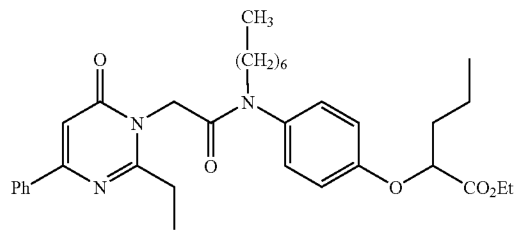 | Liquid | 88% | 8.02-7.95 (m, 2H), 7.50-7.35 (m, 3H), 7.26 (d, J = 8.79 Hz, 2H), 6.95 (d, J = 8.79 Hz, 2H), 6.73 (s, 1H), 4.61 (t, J = 5.38 Hz, 1H), 4.47 (s, 2H), 4.23 (q, J = 7.32 Hz, 2H), 3.64 (t, J = 7.32 Hz, 2H), 2.68 (q, J = 7.33 Hz, 2H), 2.00-1.80 (m, 2H), 1.60-1.40 (m, 2H), 1.36 (t, J = 7.33 Hz, 3H), 1.30-1.10 (m, 13H), 0.98 (t, 7.33 Hz, 3H).0.82 (t, J = 6.80 Hz, 3H. |
| 13 | 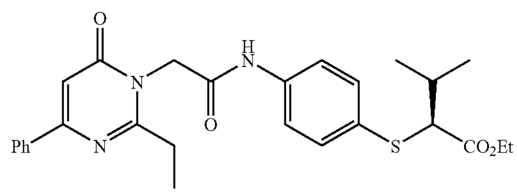 | Liquid | 51% | 8.05-7.95 (m, 2H), 7.50-7.30 (m, 7H), 6.86 (s, 1H), 4.84 (s, 2H), 4.08 (q, J = 8.29 Hz, 2H), 3.28 (d, J = 8.29 Hz, 1H), 3.05 (q, J = 6.84 Hz, 2H), 2.10-1.95 (m, 1H), 1.43 (t, J = 7.33 Hz, 3H), 1.30-0.95 (m, 9H). |

Example 14

Ethyl 2-{4-[2-(2-ethyl-6-oxo-4-phenyl-1,6-dihydro-pyrimidin-1-yl)ethoxy]phenoxy}-2-methyl propanoate

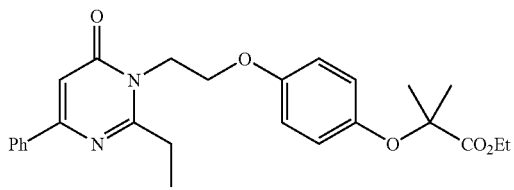

To a solution of ethyl-2-methyl-4-hydroxy phenoxy propanoate (454.6 mg, 1.863m mol) (obtained from preparation 4) in dry DMF (10 mL) was added K$_2$CO$_3$ (514 mg, 3.726 mmol) and stirred at RT for 30 min. To this 1-(2-chloroethyl)-2-ethyl-4-phenyl-1,6-dihydro-6-pyrimidinone (489 mg, 1.863 mmol) in DMF (5 mL) was added and the resulting mixture was stirred at 80° C. for 12 h. The reaction mixture was filtered, diluted with EtOAc (100 mL) and washed with water, brine and dried over Na$_2$SO$_4$. The solvent was evaporated and purified by column chromatography by eluting with 20% EtOAc:pet. ether to give the title compound as a white solid (mp: 80-82° C., 226 mg, 27%).

$^1$H NMR (CDCl$_3$, 200 MHz): δ 8.03-8.00 (m, 2H), 7.47-7.43 (m, 3H), 6.85 (d, J=9.28 Hz, 2H), 6.78 (s,1H), 6.71 (d, J=9.28 Hz, 2H), 4.46 (t, J=4.89, 2H), 4.27 (q, J=8.81 Hz, 2H), 4.20 (t, J=4.89 Hz, 2H), 3.08 (q, J=7.32 Hz, 2H), 1.51 (s, 6H), 1.40 (t, J=7.32 Hz, 3H), 1.26 (t, J=8.81 Hz, 3H).

The compounds given in Table VI were also prepared using a similar method described in Example 14.

TABLE VI

| Example No. | Structure | mp/Nature | Yield | $^1$H NMR (CDCl$_3$): δ |
|---|---|---|---|---|
| 15 | 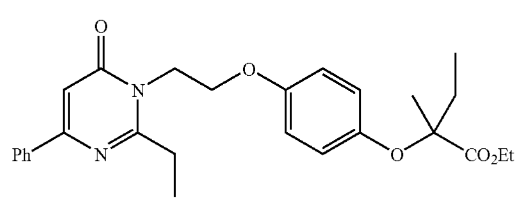 | Liquid | 20% | 8.05-7.95(m, 2H), 7.50-7.40 (m, 3H), 6.82(S, 1H), 6.80 (d, J = 9.28 Hz, 2H), 6.70 (d, J = 9.28 Hz, 2H), 4.45 (t, J = 4.88 Hz, 2H), 4.25 (t, J = 4.88 Hz, 2H), 4.21 (q, J = 7.32 Hz, 2H), 3.07 (q, J = 7.33 Hz, 2H), 1.90 (q, J = 7.32 Hz, 2H), 1.60 (s, 3H), 1.43 (t, J = 7.33 Hz, 3H), 1.25 (t, J = 7.32 Hz, 3H), 0.95 (t, J = 7.32 Hz, 3H). |

TABLE VI-continued

| Example No. | Structure | mp/Nature | Yield | ¹H NMR (CDCl₃): δ |
|---|---|---|---|---|
| 16 | 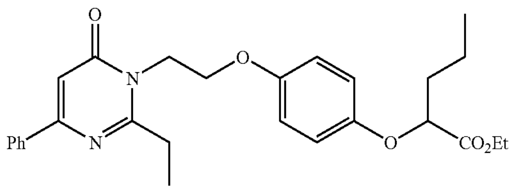 | 80-82° C. | 32% | 8.05-7.95 (m, 2H), 7.50-7.40 (m, 3H), 6.80 (d, J = 9.27 Hz, 2H), 6.75 (d, J = 9.27 Hz, 2H), 6.73 (S, 1H), 4.52-4.40 (m, 1H), 4.45 (t, J = 4.88 Hz, 2H), 4.26 (t, J = 4.88 Hz, 2H), 4.18 (q, J = 6.84 Hz, 2H), 3.08 (q, J = 7.33 Hz, 2H), 1.95-1.80 (m, 2H), 1.60-1.50 (m, 2H), 1.44 (t, J = 7.32 Hz, 3H), 1.23 (t, J = 6.84 Hz, 3H), 0.95 (t, J = 6.34 Hz, 3H). |
| 17 | 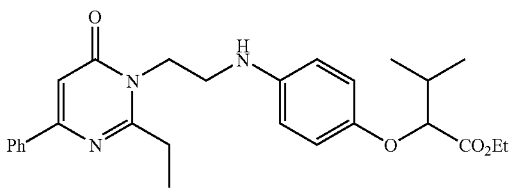 | Liquid | 47% | 8.05-8.00 (m, 2H), 7.55-7.40 (m, 3H), 7.31 (d, 8.30 Hz, 2H), 6.81 (S, 1H), 6.58 (d, J = 8.30 Hz, 2H), 4.33 (t, J = 5.86 Hz, 2H), 4.09 (q, J = 7.32 Hz, 2H), 3.54 (t, J = 5.86 Hz, 2H), 3.17 (d, J = 9.28 Hz, 1H), 2.82 (q, J = 6.83 Hz, 2H), 2.10-1.95 (m, 1H), 1.40 (t, J = 7.32 Hz, 3H), 1.22 (t, J = 6.83 Hz, 3H), 1.14 (d, J = 6.34 Hz, 3H), 0.99 (d, J = 6.34 Hz, 3H). |
| 18 | 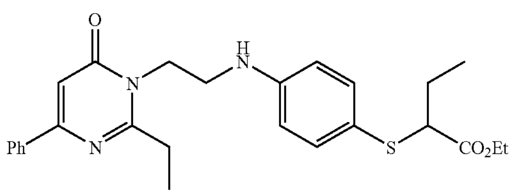 | Liquid | 56% | 8.00-7.90 (m, 2H), 7.50-7.40 (m, 3H), 7.29 (d, J = 8.79 Hz, 2H), 6.81 (S, 1H), 6.57 (d, J = 8.79 Hz, 2H), 4.33 (t, J = 5.86 Hz, 2H), 4.11 (q, = 6.84 Hz, 2H), 3.54 (t, J = 5.86 Hz, 2H), 3.32 (t, J = 7.83 Hz, 1H), 2.82 (q, J = 7.32 Hz, 2H), 1.90-1.50 (m, 2H), 1.40 (t, J = 7.32 Hz, 3H), 1.40 (t, J = 7.32 Hz, 3H), 0.98 (t, J = 7.33 Hz, 3H). |
| 19 | 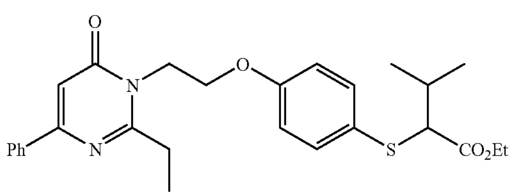 | Liquid | 69% | 8.10-7.95 (m, 2H), 7.50-7.40 (m, 3H), 7.38 (d, J = 8.79 Hz, 2H), 6.78 (d, J = 8.79 Hz, 2H), 6.79 (s, 1H), 4.48 (t, J = 4.88 Hz, 2H), 4.31 (t, J = 4.88 Hz, 2H), 4.08 (q, J = 7.32 Hz, 2H), 3.23 (d, J = 8.79 Hz, 1H), 3.08 (q, J = 7.33 Hz, 2H), 2.15-1.95 (m, 1H), 1.46 (t, J = 7.33 Hz, 3H), 1.26 (t, J = 7.32 Hz, 3H), 1.13 (d, J = 6.84 Hz, 3H), 0.99 (d, J = 6.84 Hz, 3H). |
| 20 | 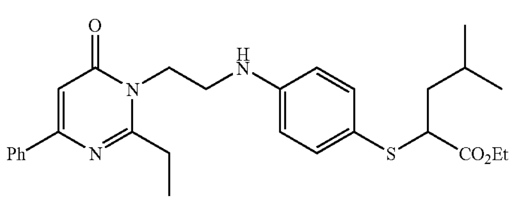 | Liquid | 65% | 8.05-8.00 (m, 2H), 7.50-7.40 (m, 3H), 7.30 (d, J = 8.32 Hz, 2H), 6.81 (s, 1H), 6.57 (d, J = 8.32 Hz, 2H), 4.57 (bs, 1H, D₂O exchangeable), 4.33 (t, J = 7.33 Hz, 2H), 4.10 (q, J = 7.32 Hz, 2H), 3.56-3.53 (m, 3H), 2.82 (q, J = 7.00 Hz, 2H), 1.75-1.52 (m, 3H), 1.40 (t, J = 7.00 Hz, 3H), 1.29-0.88 (m, 9H). |

TABLE VI-continued

| Example No. | Structure | mp/Nature | Yield | $^1$H NMR (CDCl$_3$): δ |
|---|---|---|---|---|
| 21 | 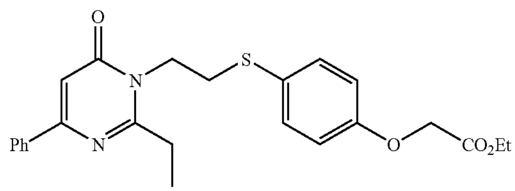 | Liquid | 80% | 7.98-7.93 (m, 2H), 7.45-7.26 (m, 5H), 6.83 (d, J = 8.79 Hz, 2H), 6.67 (s, 1H), 4.49 (s, 2H), 4.31-4.13 (m, 4H), 3.19 (t, J = 7.32 Hz, 2H), 2.69 (q, J = 7.83 Hz, 2H), 1.36-1.21 (m, 6H), |

Example 22

Ethyl 2-{4-[2-(2-ethyl-6-oxo-4-phenyl-1,6-dihydro-pyrimidin-1-yl)ethoxy]anilino}propanoate

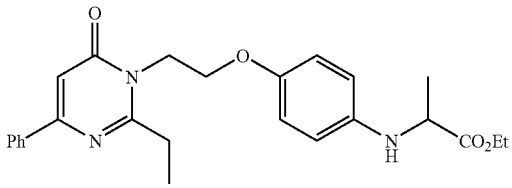

To a solution of 1-[2-ethyl-6-oxo-4-phenyl-1,6-dihydro-1-pyrimidinyl]-2-(aminophenoxy)ethane (1.9 g, 5.67 mmol) (Ref. U.S. Pat. No. 6,310,069) in dry DMF (20 mL) was added K$_2$CO$_3$ and stirred at RT for 30 min. To this ethyl-2-bromopropanoate (1.54 g, 8.51 mmol), was added and the mixture was stirred at 50° C. for 14 h. The reaction mixture was filtered, washed with EtOAc and the combined filtrates were washed with water and extracted with EtOAc. The organic layer was dried over Na$_2$SO$_4$, evaporated the solvent and the crude compound was purified by column chromatography by eluting with 25% EtOAc:pet. ether to give the title compound as a brownish low melting solid (mp: 40° C., 1.867 g, 76%).

$^1$H NMR (CDCl$_3$, 200 MHz): δ 8.03 (m, 2H), 7.98-7.26 (m, 3H), 6.78 (s, 1H), 6.70 (d, J=8.79 Hz, 2H), 6.54 (d, J=8.79 Hz, 2H), 4.42 (t, J=4.88 Hz, 2H), 4.23 (t, J=4.88 Hz, 2H), 4.14 (q, J=7.33 Hz, 2H), 4.02 (q, J=6.84 Hz, 1H), 3.08 (q, J=7.33 Hz, 2H), 1.50-1.29 (m, 6H), 1.22 (t, J=7.33 Hz, 3H).

The compounds given in Table VII were also prepared using a similar method described in Example 22.

TABLE VII

| Example No. | Structure | mp/Nature | Yield | $^1$H NMR (CDCl$_3$): δ |
|---|---|---|---|---|
| 23 | 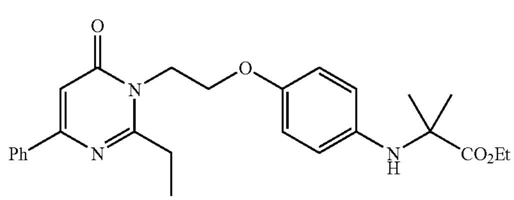 | Gummy oil | 50% | 8.05-7.95 (m, 2H), 7.50-7.40 (m, 3H), 6.78 (s, 1H), 6.69 (d, J = 9.28 Hz, 2H), 6.61 (d, J = 9.28 Hz, 2H), 4.44 (t, J = 4.88 Hz, 2H), 4.24 (t, J = 4.88 Hz, 2H), 4.13 (q, J = 7.33 Hz, 2H), 3.08 (q, J = 7.33 Hz, 2H), 1.47 (s, 6H), 1.40-1.10 (m, 6H). |
| 24 | 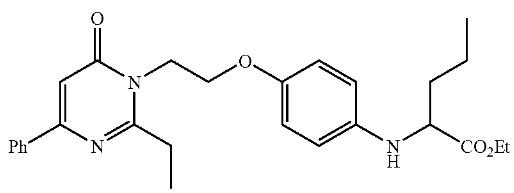 | 40° C. | 65% | 8.10-7.95 (m, 2H), 7.50-7.40 (m, 3H), 6.79 (s, 1H), 6.71 (d, J = 8.79 Hz, 2H), 6.55 (d, J = 8.79 Hz, 2H), 4.45 (t, J = 4.88 Hz, 2H), 4.24 (t, J = 4.88 Hz, 2H), 4.14 (q, J = 7.33 Hz, 2H), 3.95 (t, J = 6.84 Hz, 1H), 3.09 (q, J = 7.32 Hz, 2H), 2.40-2.20 (m, 2H), 1.80-1.60 (m, 2H), 1.43 (t, J = 7.32 Hz, 3H), 1.27 (t, J = 7.33 Hz, 3H), 0.95 (t, J = 7.33 Hz, 3H). |

TABLE VII-continued

| Example No. | Structure | mp/Nature | Yield | $^1$H NMR (CDCl$_3$): δ |
|---|---|---|---|---|
| 25 | 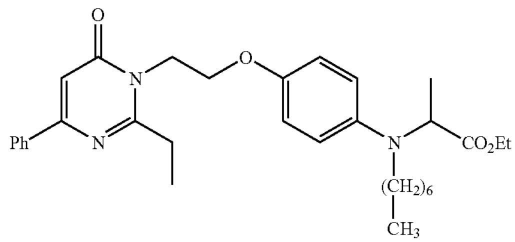 | 88-89° C. | 56% | 8.10-8.00 (m, 2H), 7.50-7.40 (m,3H), 6.79 (s, 1H), 6.71 (d, J = 9.28 Hz, 2H), 6.54 (d, J = 9.28 Hz, 2H), 4.47 (t, J = 4.89 Hz, 2H), 4.23 (t, J = 4.89 Hz, 2H), 4.07 (q, J = 6.84 Hz, 2H), 4.00 (t, J = 7.60 Hz, 2H), 3.90 (q, J = 6.84 Hz, 1H), 3.09 (q, J = 7.32 Hz, 2H), 1.70-1.50 (m, 5H), 1.41 (t, J = 7.32 Hz, 3H), 1.35-1.20 (m, 11H), 0.88 (t, J = 5.86 Hz, 3H). |

Example 26

2-[4-(2-Ethyl-6-oxo-4-phenyl-1,6-dihydropyrimidin-1-ylmethyl(heptyl)carboxamido)phenyl sulfanyl}-3-methyl butanoic acid

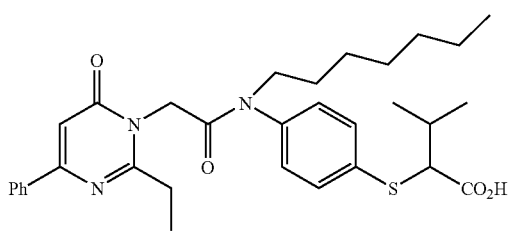

To ethyl 2-[4-(2-ethyl-6-oxo-4-phenyl-1,6-dihydropyrimidin-1-ylmethyl(heptyl)carboxamido)phenyl sulfanyl}-3-methyl butanoate (obtained from Example 1) (1.8 g, 3.0 mmol) in THF: MeOH (1:3) mixture (10 mL) was added LiOH (1.8 g, 4.28 mmol) dissolved in water (4 mL). The reaction mixture was stirred at RT for 12 h and the solvent was evaporated, diluted with water (10 mL) and acidified the mixture with 2 N HCl to pH 4 and extracted with EtOAc and washed with water, brine and dried over Na$_2$SO$_4$ and evaporated the solvent. The resulting crude material was purified over silica gel column by eluting with 1% MeOH: CHCl$_3$ to obtain the title compound as fluffy white solid (1.5 g, 89%).

$^1$H NMR (CDCl$_3$, 200 MHz): δ 8.10-7.90 (m, 2H), 7.59 (d, J=7.81 Hz, 2H), 7.50-7.39 (m, 3H), 7.32 (d, J=7.81 Hz, 2H), 6.79 (s, 1H), 4.45 (s, 2H), 3.67 (t, J=7.32 Hz, 2H), 3.55 (d, J=8.79 Hz, 1H), 2.67 (q, J=7.33 Hz, 2H), 2.30-2.15 (m, 1H), 1.60-1.45 (m, 2H), 1.40-1.05 (m, 17H), 0.84 (t, J=6.84 Hz, 3H).

The compounds given in Table VIII were also prepared using a similar method described in Example 26.

TABLE VI

| Example No. | Structure | mp/Nature | Yield | $^1$H NMR (CDCl$_3$): δ |
|---|---|---|---|---|
| 27 | 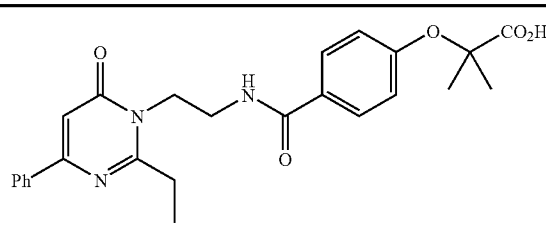 | 210° C. | 65% | 8.10-7.95 (m, 2H), 7.68 (d, J = 8.30 Hz, 2H), 7.55-7.40 (m, 3H), 6.88 (d, J = 8.30 Hz, 2H), 6.86 (s, 1H), 4.39 (t, 4.32 Hz, 2H), 3.80 (t, J = 4.32 Hz, 2H), 3.00 (q, J = 6.84 Hz, 2H), 1.70 (s, 6H), 1.47 (t, J = 6.84 Hz, 3H). |
| 28 | 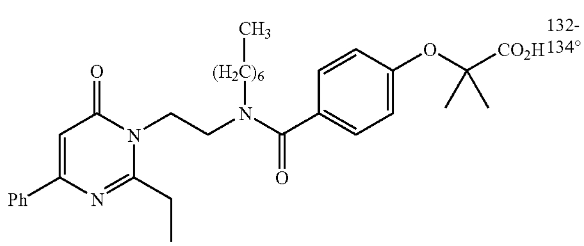 | 132-134° C. | 43% | 8.10-7.95 (m, 2H), 7.55-7.40 (m, 3H), 7.32 (d, J = 8.30 Hz, 2H), 6.91 (d, J = 8.30 Hz, 2H), 6.80 (s, 1H), 4.38 (t, J = 4.34 Hz, 2H), 3.73 (t, J = 4.34 Hz, 2H), 3.28 (t, J = 6.83 Hz, 2H), 3.08 (q, J = 7.82 Hz, 2H), 1.95-1.80 (m, 10H), 1.63 (s, 6H), 1.44 (t, J = 7.82 Hz, 3H), 0.84 (t, J = 4.83 Hz, 3H). |

TABLE VI-continued

| Example No. | Structure | mp/ Nature | Yield | $^1$H NMR (CDCl$_3$): δ |
|---|---|---|---|---|
| 29 | 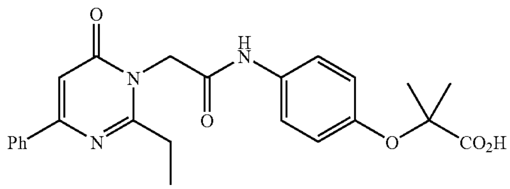 | 120° C. | 71% | 8.10-8.00 (m, 2H), 7.55-7.45 (m, 3H), 7.38 (d, J = 7.09 Hz, 2H), 6.86 (d, J = 7.09 Hz, 2H), 6.83 (s, 1H), 4.91 (s, 2H), 3.06 (q, J = 7.32 Hz, 2H), 1.56 (s, 6H), 1.45 (t, J = 7.32 Hz, 3H). |
| 30 | 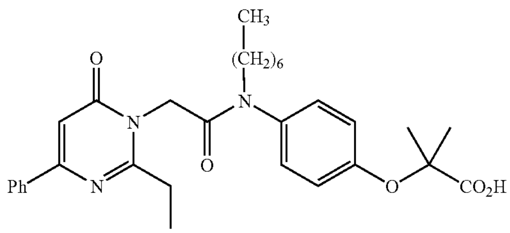 | 68-70° C. | 93% | 8.05-8.00 (m, 2H), 7.55-7.45 (m, 3H), 7.28 (d, J = 8.31 Hz, 2H), 7.02 (d, J = 8.31 Hz, 2H), 6.78 (s, 1H), 4.50 (s, 2H), 3.66 (t, J = 7.33 Hz, 2H), 2.70 (q, J = 7.32 Hz, 2H), 2.25-2.00 (m, 2H), 1.67 (s, 6H), 1.38 (t, J = 7.32 Hz, 3H), 1.38-1.18 (m, 8H), 0.85 (t, J = 6.83 Hz, 3H). |
| 31 | 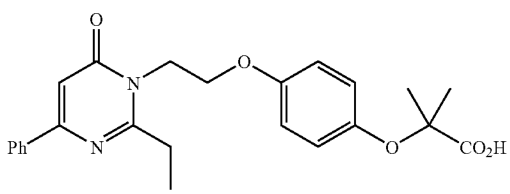 | 158-160° C. | 79% | 8.10-7.95 (m, 2H), 7.50-7.40 (m, 3H), 6.89 (d, J = 8.79 Hz, 2H), 6.81 (s, 1H), 6.76 (d, J = 8.79 Hz, 2H), 4.48 (t, J = 4.89 Hz, 2H), 4.48 (t, J = 4.89 Hz, 2H), 3.09 (q, J = 7.32 Hz, 2H), 1.50 (s, 6H), 1.45 (t, J = 7.32 Hz, 3H). |
| 32 | 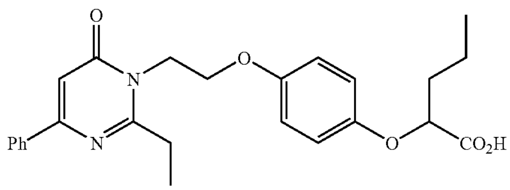 | 190-192° C. | 64% | 8.05-7.95 (m, 2H), 7.50-7.40 (m, 3H), 6.82 (d, J = 8.79 Hz, 2H), 6.74 (d, J = 8.79 Hz, 2H), 6.73 (s, 1H), 4.60-4.50 (m, 3H), 4.24 (t, J = 4.40 Hz, 2H), 3.09 (q, J = 7.33 Hz, 2H), 2.00-1.90 (m, 2H), 1.60-1.40 (m, 5H), 0.95 (t, J = 6.83 Hz, 3H). |
| 33 | 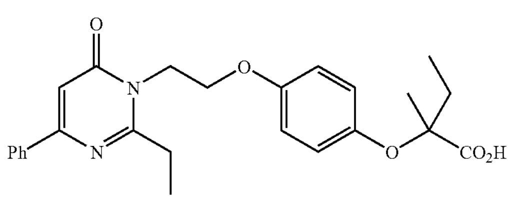 | 159-161° C. | 71% | 8.10-8.05 (m, 2H), 7.50-7.40 (m, 3H), 6.88 (d, J = 8.79 Hz, 2H), 6.79 (s, 1H), 6.78 (d, J = 8.79 Hz, 2H), 4.47 (t, J = 4.89 Hz, 2H), 4.28 (t, J = 4.89 Hz, 2H), 3.08 (q, J = 6.84 Hz, 2H), 1.88 (q, J = 7.33 Hz, 2H), 1.44 (t, J = 6.84 Hz, 3H), 1.36 (s, 3H), 1.01 (t, J = 7.33 Hz, 3H).. |
| 34 | 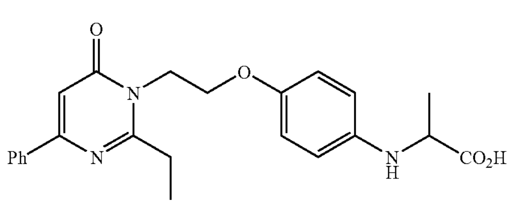 | 52° C. | 20% | 8.10-7.90 (m, 2H), 7.66 (d, J = 7.81 Hz, 2H), 7.50-7.40 (m, 3H), 7.36 (d, J = 7.81 Hz, 2H), 6.77 (s, 1H), 4.47 (s, 2H), 3.70 (t, J = 7.32 Hz, 2H), 2.70 (q, J = 7.32 Hz, 2H), 1.60-1.40 (m, 2H), 1.55 (s, 6H), 1.37 (t, J = 7.32 Hz, 3H), 1.30-1.10 (m, 8H), 0.84 (t, J = 4.99 Hz, 3H |
| 35 | 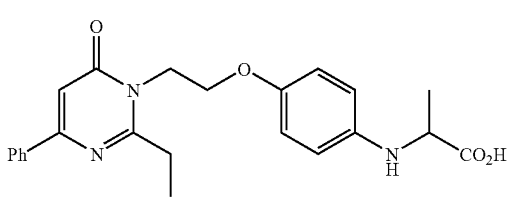 | 192-194° C. | 66% | 8.20-8.00 (m, 2H), 7.50-7.40 (m, 3H), 6.89 (s, 1H), 6.70 (d, J = 8.79 Hz, 2H), 6.48 (d, J = 8.79 Hz, 2H), 4.35 (t, J = 4.82 Hz, 2H), 4.12 (t, J = 4.82 Hz, 2H), 3.84 (q, J = 6.84 Hz, 1H), 3.04 (q, J = 7.33 Hz, 2H), 1.36 (t, J = 7.33 Hz, 3H), 1.31 (d, J = 6.84 Hz, 3H).. |

TABLE VI-continued

| Example No. | Structure | mp/ Nature | Yield | $^1$H NMR (CDCl$_3$): δ |
|---|---|---|---|---|
| 36 | (pyrimidinone with Ph, ethyl, CH$_2$C(O)N(CH$_2$)$_6$CH$_3$ on N-phenyl-O-C(CH$_3$)(Et)CO$_2$H) | 52-54° C. | 54% | 8.00-7.90 (m, 2H), 7.55-7.40 (m, 3H), 7.26 (d, J = 7.81 Hz, 2H), 7.03 (d, J = 7.81 Hz, 2H), 6.72 (s, 1H), 4.51 (s, 2H), 3.67 (t, J = 4.52 Hz, 2H), 2.81 (q, J = 5.87 Hz, 2H), 2.60-2.30 (m, 2H), 2.04 (t, J = 7.33 Hz, 2H), 1.58 (s, 3H), 1.41 (t, J = 5.87 Hz, 3H), 1.35-1.18 (m, 8H), 1.05 (t, 7.33 Hz, 3H), 0.85 (t, J = 7.22 Hz, 3H). |
| 37 | (pyrimidinone with Ph, ethyl, CH$_2$C(O)N(CH$_2$)$_6$CH$_3$ on N-phenyl-O-CH(Pr)CO$_2$H) | 48-50° C. | 74% | 8.00-7.90 (m, 2H), 7.50-7.39 (m, 3H), 7.30 (d, J = 8.79 Hz, 2H), 7.02 (d, J = 8.79 Hz, 2H), 6.85 (s, 1H), 4.67 (t, J = 5.86 Hz, 1H), 4.40 (s, 2H), 3.75-3.55 (m, 2H), 2.67 (q, J = 7.33 Hz, 2H), 2.10-1.90 (m, 2H), 1.70-1.40 (m, 2H), 1.34 (t, J = 7.33 Hz, 3H), 1.25-1.10 (m, 10H), 1.00 (t, J = 7.33 Hz, 3H), 0.85 (t, J = 6.84 Hz, 3H). |
| 38 | (pyrimidinone with Ph, ethyl, -CH$_2$CH$_2$-O-phenyl-NH-C(CH$_3$)$_2$CO$_2$H) | 168-169° C. | 25% | 8.03-7.45 (m, 2H), 7.55-7.40 (m, 3H), 7.23 (d, J = 9.78 Hz, 2H), 6.89 (s, 1H), 6.77 (d, J = 9.78 Hz, 2H), 4.44 (t, J = 4.88 Hz, 2H), 4.27 (t, J = 4.88 Hz, 2H), 3.04 (q, J = 7.33 Hz, 2H), 2.99 (s, 6H), 1.44 (t, J = 7.33 Hz, 3H). |
| 39 | (pyrimidinone with Ph, ethyl, -CH$_2$CH$_2$-O-phenyl-NH-CH(Pr)CO$_2$H) | 155-157° C. | 43% | 8/05-7.95 (m, 2H), 7.55-7.40 (m, 3H), 6.79 (s, 1H), 6.72 (d, J = 8.79 Hz, 2H), 6.60 (d, J = 8.79 Hz, 2H), 4.44 (t, J = 4.88 Hz, 2H), 4.23 (t, J = 4.88 Hz, 2H), 3.89 (t, J = 5.86 Hz, 1H), 3.08 (q, J = 7.32 Hz, 2H), 1.90-1.60 (m, 2H), 1.55-1.25 (m, 5H), 0.93 (t, J = 7.33 Hz, 3H. |
| 40 | (pyrimidinone with Ph, ethyl, CH$_2$C(O)N(octyl) on N-phenyl-S-CH(Bu)CO$_2$H) | Gummy oil | 40% | 8.05-7.95 (m, 2H), 7.59 (d, J = 8.30 Hz, 2H) 7.50-7.40 (m, 3H), 7.32 (d, J = 8.30 Hz, 2H), 6.79 (s, 1H), 4.45 (s, 2H), 3.75 (t, J = 7.33 Hz, 1H), 3.67 (t, J = 7.33 Hz, 2H), 2.67 (q, J = 7.33 Hz, 2H), 2.10-1.70 (m, 2H), 1.60-1.42 (m, 2H), 1.34 (t, J = 7.33 Hz, 3H), 1.30-1.05 (m, 10H), 0.96 (t, J = 7.33 Hz, 3H), 0.83 (t, J = 6.34 Hz, 3H. |
| 41 | (pyrimidinone with Ph, ethyl, -CH$_2$CH$_2$-S-phenyl-O-CH$_2$CO$_2$H) | 164-166° C. | 68% | 8.02-7.97 (m, 2H), 7.46-7.43 (m, 3H), 7.35 (d, J = 8.79 Hz, 2H), 6.81 (d, J = 8.79 Hz, 2H), 6.63 (s, 1H), 4.86 (s, 2H), 4.25 (t, J = 7.08 Hz, 2H), 3.24 (t, J = 7.32 Hz, 2H), 2.69 (q, J = 7.32 Hz, 2H), 1.30 (t, J = 7.08 Hz, 3H), |

TABLE VI-continued

| Example No. | Structure | mp/ Nature | Yield | $^1$H NMR (CDCl$_3$): δ |
|---|---|---|---|---|
| 42 | 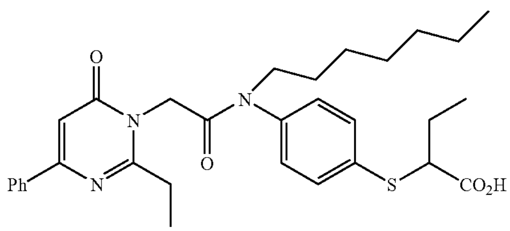 | Liquid | 70% | 8.05-7.90 (m, 2H), 7.60 (d, J = 8.30 Hz, 2H) 7.50-7.40 (m, 3H), 7.33 (d, J = 8.30 Hz, 2H), 6.80 (s, 1H), 4.46 (s, 2H), 3.68 (t, J = 7.33 Hz, 2H), 3.67 (t, J = 7.32 Hz, 1H), 2.68 (q, J = 7.33 Hz, 2H), 2.10-1.80 (m, 2H), 1.55-1.40 (m, 2H), 1.36 (t, J = 7.33 Hz, 3H), 1.30-1.05 (m, 8H), 1.10 (t, J = 7.33 Hz, 3H), 0.85 (t, J = 6.35 Hz, 3H). |
| 43 | 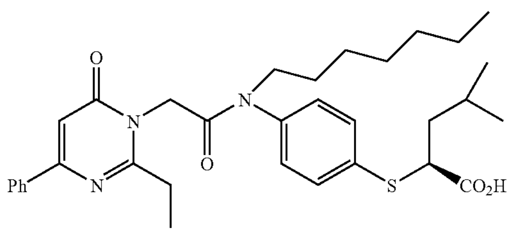 | 58-60° C. | 65% | 8.05-7.95 (m, 2H), 7.60 (d, J = 8.30 Hz, 2H) 7.50-7.40 (m, 3H), 7.34 (d, J = 8.30 Hz, 2H), 6.77 (s, 1H), 4.46 (s, 2H), 3.83 (t, J = 8.30 Hz, 1H), 3.70 (t, J = 7.33 Hz, 2H), 2.69 (q, J = 7.32 Hz, 2H), 2.20-2.00 (m, 2H), 1.95-1.80 (m, 1H), 1.60-1.40 (m, 2H), 1.36 (t, J = 7.33 Hz, 3H), 1.30-1.10 (m, 11H, 1.00-0.80 (m, 6H). |
| 44 | 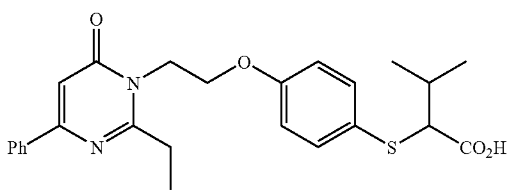 | 64° C. | 82% | 8.10-7.95 (m, 2H), 7.50-7.40 (m, 3H), 7.39 (d, J = 8.30 Hz, 2H), 6.79 (s, 1H), 6.77 (d, J = 8.30 Hz, 2H), 4.45 (t, J = 4.88 Hz, 2H), 4.28 (t, J = 4.88 Hz, 2H), 3.24 (d, J = 8.79 Hz, 1H), 3.05 (q, J = 7.32 Hz, 2H), 2.10-1.90 (m, 1H), 1.43 (t, J = 7.32 Hz, 3H), 1.13 (d, J = 6.35 Hz, 3H), 1.03 (d, J = 6.35 Hz, 3H). |
| 45 | 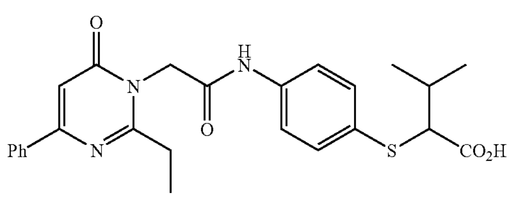 | 195-200° C. | 43% | 8.15-8.00 (m, 2H), 7.60-7.40 (m, 3H), 7.36 (d, J = 7.39 Hz, 2H), 6.86 (s, 1H) 6.66 (d, J = 7.39 Hz, 2H), 5.00 (s, 2H), 3.25 (d, J = 7.32 Hz, 1H), 2.89 (q, J = 7.32 Hz, 2H), 2.05-1.95 (m, 1H), 1.42 (t, J = 7.32 Hz, 3H), 1.10-1.00 (m, 6H). |
| 46 | 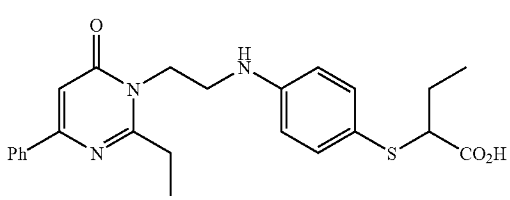 | 118° C. | 68% | 8.05-7.95 (m, 2H), 7.50-7.40 (m, 3H), 7.12 (d, J = 8.79 Hz, 2H), 6.81 (s, 1H), 6.56 (d, J = 8.79 Hz, 2H), 4.31 (t, J = 5.86 Hz, 2H), 3.52 (t, J = 5.86 Hz, 2H), 3.34 (t, J = 7.33 Hz, 1H), 2.80 (q, J = 7.33 Hz, 2H), 1.90-1.60 (m, 2H), 1.38 (t, J = 7.33 Hz, 3H), 1.03 (t, J = 7.33 Hz, 3H). |
| 47 | 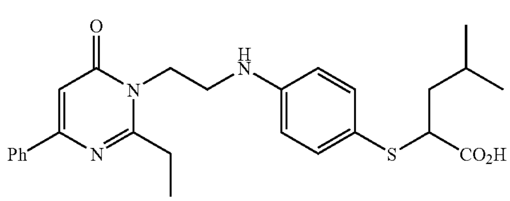 | 62-64° C. | 95% | 8.05-7.95 (m, 2H), 7.50-7.40 (m, 3H), 7.33 (d, J = 8.30 Hz, 2H), 6.82 (s, 1H), 6.58 (d, J = 8.30 Hz, 2H), 4.32 (t, J = 5.40 Hz, 2H), 3.53-3.40 (m, 3H), 2.81 (q, J = 7.30 Hz, 2H), 1.84-1.51 (m, 3H), 1.36 (t, J = 7.30 Hz, 3H), 0.95-0.80 (m, 6H). |

TABLE VI-continued

| Example No. | Structure | mp/ Nature | Yield | $^1$H NMR (CDCl$_3$): δ |
|---|---|---|---|---|
| 48 | 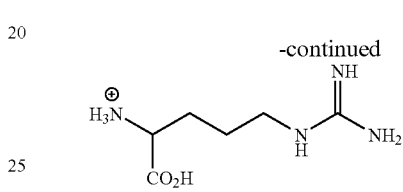 | 65-70° C. | 55% | 8.00-7.95 (m, 2H), 7.50-7.40 (m, 3H), 7.32 (d, J = 8.31 Hz, 2H), 6.81 (s, 1H), 6.54 (d, J = 8.31 Hz, 2H), 4.62 (bs, 1H, D$_2$O exchangeable), 4.29 (t, J = 5.86 Hz, 2H), 3.49 (t, J = 5.86 Hz, 2H), 3.17 (d, J = 9.27 Hz, 1H), 2.79 (q, J = 7.32 Hz, 2H), 2.15-1.95 (m, 1H), 1.37 (t, J = 7.32 Hz, 3H), 1.16 (d, J = 6.83 Hz, 3H), 1.04 (d, J = 6.83 Hz, 3H). |

Example 49

2-[4-(2-Ethyl-6-oxo-4-phenyl-1,6-dihydropyrimidin-1-ylmethyl(heptyl)carboxamido)phenyl sulfanyl}butanoic acid, arginine salt

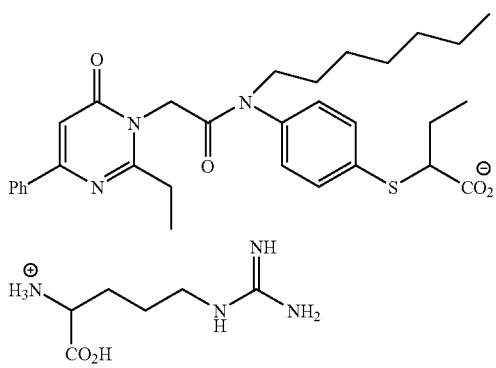

To 2-[4-(2-ethyl-6-oxo-4-phenyl-1,6-dihydropyrimidin-1-ylmethyl(heptyl)carboxamido)phenyl sulfanyl}butanoic acid, (obtained from example 42) (130 mg, 0.236 mmol) in dry methanol (5 mL) was added L-arginine (41 mg, 0.236 mmol) and stirred at 30° C. for 24 h. The solvent was evaporated and the residue was triturated with dry ethyl ether and dried under vacuum at 50° C. to give the title compound as a white amorphous solid (mp: 104-6° C., yield 90%).

IR(KBr): ν cm$^{-1}$ 3358, 2929, 1667, 1584.

Example 50

2-[4-(2-Ethyl-6-oxo-4-phenyl-1,6-dihydropyrimidin-1-ylmethyl(heptyl)carboxamido)phenyl sulfanyl}-4-methylpentanoic acid, arginine salt

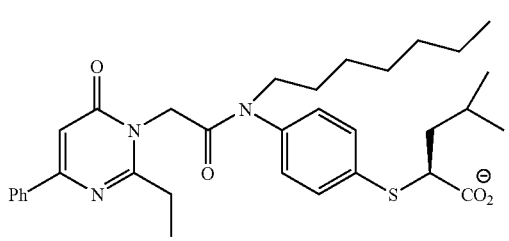

The title compound is prepared from 2-[4-(2-ethyl-6-oxo-4-phenyl-1,6-dihydropyrimidin-1-ylmethyl(heptyl)carboxamido)phenylsulfanyl}-2-methyl pentanoic acid, according to the similar method to that described in Example 48 (mp: 120-122° C.; yield 90%)

IR(KBr): ν cm$^{-1}$ 3356, 3162, 1664.

Example 51

2-[4-(2-Ethyl-6-oxo-4-phenyl-1,6-dihyropyrimidin-1-ylmethyl(heptyl)caroxamido)phenyl sulfanyl}butanoic cid, magnesium salt

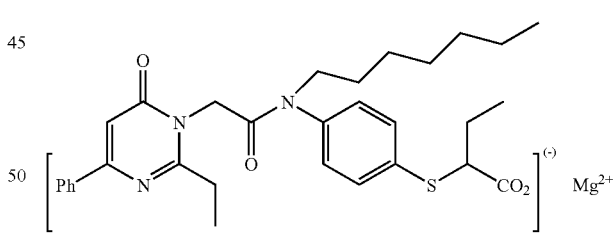

To 2-[4-(2-ethyl-6-oxo-4-phenyl-1,6-dihydropyrimidin-1-ylmethyl(heptyl)carboxamido)phenyl sulfanyl}butanoic acid (obtained from example 42) (150 mg, 0.284 mmol) in dry methanol (5 mL) was added magnesium hydroxide (8.28 mg, 0.142 mmol) and refluxed for 24 h. The solvent was evaporated and the residue was triturated with dry ethyl ether and dried under vacuum at 50° C. to give the title compound as a white amorphous solid (mp: 138-142° C., yield 90%).

IR(KBr): ν cm$^{-1}$ 3421, 2927, 1670, 1546.

The compounds given in Table VII were also prepared using a similar method described in Example 51.

TABLE VII

| Example No. | Structure | mp/Nature | Yield | IR |
|---|---|---|---|---|
| 52 | [Structure with Ph-pyrimidinone-CH₂-C(O)-N(hexyl)-phenyl-S-CH(iBu)-CO₂⁻]₂ Mg²⁺ | 140-144° C. | 90% | 3441, 2920, 1671. |
| 53 | [Structure with Ph-pyrimidinone-CH₂-C(O)-N(hexyl)-phenyl-S-CH(iPr)-CO₂⁻]₂ Mg²⁺ | 140-142° C. | 92% | 3446, 2937, 1670. |

The compounds of the present invention lower random blood sugar level, triglyceride, total cholesterol, LDL, VLDL and increased HDL. This was demonstrated by in vitro as well as in vivo animal experiments.

Demonstration of Efficacy of Compounds:

A) In Vitro:

a) Determination of hPPARα Activity:

Ligand binding domain of hPPARα was fused to DNA binding domain of Yeast transcription factor GAL4 in eucaryotic expression vector. Using superfect (Qiagen, Germany) as transfecting reagent HEK-293 cells were transfected with this plasmid and a reporter plasmid harboring the luciferase gene driven by a GAL4 specific promoter. Compound was added at different concentrations after 42 hrs of transfection and incubated overnight. Luciferase activity as a function of compound binding/activation capacity of PPARα was measured using Packard Luclite kit (Packard, USA) in Top Count (Ivan Sadowski, Brendan Bell, Peter Broag and Melvyn Hollis. Gene. 1992. 118: 137-141; Superfect Transfection Reagent Handbook. February 1997. Qiagen, Germany).

b) Determination of hPPARγ Activity:

Ligand binding domain of hPPARγ1 was fused to DNA binding domain of Yeast transcription factor GAL4 in eucaryotic expression vector. Using lipofectamine (Gibco BRL, USA) as transfecting reagent HEK-293 cells were transfected with this plasmid and a reporter plasmid harboring the luciferase gene driven by a GAL4 specific promoter. Compound was added at 1 µM concentration after 48 hrs of transfection and incubated overnight. Luciferase activity as a function of drug binding/activation capacity of PPARγ1 was measured using Packard Luclite kit (Packard, USA) in Packard Top Count (Ivan Sadowski, Brendan Bell, Peter Broag and Melvyn Hollis. Gene. 1992. 118: 137-141; Guide to Eukaryotic Transfections with Cationic Lipid Reagents. Life Technologies, GIBCO BRL, USA).

| Example No | Concentration | PPARα | Concentration | PPARγ |
|---|---|---|---|---|
| Example 35 | 50 µM | 6.2 | 1 µM | 2.2 |
| Example 36 | 50 µM | 7.5 | 1 µM | 1.2 |
| Example 43 | 50 µM | 6.7 | 1 µM | 2.2 |
| Example 45 | 50 µM | 7.2 | 1 µM | 0.8 |
| Example 46 | 50 µM | 6.5 | 1 µM | 3.1 |
| Wy 14643* | 50 µM | 7 | 1 µM | — |
| Rosiglitazone | 50 µM | — | 1 µM | 18 |

*reference standard c) Determination of HMG CoA Reductase Inhibition Activity:

Liver microsome bound reductase was prepared from 2% cholestyramine fed rats at mid-dark cycle. Spectrophotometric assays were carried out in 100 mM $KH_2PO_4$, 4 mM DTT, 0.2 mM NADPH, 0.3 mM HMG CoA and 125 µg of liver microsomal enzyme. Total reaction mixture volume was kept as 1 ml. Reaction was started by addition of HMG CoA. Reaction mixture was incubated at 37° C. for 30 min and decrease in absorbance at 340 nm was recorded. Reaction mixture without substrate was used as blank (Goldstein, J. L and Brown, M. S. Progress in understanding the LDL receptor and HMG CoA reductase, two membrane proteins that regulate the plasma cholesterol. J. Lipid Res. 1984, 25: 1450-1461). The test compounds inhibited the HMG CoA reductase enzyme.

B) In Vivo

Efficacy in Genetic Models:

Mutation in colonies of laboratory animals and different sensitivities to dietary regimens have made the development of animal models with non-insulin dependent diabetes and hyperlipidemia associated with obesity and insulin resistance possible. Genetic models such as db/db and ob/ob (Diabetes, (1982) 31(1): 1-6) mice and zucker fa/fa rats have been developed by the various laboratories for understanding the pathophysiology of disease and testing the efficacy of new antidiabetic compounds (Diabetes, (1983) 32: 830-838; Annu. Rep. Sankyo Res. Lab. (1994). 46: 1-57). The homozygous animals, C57 BL/KsJ-db/db mice developed by Jackson Laboratory, US, are obese, hyperglycemic, hyperinsulinemic and insulin resistant (J. Clin. Invest., (1990) 85: 962-967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

Mate C57BL/KsJ-db/db mice of 8 to 14 weeks age, having body weight range of 35 to 60 grams, bred at Dr. Reddy's Research Foundation (DRF) animal house, were used in the experiment. The mice were provided with standard feed (National Institute of Nutrition (NIN), Hyderabad, India) and acidified water, ad libitum. The animals having more than 350 mg/dl blood sugar were used for testing. The number of animals in each group was 4.

Test compounds were suspended on 0.25% carboxymethyl cellulose and administered to test group at a dose of 0.001 mg to 30 mg/kg through oral gavage daily for 6 days. The control group received vehicle (dose 10 ml/kg). On 6th day the blood samples were collected one hour after administration of test compounds/vehicle for assessing the biological activity.

The random blood sugar and triglyceride levels were measured by collecting blood (100 µl) through orbital sinus, using heparinised capillary in tubes containing EDTA which was centrifuged to obtain plasma. The plasma glucose and triglyceride levels were measured spectrometrically, by glucose oxidase and glycerol-3-$PO_4$ oxidase/peroxidase enzyme (Dr. Reddy's Lab. Diagnostic Division Kits, Hyderabad, India) methods respectively.

The blood sugar and triglycerides lowering activities of the test compound was calculated according to the formula.

No adverse effects were observed for any of the mentioned compounds of invention in the above test.

| Compound | Dose (mg/kg) | Reduction in Blood Glucose Level (%) | Triglyceride Lowering (%) |
|---|---|---|---|
| Example 30 | 10 | 34 | 63 |
| Example 26 | 10 | 41 | 45 |
| Example 43 | 10 | 39 | 43 |

The ob/ob mice are obtained at 5 weeks of age from Bomholtgard, Denmark and were used at 8 weeks of age. Zucker fa/fa fatty rats are obtained from IffaCredo, France at 10 weeks of age and were used at 13 weeks of age. The animals are maintained under 12 hour light and dark cycle at 25±1° C. Animals are given standard laboratory chow (NIN, Hyderabad, India) and water, ad libitum (Fujiwara, T., Yoshioka, S., Yoshioka, T., Ushiyama, I and Horikoshi, H. Characterization of new oral antidiabetic agent CS-045. Studies in KK and ob/ob mice and Zucker fatty rats. Diabetes. 1988. 37: 1549-1558).

The test compounds are to be administered at 0.1 to 30 mg/kg/day dose for 9 days. The control animals received the vehicle (0.25% carboxymethylcellulose, dose 10 ml/kg) through oral gavage.

The blood are to be collected in fed state 1 hour after drug administration on 0 and 9 day of treatment. The blood is collected from the retro-orbital sinus through heparinised capillary in EDTA containing tubes. After centrifugation, plasma sample is separated for triglyceride, glucose, free fatty acid, total cholesterol and insulin estimations. Measurement of plasma triglyceride, glucose, total cholesterol will be done using commercial kits (Dr. Reddy's Laboratory, Diagnostic Division kits, Hyderabad, India). The plasma free fatty acid will be measured using a commercial kit form Boehringer Mannheim, Germany. The plasma insulin will be measured using a RIA kit (BARC, India). The reduction of various parameters examined are calculated according to the formula given below.

In ob/ob mice oral glucose tolerance test is performed after 9 days treatment. Mice are fasted for 5 hrs and challenged with 3 gm/kg of glucose orally. The blood samples are collected at 0, 15, 30, 60 and 120 min for estimation of plasma glucose levels.

The experimental results suggest that the compounds of the present invention also possess therapeutic utility as a prophylactic or regular treatment for diabetes, obesity, cardiovascular disorders such as hypertension, hyperlipidaemia and other diseases; as it is known from the literature that such diseases are interrelated to each other.

Blood glucose level and triglycerides are also lowered at doses greater than 10 mg/kg. Normally, the quantum of reduction is dose dependent and plateaus at certain dose.

b) Cholesterol Lowering Activity in Hypercholesterolemic Rat Models:

Male Sprague Dawley rats (NIN stock) are bred in DRF animal house. Animals are maintained under 12 hour light and dark cycle at 25±1° C. Rats of 180-200 gram body weight range are used for the experiment. Animals are made hypercholesterolemic by feeding 2% cholesterol and 1% sodium cholate mixed with standard laboratory chow [National Institute of Nutrition (NIN), Hyderabad, India] for 6 days. Throughout the experimental period the animals were maintained on the same diet (Petit, D., Bonnefis, M. T., Rey, C and Infante, R. Effects of ciprofibrate on liver lipids and lipoprotein synthesis in normo- and hyperlipidemic rats. Atherosclerosis. 1988. 74: 215-225).

The test compounds are administered orally at a dose 0.1 to 30 mg/kg/day for 3 days. Control group is treated with vehicle alone (0.25% Carboxymethylcellulose; dose 10 ml/kg).

The blood samples are collected in fed state 1 hour after drug administration on 0 and 3 day of compound treatment. The blood was collected from the retro-orbital sinus through heparinised capillary in EDTA containing tubes. After centrifugation, plasma sample is separated for total cholesterol, HDL and triglyceride estimations. Measurement of plasma triglyceride, total cholesterol and HDL is done using commercial kits (Dr. Reddy's Laboratory, Diagnostic Division, India). LDL and VLDL cholesterol is calculated from the data obtained for total cholesterol, HDL and triglyceride. The reduction of various parameters examined is calculated according to the formula given below.

c) Plasma Triglyceride and Total Cholesterol Lowering Activity in Swiss Albino Mice and Guinea Pigs:

Male Swiss albino mice (SAM) and male Guinea pigs were obtained from NIN and housed in DRF animal house. All these animals were maintained under 12 hour light and dark cycle at 25±1° C. Animals were given standard laboratory chow (NIN, Hyderabad, India) and water, ad libitum. SAM of 20-25 g body weight range and Guinea pigs of 500-700 g body weight range were used (Oliver, P., Plancke, M. O., Marzin, D., Clavey, V., Sauzieres, J and Fruchart, J. C. Effects of fenofibrate, gemfibrozil and nicotinic acid on plasma lipoprotein levels in normal and hyperlipidemic mice. Atherosclerosis, 1988. 70: 107-114).

The test compounds were administered orally to Swiss albino mice at 0.3 to 30 mg/kg/day dose for 6 days. Control mice were treated with vehicle (0.25% Carboxymethylcellulose; dose 10 ml/kg). The test compounds were administered orally to Guinea pigs at 0.3 to 30 mg/kg/day dose for 6 days. Control animals were treated with vehicle (0.25% Carboxymethylcellulose; dose 5 ml/kg).

The blood samples were collected in fed state 1 hour after drug administration on 0 and 6 day of treatment. The blood was collected from the retro-orbital sinus through heparinised capillary in EDTA containing tubes. After centrifugation, plasma sample was separated for triglyceride and total cholesterol (Wieland, O. Methods of Enzymatic analysis. Bergermeyer, H. O., Ed., 1963. 211-214; Trinder, P. Ann. Clin. Biochem. 1969. 6: 24-27). Measurement of plasma triglyceride, total cholesterol and HDL were done using commercial kits (Dr. Reddy's Diagnostic Division, Hyderabad, India).

| Compound | Dose (mg/kg) | Triglyceride Lowering (%) |
|---|---|---|
| Example 44 | 3 | 36 |
| Example 43 | 3 | 44 |
| Example 49 | 10 | 69 |

Formulae for Calculation:

1. Percent reduction in Blood sugar/triglycerides/total cholesterol were calculated according to the formula:

$$\text{Percent reduction (\%)} = \left[1 - \frac{TT/OT}{TC/OC}\right] \times 100$$

OC=Zero day control group value
OT=Zero day treated group value
TC=Test day control group value
TT=Test day treated group value 2. LDL and VLDL cholesterol levels were calculated according to the formula:

LDL cholesterol in $$\text{mg/dl} = \left[\text{Total cholesterol} - \text{HDL cholesterol} - \frac{\text{Triglyceride}}{5}\right] \text{mg/dl}$$

VLDL cholesterol in mg/dl=[Total cholesterol−HDL cholesterol−LDL cholesterol]mg/dl.

What is claimed is:
1. A compound of formula (I)

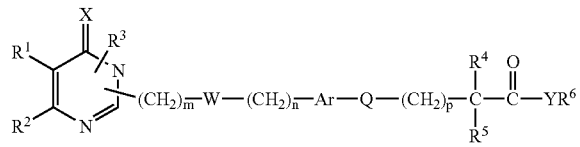

(I)

its tautomeric forms, its stereoisomers, its polymorphs, its pharmaceutically acceptable salts, or its pharmaceutically acceptable solvates, wherein X represents O or S; the group $R^1$ and the group $R^3$ when attached to the carbon atom, are the same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its amides, or sulfonic acid or its amides; $R^2$ represents cycloalkyl, aryl, aryloxy, aralkyl, aralkoxy, hererocyclyl, heteroaryl, heteroaralkyl, heteroaryloxy, heteroaralkoxy, arylamino, aralkylamino, aryloxycarbonyl, aralkoxycarbonyl, aryloxyalkyl, aralkyoxyalkyl, aryloxycarbonylamino or aralkoxycarbonylamino; wherein when a group represented by $R^1$, $R^2$ or the group $R^3$ when attached to a carbon atom is substituted, the substituent is slected from halogen, hydroxy, nitro, thio, alkyl, cycloalkyl, alkoxy, cycloalkoxy, aryl, aralkyl, aryloxy, aralkoxy, aolkoxyalkyl, aryloxyalkyl, aralkoxyalkyl, heterocyclyl, heteroaryl, heteroaralkyl, acyl, acyloxy, hydroxyalkyl, amino, acylamino, arylamino, aminoalkyl, alkoxycarbonyl, monoalkylamino, dialkyamino, alkylthio, carboxylic acid or its amides or sulfonic acid or its amides; $R^3$ when attached to nitrogen atom represents hydrogen, hydroxy, formyl or substituted or unsubsituted groups selected from alkyl, cycloalkyl, alkoxy, cycloalkoxy, aryl, aralkyl, heterocyclyl, heteroaryl, heteroaralkyl, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, carboxylic acid or its amides, or sulfonic acid or its amides; wherein when the group $R^3$ when attached to nitrogen is substituted, the sustituent is selected from halogen, hydroxy, acyl, acyloxy or amino groups; the linking group represented by —(CH$_2$)m-W—(CH$_2$)n- is attached either through nigtrogen atom or through carbon atom; W represents O, S, NR$^7$, or C(=O), where R$^7$ represents hydrogen, —(C$_1$-C$_{12}$) alkyl, or substituted or unsubstituted aryl or aralkyl group; wherein where R$^7$ is substituted, the substituent is selected from hydroxy, halogen, linear or branched (C$_1$-C$_{10}$)alkyl (C$_1$-C$_6$)alkoxy; aryl or aralkyl group; m is the integer 1 or 2; n is an integer from 0-4; Ar represents substituted or unsubstituted divalent single or fused arylene group; wherein when Ar is substituted, the substituent is slected from linear or branched optionally halogenated (C$_1$-C$_6$) alkyl, optionally halogenated (C$_1$-C$_3$)alkoxy, halogen, nitro, acyl, amino, acylamino, thio or carboxylic or sulfonic acids and their amides; $R^4$ and $R^5$ are the same or different and represent hydrogen, hydroxy, alkoxy, halogen or substituted or unsubstituted groups selected from (C$_1$-C$_{12}$) alkyl, aralkyl or heteroaralkyl groups, wherein when $R^4$ or $R^5$ is substituted, the substituent is selected from halogen, hydroxy or (C$_1$-C$_6$) alkyl groups; $R^6$ is hydrogen or a substituted or unsubstituted group slected from (C$_1$-C$_{12}$) alkyl, cycloalkyl, aryl, aralkyl, heterocyclyl, heteroaryl or heteroaralkyl groups; wherein when the group $R^6$ is substituted, the subsitutent is slected from halogen, hydroxy, nitro, or groups (C$_1$-C$_6$)alkoxy, (C$_1$-C$_6$)alkyl, (C$_3$-C$_7$)cycloalkoxy, aryl, aralky, aralkoxy (C$_1$-C$_6$) arkyl, heterocyclyl, heteroaryl, heteroaralkyl, (C1-C6)acyl, C$_1$-C$_6$)acyloxy, hydroxy (C$_1$-C$_6$)alkyl, amino, (C$_1$-C$_6$)acylamino, arylamino, amino (C$_1$-C$_6$)alkyl, aryloxy, aralkoxy, (C$_1$-C$_6$)alkoxycarbonyl, (C$_1$-C$_6$)alkylamino, (C$_1$-C$_6$)alkoxyalky, (C$_1$-C$_6$)alkylthio, thio ($C_1$-$C_6$)alkyl groups, carboxylic acid or its amides or sulfonic acid or its amides; Y represents oxygen or $NR^8$, where $R^8$ represents hydrogen or substituted or unsubstituted groups selected from alkyl, aryl, hydroxyalkyl, aralkyl heterocyclyl, heteroaryl, or heteroaralkyl groups wherein when the group $R^8$ is stustituted, the subsituent is slected from hydroxy, halogen, linear or branched $C_1$-$C_{10}$)alkyl; ($C_1$-$C_6$) alkoxy; aryl or aralkyl group; $R^6$ and $R^8$ together may form a substituted or unsubstituted 5 or 6 membered cyclic structure containing carbon atoms, one or two nitrogen atoms and may optionally contain one or more heteroatoms selected from oxygen or sulfur; wherein when the group formed from $R^6$ and $R^5$ together is substituted, wherein when the group $R^6$ is subsituted, the substituent is selected from halogen, hydroxy, nitro, or groups ($C_1$-$C_6$)alkoxy, ($C_1$-$C_6$)alkyl, ($C_3$-$C_7$)cycloalkoxy, aryl, aralky, aralkoxy ($C_1$-$C_6$)alkyl, heterocyclyl, heteroaryl, heteroaralkyl, ($C_1$-$C_6$)acyl, ($C_1$-$C_6$)acyloxy, hydroxy ($C_1$-$C_6$)alkyl, amino, ($C_1$-$C_6$)alkylamino, ($C_1$-$C_6$)alkoxyalky, ($C_1$-$C_6$)alkylthio, thio ($C_1$-$C_6$)alkyl groups, carboxylic acid or its amides or sulfonic acid or its amides; Q represents O, S, SO, $SO_2$, or $NR^9$ wherein $R^9$ represents hydrogen, or substituted or unsubstituted group selected from ($C_1$-$C_{12}$)alkyl, cycloalkyl, aryl, hydroxyalkyl, aralkylheterocyclyl, heteroaryl, or heteroaralkyl groups wherein when $R^9$ is substituted, the substituent is selected from hydroxy, halogen, ($C_1$-$C_6$)alkyl or ($C_1$-$C_6$)alkoxy groups; and p is an integer of 0 or 1.

2. A compound according to claim 1, wherein Ar represents unsubstituted or substituted divalent phenylene, naphthylene.

3. A process for the preparation of compound of formula (I)

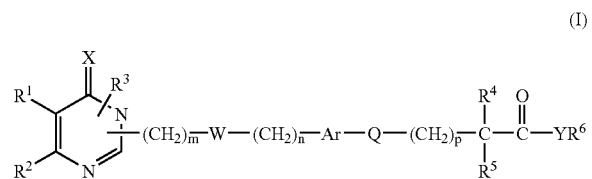

its tautomeric forms, its stereoisomers, its polymorphs, its pharmaceutically acceptable salts, or its pharmaceutically acceptable solvates, wherein X represents O or S; the groups $R^1$ and the group $R^3$ when attached to the carbon atom, are the same or different and represent hydrogen, halogen, hydroxy, nitro, cyano, formyl or substituted or unsubstituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, monoalkylamino, dialkylamino, arylamino, aralkylamino, aminoalkyl, alkoxycarbonyl, aryloxycarbonyl, aralkoxycarbonyl, alkoxyalkyl, aryloxyalkyl, aralkoxyalkyl, alkylthio, thioalkyl, alkoxycarbonylamino, aryloxycarbonylamino, aralkoxycarbonylamino, carboxylic acid or its amides, or sulfonic acid or its amides; $R^2$ represents cycloalkyl, aryl, aryloxy, aralkyl, aralkoxy, heterocyclyl, heteroaryl, heteroaralkyl, heteroaryloxy, heteroaralkoxy, arylamino, aralkylamino, aryloxycarbonyl, aralkoxycarbonyl, arloxyalkyl, aralkyoxyalkyl, aryloxycarbonylamino or aralkoxycarbonylamino; wherein when a group represented by $R^1$, $R^2$ or the group $R^3$ when attached to carbon atom is substituted, the sub stituent is selected from halogen, hydroxy, nitro, thio, alkyl, cycloalkyl, alkoxy, cycloalkoxy, aryl, aralkyl, aryloxy, aralkoxy, alkoxyalkyl, aryloxyalkyl, arakoxyalkyl, heterocyclyl, heteroaryl, heteroaralkyl, acyl, acyloxy, hydroxyalkyl, amino, acylamino, arylamino, aminoalkyl, alkoxycarbonyl, monoalkylamino, dialkyamino, alkylthio, carboxylic acid or its amides or sulfonic acid or its amides; $R^3$ when attached to nitrogen atom represents hydrogen, hydroxy, formyl or substituted or unsubstituted groups selected from alkyl, cycloalkyl, alkoxy, cycloalkoxy, aryl, aralkyl, heterocyclyl, heteroaryl, heteroaralkyl, hydroxyalkyl, amino, acylamino, monoalkylamino, dialkylamino, arylamino, aralkylamino, aminoalkyl, aryloxy, aralkoxy, heteroaryloxy, heteroaralkoxy, alkoxycarbonyl, aryloxycarbonyl, aralkoxycarbonyl, alkoxyalkyl, aryloxyalkyl, aralkoxyalkyl, carboxylic acid or its amides, or sulfonic acid or its amides; wherein the group $R^3$ when attached to nitrogen is substituted, the substituent is selected from halogen, hydroxy, acyl, acyloxy or amino groups; the linking group represented by —$(CH_2)_m$—W—$(CH_2)_n$— is attached either through nitrogen atom or through carbon atom; W represents O, S, $NR^7$, or —C(═O) where $R^7$ represents hydrogen, ($C_1$-$C_{12}$) alkyl, or substituted or unsubstituted aryl or aralkyl group; wherein where $R^2$ is substituted, the substituent is selected from hydroxy, halogen, linear or branched ($C_1$-$C_{10}$) alkyl ($C_1$-$C_6$)alkoxy; aryl or aralkyl group; m is the integer 1 or 2; and n is an integer from 0-4; Ar represents substituted or unsubstituted divalent single or fused arylene group; wherein when Ar is substituted, the substituent is selected from linear or branched optionally halogenated ($C_1$-$C_6$) alkyl, optionally halogenated ($C_1$-$C_3$)alkoxy, halogen, nitro, acyl, amino, acylamino, thio or carboxylic or sulfonic acids and their amides; $R^4$ and $R^5$ are the same or different and represent hydrogen, hydroxy, alkoxy, halogen or substituted or unsubstituted groups selected from ($C_1$-$C_{12}$) alkyl, aralkyl or heteroaralkyl groups; $R^6$ is hydrogen or a substituted or unsubstituted group selected from ($C_1$-$C_{12}$) alkyl, cycloalkyl, aryl, aralkyl, heterocyclyl, heteroaryl or heteroaralkyl groups; wherein when the group $R^5$ is substituted, the substituent is selected from halogen, hydroxy, nitro, or groups ($C_1$-$C_6$)alkoxy, ($C_1$-$C_6$)alkyl, ($C_3$-$C_7$)cycloalkoxy, aryl, araky, aralkoxy ($C_1$-$C_6$)alkyl, heterocyclyl, heteroaryl, heteroaralkyl, ($C_1$-$C_6$)acyl, ($C_1$-$C_6$)acyloxy, hydroxy ($C_1$-$C_6$)alkyl, amino, ($C_1$-$C_6$)acylamino, arylamino, amino ($C_1$-$C_6$) alkoxyalky, ($C_1$-$C_6$) alkylthio, thio ($C_1$-$C_6$)alkyl groups, carboxylic acid or its amides or sulfonic acid or its amides; Y represents oxygen or $NR^8$, where $R^8$ represents hydrogen or substituted or unsubstituted group selected from alkyl, aryl, hydroxyalkyl, aralkyl heterocyclyl, heteroaryl, or heteroaralkyl groups; wherein the group R8 is stubstituted, the substitutent is selected from hydroxy, halogen, linear or branched ($C_1$-$C_{10}$)alkyl; ($C_1$-$C_6$)alkoxy; aryl or aralkyl group; $R^6$ and $R^8$ together may form a substituted or unsubstituted 5 or 6 membered cyclic structure containing carbon atoms, one or two nitrogen atoms and may optionally contain one or more heteroatoms selected from oxygen, or sulfur; wherein when the group formed from $R^6$ and $R^8$ together is substituted, wherein when the group $R^6$ is substituted, the substituent is selected from halogen, hydroxy, nitro, or groups ($C_1$-$C_6$)alkoxy, ($C_1$-$C_6$)alkyl, ($C_3$-$C_7$)cycloalkoxy, aryl, aralky, aralkoxy ($C_1$-$C_6$)alkyl, heterocyclyl, heteroaryl, heteroaryl, heteroaralkyl, ($C_1$-$C_6$)acyl, ($C_1$-$C_6$) acyloxy, hydroxy ($C_1$-$C_6$)alkyl, amino, ($C_1$-$C_6$)acylamino, arylamino, amino ($C_1$-$C_6$)alkyl, aryloxy, aralkoxy, ($C_1$-$C_6$) alkoxycarbonyl, ($C_1$-$C_6$)alkylamino, ($C_1$-$C_6$)alkoxyalky, ($C_1$-$C_6$)alkylthio, thio ($C_1$-$C_6$)alkyl groups, carboxylic acid or its amides or sulfonic acid or its amides; Q represents O, S, SO, $SO_2$ or $NR^9$ wherein $R^9$ represents hydrogen, substituted or unsubstituted groups selected from ($C_1$-$C_{12}$)alkyl, cycloalkyl, aryl, hydroxyalkyl, aralkyl heterocyclyl, heteroaryl, or heteroaralkyl groups wherein $R^9$ is substituted, the substituent is selected from hydroxy, halogen, $(C_1-C_6)$ alkyl or $(C_1-C_6)$alkoxy groups; and p is an integer of 0 or 1, which comprises the steps of, a) reacting the compound of formula (IIIa)

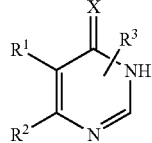
(IIIa)

where A and $R^1$, $R^2$, $R^3$ and X are as defined above with a compound of formula (IIIb)

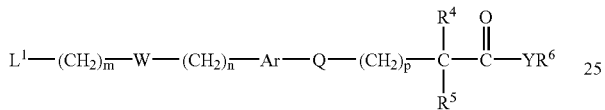
(IIIb)

where $L^1$ is a leaving group and all other symbols are as defined above or b) reacting a compound of formula (IIIc)

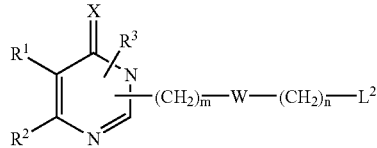
(IIIc)

where $L^2$ represents a halogen atom, W represents C=O and all other symbols are as defined above with a compound of formula (IIId)

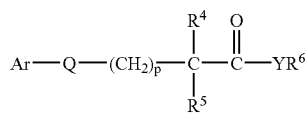
(IIId)

where all symbols are as defined above or c) reacting a compound of formula (IIIe)

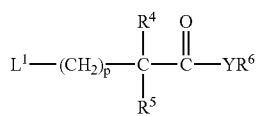
(IIIe)

where $L^1$ is a leaving group and all other symbols are as defined above with a compound of formula (IIIf)

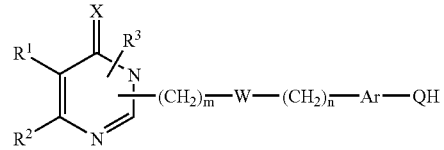
(IIIf)

where all symbols are as defined above or d) reacting the compound of formula (IIIg)

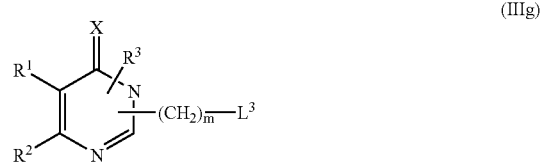
(IIIg)

where $L^3$ is a leaving group or $L^3$ represents COOH, or COCl, with compound of formula (IIIh)

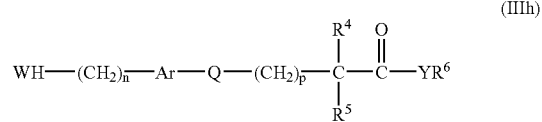
(IIIh)

where W represents $NR^7$ and all symbols are as defined above to produce a compound of formula (I) where W represents $NR^7$ and all other symbols are as defined above.

4. A compound which is selected from the group consisting of:

(±) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(+) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(−) Ethyl 2-[4-(2-ethyl-6-oxo-4-phenyl-1,6-dihydropyrimidin-1-ylmethyl(heptyl)carboxamido)phenyl sulfanyl]-3-methyl butanoate;

(±) Ethyl 2-{4-[2-(2-ethyl-6-oxo-4-phenyl-1,6-dihydropyrimidin-1-yl)ethyl(heptyl)carbamoyl]phenoxy}-2-methyl propanoate;

(+) Ethyl 2-{4-[2-(2-ethyl-6-oxo-4-phenyl-1,6-dihydropyrimidin-1-yl)ethyl(heptyl)carbamnoyl]phenoxy}-2-methyl propanoate;

(−) Ethyl 2-{4-[2-(2-ethyl-6-oxo-4-phenyl-1,6-dihydropyrimidin-1-yl)ethyl(heptyl)carbamoyl]phenoxy}-2-methyl propanoate;

(±) Ethyl 2-{4-[2-(2-ethyl-6-oxo-4-phenyl-1,6-dihydropyrimidin-1-yl)ethylcarbamoyl]phenoxy}-2-methyl propanoate;

(+) Ethyl 2-{4-[2-(2-ethyl-6-oxo-4-phenyl-1,6-dihydropyrimidin-1-yl)ethylcarbamoyl]phenoxy}-2-methyl propanoate;

(−) Ethyl 2-{4-[2-(2-ethyl-6-oxo-4-phenyl-1,6-dihydropyrimidin-1-yl)ethylcarbamoyl]phenoxy}-2-methyl propanoate;

(±) Ethyl 2-[4-(2-ethyl-6-oxo-4-phenyl-1,6-dihydropyrimidin-1-ylmethylcarboxamido)p-henoxy}-2-methyl propanoate;
(+) Ethyl 2-{4-(2-ethyl-6-oxo-4-phenyl-1,6-di-hydropyrimidin-1-ylmethylcarboxamido)phenoxy}-2-methyl propanoate;
(−) Ethyl 2-[4-(2-ethyl-6-oxo-4-phenyl-1,6-dihydropyrimidin-1-ylmethylcarboxa-mido)phenoxy}-2-methyl propanoate;
(±) Ethyl 2-[4-(2-Ethyl-6-oxo-4-phen-yl-1,6-dihydropyrimidin-1-ylmethyl(heptyl)carboxamido)phenoxy]-2-methyl propanoate;
(+) Ethyl 2-[4-(2-Ethyl-6-oxo-4-phenyl-1,6-dihydropyrimidin-1-ylmethyl(heptyl)carboxamido)phenoxy]-2-methyl propanoate;
(−) Ethyl 2-[4-(2-Ethyl-6-oxo-4-phenyl-1,6-dihydropyrimidin-1-ylmethyl(heptyl)carbo-xamido)phenoxy]-2-methyl propanoate;
(±) Ethyl 2-[4-(2-ethyl-6-oxo-4-ph-enyl-1,6-dihydropyrimidin-1-ylmethyl(heptyl)carboxamido)phenyl sulfanyl]-2-methyl propanoate;
(+) Ethyl 2-[4-(2-ethyl-6-oxo-4-phenyl-1,6-dihydropyrimidin-1-ylmethyl(heptyl)carboxamido)phenyl sulfanyl]-2-methyl propanoate;
(−) Ethyl 2-[4-(2-ethyl-6-oxo-4-phenyl-1,6-dihydropyrimidin-1-ylmethyl(heptyl)carboxamido)phenyl sulfanyl]-2-methyl propanoate;
(±) Ethyl 2-[4-(2-ethyl-6-oxo-4-phenyl-1,6-dihydropyrimidin-1-ylmethyl(heptyl)carboxamido)phenoxy]-2-methyl butanoate;
(+) Ethyl 2-[4-(2-ethyl-6-oxo-4-phenyl-1,6-dihydropyrimidin-1-ylmethyl(heptyl)carboxamido)phenoxy]-2-methyl butanoate;
(−) Ethyl 2-[4-(2-ethyl-6-oxo-4-phenyl-1,6-dihydropyrimidin-1-ylmethyl(heptyl)carboxamido)phenoxy]-2-methyl butanoate;
(±)Ethyl 2-[4-(2-ethyl-6-oxo-4-phenyl-1,6-dihydropyrimidin-1-ylmethyl(heptyl)carboxamido)phenyl sulfanyl]pentanoate;
(+) Ethyl 2-[4-(2-ethyl-6-oxo-4-phenyl-1,6-dihydropyrimidin-1-ylmethyl(heptyl)carboxamido)phenyl sulfanyl]pentanoate;
(−) Ethyl 2-[4-(2-ethyl-6-oxo-4-phenyl-1,6-dihydropyrimidin-1-ylmethyl(heptyl)carboxamido)phenyl sulfanyl]pentanoate;
(±) Ethyl 2-[4-(2-ethyl-6-oxo-4-phenyl-1,6-dihydropyrimidin-1-ylmethyl carboxamido)phenoxy]octanoate;
(+) Ethyl 2-[4-(2-ethyl-6-oxo-4-phenyl-1,6-dihydropyrimidin-1-ylmethyl carboxamido)phenoxy]octanoate;
(−) Ethyl 2-[4-(2-ethyl-6-oxo-4-phenyl-1,6-dihydropyrimidin-1-ylmethylcarboxamido)phenoxy]octanoate;
(±) Ethyl 2-[4-(2-ethyl-6-oxo-4-phenyl-1,6-dihydropyrimidin-1-ylmethyl(heptyl)carboxamido)phenyl sulfanyl]butanoate;
(+) Ethyl 2-[4-(2-ethyl-6-oxo-4-phenyl-1,6-dihydropyrimidin-1-ylmethyl(heptyl)carboxamido)phenyl sulfanyl]butanoate;
(−) Ethyl 2-[4-(2-ethyl-6-oxo-4-phenyl-1,6-dihydropyrimidin-1-ylmethyl(heptyl)carboxamido)phenyl sulfanyl]butanoate;
(±) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(+) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(−) Ethyl 2-[4-(2-Ethyl-6-oxo-4-phenyl-1,6-dihydropyrimidin-1-ylmethyl(heptyl)carboxamido)phenyl sulfanyl}-4-methyl pentanoate;
(±) Ethyl 2-[4-(2-ethyl-6-oxo-4-phenyl-1,6-dihydropyrimidin-1-ylmethyl(heptyl)carboxamido) phenoxy}pentanoate;
(+) Ethyl 2-[4-(2-ethyl-6-oxo-4-phenyl-1,6-dihydropyrimidin-1-ylmethyl(heptyl)carboxamido)phenoxypentanoate;
(−) Ethyl 2-[4-(2-ethyl-6-oxo-4-phenyl-1,6-dihydropyrimidin-1-ylmethyl(heptyl)carboxamido) phenoxy}pentanoate;
(±) Ethyl 2-[4-(2-ethyl-6-oxo-4-phenyl-1,6-dihydropyrimidin-1-ylmethylcarboxamido)phenyl sulfanyl}-3-methyl butanoate;
(+) Ethyl 2-[4-(2-ethyl-6-oxo-4-phenyl-1,6-dihydropyrimidin-1-ylmethylcarboxamido)phenyl sulfanyl}-3-methyl butanoate;
(−) Ethyl 2-[4-(2-ethyl-6-oxo-4-phenyl-1,6-dihydropyrimidin-1-ylmethylcarboxamido)phenyl sulfanyl}-3-methyl butanoate;
(±) Ethyl 2-{4-[2-(2-ethyl-6-oxo-4-phenyl-1,6-dihydropyrimidin-1-yl)ethoxy]phenoxy}-2-methyl propanoate;
(+) Ethyl 2-[4-[2-(2-ethyl-6-oxo-4-phenyl-1,6-dihydropyrimidin-1-yl)ethoxy]ph-enoxy}-2-methyl propanoate;
(−) Ethyl 2-{4-[2-(2-ethyl-6-oxo-4-phenyl-1,6-dihydropyrimidin-1-yl)ethoxy]phenoxy}-2-methyl propanoate;
(±) Ethyl 2-{4-[2-(2-ethyl-6-oxo-4-phenyl-1,6-dihydropyrimidin-1-yl)ethoxy]phenoxy}-2-methyl butanoate;
(+) Ethyl 2-{4-[2-(2-ethyl-6-oxo-4-phenyl-1,6-dihydropyrimidin-1-yl)ethoxy]phenoxy}-2-methyl butanoate;
(−) Ethyl 2-{4-[2-(2-ethyl-6-oxo-4-phenyl-1,6-dihydropyrimidin-1-yl)ethoxy]phenoxy}-2-methyl butanoate;
(±) Ethyl 2-{4-[2-(2-ethyl-6-oxo-4-phenyl-1,6-dihy-dropyrimidin-1-yl)ethoxy]phenoxy}pentanoate;
(+) Ethyl 2-{4-[2-(2-ethyl-6-oxo-4-phenyl-1,6-dihydropyrimidin-1-yl)ethoxy]phenoxy}pentanoate;
(−) Ethyl 2-{4-[2-(2-ethyl-6-oxo-4-phenyl-1,6-dihydropyrimidin-1-yl)ethoxy]phenoxy}pentanoate;
(±) Ethyl 2-{4-[2-(2-ethyl-6-oxo-4-phenyl-1,6-dihydropyrimidin-1-yl)ethyl amino]phenyl sulfanyl}-3-methyl butanoate;
(+) Ethyl 2-{4-[2-(2-ethyl-6-oxo-4-phenyl-1,6-dihydropyrimidin-1-yl) ethyl amino]phenyl sulfanyl}-3-methyl butanoate;
(−) Ethyl 2-(4-[2-(2-ethyl-6-oxo-4-phenyl-1,6-dihydropyrimidin-1-yl)ethyl amino]phenyl sulfanyl}-3-methyl butanoate;
(±) Ethyl 2-{4-[2-(2-ethyl-6-oxo-4-phenyl-1,6-dihydropyrimidin-1-yl)ethylamino]phenyl sulfanyl}butanoate;
(−) Ethyl 2-{4-[2-(2-ethyl-6-oxo-4-phenyl-1,6-dihydropyrimidin-1-yl)ethylamino]phenyl sulfanyl}butanoate;
(±) Ethyl 2-{4-[2-(2-ethyl-6-oxo-4-phenyl-1,6-dihydropyrimidin-1-yl)ethoxy]phenyl sulfanyl}butanoate;
(+) Ethyl 2-{4-[2-(2-ethyl-6-oxo-4-phenyl-1,6-dihydropyrimidin-1-yl)ethoxy]phenyl sulfanyl}butanoate;
(−) Ethyl 2-{4-[2-(2-ethyl-6-oxo-4-phenyl-1,6-dihydropyrimidin-1-yl)ethoxy]phenyl sulfanyl}butanoate;
(±) Ethyl 2-{4-[2-(2-ethyl-6-oxo-4-phenyl-1,6-dihy-dropyrimidin-1-yl)ethylamino]phenyl sulfanyl}-4-methyl pentanoate;

(+) Ethyl 2-{4-[2-(2-ethyl-6-oxo-4-phenyl-1,6-dihydropyrimidin-1-yl)ethylamino]phenyl sulfanyl}-4-methyl pentanoate;

(−) Ethyl 2-{4-[2-(2-ethyl-6-oxo-4-phenyl-1,6-dihydropyrimidin-1-yl)ethylamino]phenyl sulfanyl}-4-methyl pentanoate;

(±) Ethyl 2-{4-[2-(2-ethyl-6-oxo-4-phenyl-1,6-dihydropyrim-idin-1-yl)ethylsulfanyl]phenoxy}acetate;

(+) Ethyl 2-{4-[2-(2-ethyl-6-oxo-4-phenyl-1,6-dihydropyrimidin-1-yl)ethylsulfanyl]phenoxy}acetate;

(−) Ethyl 2-{4-[2-(2-ethyl-6-oxo-4-phenyl-1,6-dihydropyrim-idin-1-yl)ethylsulfanyl]phenoxy}acetate;

(±) Ethyl 2-{4-[2-(2-ethyl-6-oxo-4-phenyl-1,6-dihydropyrimidin-1-yl)ethoxy]anilino}propanoate;

(+) Ethyl 2-{4-[2-(2-ethyl-6-oxo-4-phenyl-1,6-dihydropyrimidin-1-yl)ethoxy]anilino}propanoate;

(−) Ethyl 2-{4-[2-(2-ethyl-6-oxo-4-phenyl-1,6-dihydropyrimidin-1-yl)ethoxy]anilino}propanoate;

(±) Ethyl 2-{4-[2-(2-ethyl-6-oxo-4-phenyl-1,6-dihydropyrimidin-1-yl)ethoxy]anilino}-2-methyl propanoate;

(+) Ethyl 2-{4-[2-(2-ethyl-6-oxo-4-phenyl-1,6-dihydropyrimidin-1-yl)ethoxy]anilino}-2-methyl propanoate;

(−) Ethyl 2-{4-[2-(2-ethyl-6-oxo-4-phenyl-1,6-dihydropyrimidin-1-yl)ethoxy]anilino}-2-methyl propanoate;

(±) Ethyl 2-{4-[2-(2-ethyl-6-oxo-4-phenyl-1,6-dih-ydro-pyrimidin-1-yl)ethoxy]anilino}pentanoate;

(+) Ethyl 2-{4-[2-(2-ethyl-6-oxo-4-phenyl-1,6-dihydropyrimidin-1-yl)ethoxy]anilino}-pentanoate;

(−) Ethyl 2-{4-[2-(2-ethyl-6-oxo-4-phenyl-1,6-dihydropyrimidin-1-yl)ethoxy]anilino}pentanoate;

(±) Ethyl 2-{4-[2-(2-ethyl-6-oxo-4-phe-nyl-1,6-dihydropyrimidin-1-yl)ethoxy](heptyl)anilino}propanoate;

(+) Ethyl 2-{4-[2-(2-ethyl-6-oxo-4-phenyl-1,6-dihydropyrimidin-1-yl)ethoxy](heptyl)-anilino}propanoate;

(−) Ethyl 2-{4-[2-(2-ethyl-6-oxo-4-phenyl-1,6-dihydropyrimidin-1-yl)ethoxy](heptyl)anilino}propanoate;

(±) 2-[4-(2-Ethyl-6-oxo-4-phenyl-1,6-dihydropyrimidin-1-ylmethyl(heptyl)carbo-xamido)phenyl sulfanyl]-3-methyl butanoic acid or its salts;

(+) 2-[4-(2-Ethyl-6-oxo-4-phenyl-1,6-dihydropyrimidin-1-ylmethyl(heptyl)carbo-xamido)phenyl sulfanyl]-3-methyl butanoic acid or its salts;

(−) 2-[4-(2-Ethyl-6-oxo-4-phenyl-1,6-dihydropyrimidin-1-ylmethyl(heptyl)carbo-xamido)phenyl sulfanyl]-3-methyl butanoic acid or its salts;

(±) 2-{4-[2-(2-Ethyl-6-oxo-4-phenyl-1,6-dihydropyrimidin-1-yl)ethylcarbamoyl]-phenoxy}-2-methyl propanoic acid or its salts;

(+) 2-{4-[2-(2-Ethyl-6-oxo-4-phenyl-1,6-dihydropyrimidin-1-yl)ethylcarbamoyl]phenoxy}-2-methyl propanoic acid or its salts;

(−) 2-{4-[2-(2-Ethyl-6-oxo-4-phenyl-1,6-dihy-dropyrimidin-1-yl)ethylcarbamoyl]phenoxy}-2-methyl propanoic acid or its salts;

(±) 2-{4-[2-(2-Ethyl-6-oxo-4-phenyl-1,6-dihydropyrimidin-1-yl)et-hyl(heptyl)carbamoyl]phenoxy}-2-methyl propanoic acid or its salts;

(+) 2-{4-[2-(2-Ethyl-6-oxo-4-phenyl-1,6-dihydropyrimidin-1-yl)ethyl(heptyl)carbamoyl]phenoxy}-2-methyl propanoic acid or its salts;

(−) 2-{4-[2-(2-Ethyl-6-oxo-4-phenyl-1,6-dihydropyrimidin-1-yl)ethyl(heptyl)carbamoyl]phenoxy}-2-methyl propanoic acid or its salts;

(±) 2-[4-(2-Ethyl-6-oxo-4-phenyl-1,6-dihydropyrimidin-1-ylmethylcarboxamido)phenoxy]-2-methyl propanoic acid or its salts;

(+) 2-[4-(2-Ethyl-6-oxo-4-ph-enyl-1,6-dihydropyrimidin-1-ylmethylcarboxamido)phenoxy]-2-methyl propanoic acid or its salts;

(−) 2-[4-(2-Ethyl-6-oxo-4-phenyl-1,6-dihydropyrimidin-1-ylmethylcarboxamido)phenoxy]-2-methyl propanoic acid or its salts;

(±) 2-[4-(2-Ethyl-6-oxo-4-phenyl-1,6-dihydropyrimidin-1-ylmethyl(heptyl)carboxamido)phenoxy]-2-methyl propanoic acid or its salts;

(+) 2-[4-(2-Ethyl-6-oxo-4-phenyl-1,6-dihydropyrimidin-1-ylmethyl(heptyl)carboxamido)phenoxy]-2-methyl propanoic acid or its salts;

(−) 2-[4-(2-Ethyl-6-oxo-4-phenyl-1,6-dihydropyrimidin-1-ylmethyl(heptyl)carboxamido)phenoxy]-2-methyl propanoic acid or its salts;

(±) 2-{4-[2-(2-Ethyl-6-oxo-4-phenyl-1,6-dihydropyrimidin-1-yl)ethoxy]phenoxy}-2-methyl propanoic acid or its salts;

(+) 2-{4-[2-(2-Ethyl-6-oxo-4-phenyl-1,6-dihydropyrimidin-1-yl)ethoxy]phenoxy}-2-methyl propanoic acid or its salts;

(−) 2-{4-[2-(2-Ethyl-6-oxo-4-phenyl-1,6-dihydropyrimidin-1-yl)etho-xy]phenoxy}-2-methyl propanoic acid or its salts;

(±) 2-{4-[2-(2-Eethyl-6-oxo-4-phenyl-1,6-dihydropyrimidin-1-yl)ethoxy]phenoxy-}pentanoic acid or its salts;

(+) 2-{4-[2-(2-Eethyl-6-oxo-4-phenyl-1,6-dihydropyrimidin-1-yl)ethoxy]phenoxy}pentanoic acid or its salts;

(−) 2-{4-[2-(2-Eethyl-6-oxo-4-phenyl-1,6-dihydropyrimidin-1-yl)ethoxy]phenoxy-1 pentanoic acid or its salts;

(±) 2-{4-[2-(2-Ethyl-6-oxo-4-phenyl-1,6-dihydropyrimidin-1-yl)ethoxy]phenoxy}-2-methyl butanoic acid or its salts;

(+) 2-{4-[2-(2-Ethyl-6-oxo-4-phenyl-1,6-dihydropyrimidin-1-yl)ethoxy]phenoxy}-2-methyl butanoic acid or its salts;

(−) 2-{4-[2-(2-Ethyl-6-oxo-4-phenyl-1,6-dihydropyrimidin-1-yl)ethoxy]phenoxy}-2-methyl butanoic acid or its salts;

(±) 2-[4-(2-Ethyl-6-oxo-4-phenyl-1,6-dihydropyrimidin-1-ylmethyl(heptyl)carboxamido)phenyl sulfanyl]-2-methyl propanoic acid or its salts (±) 2-{4-[2-(2-Ethyl-6-oxo-4-phenyl-1,6-dihydropyrimidin-1-ylmethyl(heptyl)carboxamido)phenyl sulfanyl]-2-methyl propanoic acid or its salts;

(+) 2-{4-[2-(2-Ethyl-6-oxo-4-phenyl-1,6-dihydropyrimidin-1-ylmethyl(heptyl)carboxamido)phenyl sulfanyl]-2-methyl propanoic acid or its salts;

(±) 2-{4-[2-(2-Ethyl-6-oxo-4-phenyl-1,6-dihydropyrimidin-1-yl)ethoxy]anilino}-propanoic acid or its salts;

(+) 2-{4-[2-(2-Ethyl-6-oxo-4-phenyl-1,6-dihydropyrimidin-1-yl)ethoxy]anilino}propanoic acid or its salts;

(−) 2-{4-[2-(2-Ethyl-6-oxo-4-phenyl-1,6-dihydropyrimidin-1-yl)ethoxy]anilino}-propanoic acid or its salts;

(±) 2-[4-(2-Ethyl-6-oxo-4-phenyl-1,6-dihydropyrimidin-1-ylmethyl(heptyl)carboxamido)phenoxy]-2-methyl butanoic acid or its salts;

(±) 2-[4-(2-Ethyl-6-oxo-4-phenyl-1,6-dihydropyrimidin-1-ylmethyl(heptyl)carboxamido)phenoxy]-2-methyl butanoic acid or its salts;

(−) 2-[4-(2-Ethyl-6-oxo-4-phenyl-1,6-dihydropyrimidin-1-ylmethyl(heptyl)carbo-xamido)phenoxy]-2-methyl butanoic acid or its salts;

(+) 2-[4-(2-Ethyl-6-oxo-4-phenyl-1,6-dihydropyrimidin-1-ylmethyl(heptyl)carboxamido)phenoxy]methyl pentanoic acid or its salts;

(+) 2-[4-(2-Ethyl-6-oxo-4-phenyl-1,6-dihydropyrimidin-1-ylmethyl(heptyl)carboxamido)phenoxy]methyl pentanoic acid or its salts;

(−) 2-[4-(2-Ethyl-6-oxo-4-phenyl-1,6-dihydropyrimidin-1-ylmethyl(heptyl)carboxamido)phenoxy]methyl pentanoic acid or its salts;

(±) 2-{4-[2-(2-Ethyl-6-oxo-4-phenyl-1,6-dihydropyrimidin-1-yl)ethoxy]anilino}-2-methyl propanoic acid or its salts;

(+) 2-{4-[2-(2-Ethyl-6-oxo-4-phenyl-1,6-dihydropyrimidin-1-yl)ethoxy]anilino}-2-methyl propanoic acid or its salts;

(−) 2-{4-[2-(2-Ethyl-6-oxo-4-phenyl-1,6-dihydropyrimidin-1-yl)ethoxy]anilino}-2-methyl propanoic acid or its salts;

(±) 2-{4-[2-(2-Ethyl-6-oxo-4-phenyl-1,6-dihydropyrimidin-1-yl)ethoxy]anilino}pentanoic acid or its salts;

(+) 2-{4-[2-(2-Ethyl-6-oxo-4-phenyl-1,6-dihydropyrimidin-1-yl)ethoxy]anilino}pentanoic acid or its salts;

(−) 2-{4-[2-(2-Ethyl-6-oxo-4-phenyl-1,6-dihydropyrimidin-1-yl)ethoxy]anilino}pentanoic acid or its salts;

(±) 2-[4-(2-Ethyl-6-oxo-4-phenyl-1,6-dihydropyrimidin-1-ylmethyl(heptyl)carboxamido)phenyl sulfanyl]pentanoic acid or its salts;

(+) 2-[4-(2-Ethyl-6-oxo-4-phenyl-1,6-dihydropyrimidin-1-ylmethyl(heptyl)carboxamido)phenyl sulfanyl]pentanoic acid or its salts;

(−) 2-[4-(2-Ethyl-6-oxo-4-phenyl-1,6-dihydropyrimidin-1-ylmethyl(heptyl)carboxamido)phenyl sulfanyl]pentanoic acid or its salts;

(±) 2-{4-[2-(2-Ethyl-6-oxo-4-phenyl-1,6-dihydropyrimidin-1-yl)ethylsulfanyl]phenoxy}acetic acid or its salts;

(+) 2-1 {4-[2-(2-Ethyl-6-oxo-4-phenyl-1,6-dihydropyrimidin-1-yl)ethylsulfanyl]phenoxy}acetic acid or its salts;

(−) 2-{4-[2-(2-Ethyl-6-oxo-4-phenyl-1,6-dihydropyrimidin-1-yl)ethylsulfanyl]phenoxy}acetic acid or its salts;

(±) 2-[4-(2-Ethyl-6-oxo-4-phenyl-1,6-dihydropyrimidin-1-ylmethyl(heptyl)carboxamido)phenyl sulfanyl]propanoic acid or its salts;

(+) 2-[4-(2-Ethyl-6-oxo-4-phenyl-1,6-dihydropyrimidin-1-ylmethyl(heptyl)carboxamido)phenyl sulfanyl]propanoic acid or its salts;

(−) 2-[4-(2-Ethyl-6-oxo-4-phenyl-1,6-dihydropyrimidin-1-ylmethyl(heptyl)carboxamido)phenyl sulfanyl]propanoic acid or its salts;

(±) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(+) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(−) 2-[4-(2-Ethyl-6-oxo-4-phenyl-1,6-dihydropyrimidin-1-ylmethyl(heptyl)carboxamido)phenyl sulfanyl]-4-methyl pentanoic acid or its salts;

(±) 2-{4-[2-(2-Ethyl-6-oxo-4-phenyl-1,6-dihydropyrimidin-1-yl)ethoxy]phenylsulfanyl}-2-methyl butanoic acid or its salts;

(+) 2-{4-[2-(2-Ethyl-6-oxo-4-phenyl-1,6-dihydropyrimidin-1-yl)ethoxy]phenylsulfanyl}-2-methyl butanoic acid or its salts;

(−) 2-{4-[2-(2-Ethyl-6-oxo-4-phenyl-1,6-dihydropyrimidin-1-yl)ethoxy]phenylsulfanyl}-2-methyl butanoic acid or its salts;

(±) 2-[4-(2-Ethyl-6-oxo-4-phenyl-1,6-dihydropyrimidin-1-ylmethylcarboxamido)phenyl sulfanyl]-3-methyl butanoic acid or its salts;

(+) 2-[4-(2-Ethyl-6-oxo-4-phenyl-1,6-dihydropyrimidin-1-ylmethylcarboxamido)phenyl sulfanyl]-3-methyl butanoic acid or its salts;

(−) 2-[4-(2-Ethyl-6-oxo-4-phenyl-1,6-dihydropyrimidin-1-ylmethylcarboxamido)phenyl sulfanyl]-3-methyl butanoic acid or its salts;

(±) 2-{4-[2-(2-Ethyl-6-oxo-4-phenyl-1,6-dihydropyrimidin-1-yl)ethylamino]phenyl sulfanylibutanoic acid or its salts;

(+) 2-{4-[2-(2-Ethyl-6-oxo-4-phenyl-1-1,6-dihydropyrimidin-1-yl)ethylamino]phenyl sulfanyl}butanoic acid or its salts;

(−) 2-{4-[2-(2-Ethyl-6-oxo-4-phenyl-1,6-dihydropyrimidin-1-yl)ethylamino]phenyl sulfanyl}butanoic acid or its salts;

(±) 2-{4-[2-(2-Ethyl-6-oxo-4-phenyl-1,6-dihydropyrimidin-1-yl)ethylamino]phenyl sulfanyl}-4-methyl pentanoic acid or its salts;

(+) 2-{4-[2-(2-Ethyl-6-oxo-4-phenyl-1,6-dihydropyrimidin-1-yl)ethylamino]phenyl sulfanyl}-4-methyl pentanoic acid or its salts;

(−) 2-{4-[2-(2-Ethyl-6-oxo-4-phenyl-1,6-dihydropyrimidin-1-yl)ethylamino]phenyl sulfanyl}-4-methyl pentanoic acid or its salts;

(±) 2-{4-[2-(2-Ethyl-6-oxo-4-phenyl-1,6-dihydropyrimidin-1-yl)ethylamino]phenyl sulfanyl}-3-methyl butanoic acid or its salts;

(+) 2-{4-[2-(2-Ethyl-6-oxo-4-phenyl-1,6-dihydropyrimidin-1-yl)ethylamino]phenyl sulfanyl}-3-methyl butanoic acid or its salts; or (−) 2-{4-[2-(2-Ethyl-6-oxo-4-phenyl-1,6-dihydropyrimidin-1-yl)ethylamino]phenyl sulfanyl}-3-methyl butanoic acid or its salts.

5. A salt of a compound which is selected from the group consisting of:

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6- oxo-4-phenyl-1,6-dihydropyrimidin-1-ylmethyl (heptyl)carboxamido)phenyl sulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenyl sulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenyl sulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl) ethylcarbamoyl]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylcarbamoyl]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metform, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethylcarbamoyl] phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1yl)ethyl (heptyl)carbamoyl]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1yl)ethyl (heptyl)carbamoyl]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1yl)ethyl (heptyl)carbamoyl]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethylcarboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethylcarboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, beuzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethylcarboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethyl (heptyl)carboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenoxy]-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethoxy]phenoxy}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; anlimonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy]phenoxy}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy]phenoxy}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Eethyl-6-oxo-4-phenyl-1,6-dihydropyrimidin-1-yl)ethoxy]phenoxy}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy]phenoxy}-2-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl- 6-oxo-4-phenyl-1,6-dihydropyrimidin-1-yl)ethoxy]
phenoxy}-2-methyl butanoic acid;

Li, Na, K, Ca, Mg, Fe, Cu, Zn, Mn; N,N'-diacetylethyl-
enediamine, betaine, caffeine, 2-diethylaminoethanol,
2-dimethylaminoethanol, N-ethylmorpholine, N-eth-
ylpiperidine, glucamine, glucosamine, hydrabamine,
isopropylamine, methylglucamine, morpholine, pipera-
zine, piperidine, procaine, purines, theobromine, tri-
ethylamine, trimethylamine, tripropylaamine,
tromethamine, diethanolamine, meglumine, ethylene-
diamine, N,N'-diphenylethylenediamine, N,N'-diben-
zylethylenediamine, N-benzyl phenylethylamine, cho-
line, choline hydroxide, dicyclohexylamine,
metformin, benzylamine, phenylethylamine, dialky-
lamine, trialkylamine, thiamine, aminopyrimidine,
aminopyridine, purine, spermidine; alkylphenylamine,
glycinol, phenyl glycinol; glycine, alanine, valine, leu-
cine, isoleucine, norleucine, tyrosine, cystine, cysteine,
methionine, proline, hydroxy proline, histidine, orni-
thine, lysine, arginine, serine, threonine, phenylalanine;
unnatural amino acids; D-isomers or substituted amino
acids; guanidine, substituted guanidine wherein the
substituent is selected from nitro, amino, alkyl, alkenyl,
or alkynyl; ammonium or substituted ammonium salts
and aluminum salts; sulphates, nitrates, phosphates,
perchlorates, borates, hydrohalides, acetates, tartrates,
maleates, citrates, succinates, palmoates, methane-
sulphonates, benzoates, salicylates, hydroxynaph-
thoates, benzenesulfonates, ascorbates, glycerophos-
phates, or ketoglutarates salts of (−) 2-{4-[2-(2-Ethyl-
6-oxo-4-phenyl-1,6-dihydropyrimidin-1-yl)ethoxy]
phenoxy}-2-methyl butanoic acid;

Li, Na, K, Ca, Mg, Fe, Cu, Zn, Mn; N,N'-diacetylethyl-
enediamine, betaine, caffeine, 2-diethylaminoethanol,
2-dimethylaminoethanol, N-ethylmorpholine, N-eth-
ylpiperidine, glucamine, glucosamine, hydrabamine,
isopropylamine, methylglucamine, morpholine, pipera-
zine, piperidine, procaine, purines, theobromine, tri-
ethylamine, trimethylamine, tripropylamine,
tromethamine, diethanolamine, meglumine, ethylene-
diamine, N,N'-diphenylethylenediamine, N,N'-diben-
zylethylenediami-ne, N-benzyl phenylethylamine, cho-
line, choline hydroxide, dicyclohexylamine,
metformin, benzylamine, phenylethylamine, dialky-
lamine, trialkylamine, thiamine, aminopyrimidine,
aminopyridine, purine, spermidine; alkylphenylamine,
glycinol, phenyl glycinol; glycine, alanine, valine, leu-
cine, isoleucine, norleucine, tyrosine, cystine, cysteine,
methionine, proline, hydroxy proline, histidine, orni-
thine, lysine, arginine, serine, threonine, phenylalanine;
unnatural amino acids; D-isomers or substituted amino
acids; guanidine, substituted guanidine wherein the
substituent is selected from nitro, amino, alkyl, alkenyl,
or alkynyl; ammonium or substituted ammonium salts
and aluminum salts; sulphates, nitrates, phosphates,
perchlorates, borates, hydrohalides, acetates, tartrates,
maleates, citrates, succinates, palmoates, methane-
sulphonates, benzoates, salicylates, hydroxynaph-
thoates, benzenesulfonates, ascorbates, glycerophos-
phates, or ketoglutarates salts of (±) 2-[4-(2-Ethyl-6-
oxo-4-phenyl-1,6-dihydropyrimidin-1-ylmethyl
(heptyl)carboxamido)phenyl sulfanyl]-2-methyl
propanoic acid;

Li, Na, K, Ca, Mg, Fe, Cu, Zn, Mn; N,N'-diacetylethyl-
enediamine, betaine, caffeine, 2-diethylaminoethanol,
2-dimethylaminoethanol, N-ethylmorpholine, N-eth-
ylpiperidine, glucamine, glucosamine, hydrabamine,
isopropylamine, methylglucamine, morpholine, pipera-
zine, piperidine, procaine, purines, theobromine, tri-
ethylamine, trimethylamine, tripropylamine,
tromethamine, diethanolamine, meglumine, ethylene-
diamine, N,N'-diphenylethylenediamine, N,N'-diben-
zylethylenediami-ne, N-benzyl phenylethylamine, cho-
line, choline hydroxide, dicyclohexylamine,
metformin, benzylamine, phenylethylamine, dialky-
lamine, trialkylamine, thiamine, aminopyrimidine,
aminopyridine, purine, spermidine; alkylphenylamine,
glycinol, phenyl glycinol; glycine, alanine, valine, leu-
cine, isoleucine, norleucine, tyrosine, cystine, cysteine,
methionine, proline, hydroxy proline, histidine, orni-
thine, lysine, arginine, serine, threonine, phenylalanine;
unnatural amino acids; D-isomers or substituted amino
acids; guanidine, substituted guanidine wherein the
substituent is selected from nitro, amino, alkyl, alkenyl,
or alkynyl; ammonium or substituted ammonium salts
and aluminum salts; sulphates, nitrates, phosphates,
perchlorates, borates, hydrohalides, acetates, tartrates,
maleates, citrates, succinates, palmoates, methane-
sulphonates, benzoates, salicylates, hydroxynaph-
thoates, benzenesulfonates, ascorbates, glycerophos-
phates, or ketoglutarates salts of (+) 2-[4-(2-Ethyl-6-
oxo-4-phenyl-1,6-dihydropyrimidin-1-ylmethyl
(heptyl)carboxamido)phenyl sulfanyl]-2-methyl
propanoic acid;

Li, Na, K, Ca, Mg, Fe, Cu, Zn, Mn; N,N'-diacetylethyl-
enediamine, betaine, caffeine, 2-diethylaminoethanol,
2-dimethylaminoethanol, N-ethylmorpholine, N-eth-
ylpiperidine, glucamine, glucosamine, hydrabamine,
isopropylamine, methylglucamine, morpholine, pipera-
zine, piperidine, procaine, purines, theobromine, tri-
ethylamine, trimethylamine, tripropylamine,
tromethamine, diethanolamine, meglumine, ethylene-
diamine, N,N'-diphenylethylenediamine, N,N'-diben-
zylethylenediami-ne, N-benzyl phenylethylamine, cho-
line, choline hydroxide, dicyclohexylamine,
metformin, benzylamine, phenylethylamine, dialky-
lamine, trialkylamine, thiamine, aminopyrimidine,
aminopyridine, purine, spermidine; alkylphenylamine,
glycinol, phenyl glycinol; glycine, alanine, valine, leu-
cine, isoleucine, norleucine, tyrosine, cystine, cysteine,
methionine, proline, hydroxy proline, histidine, orni-
thine, lysine, arginine, serine, threonine, phenylalanine;
unnatural amino acids; D-isomers or substituted amino
acids; guanidine, substituted guanidine wherein the
substituent is selected from nitro, amino, alkyl, alkenyl,
or alkynyl; ammonium or substituted ammonium salts
and aluminum salts; sulphates, nitrates, phosphates,
perchlorates, borates, hydrohalides, acetates, tartrates,
maleates, citrates, succinates, palmoates, methane-
sulphonates, benzoates, salicylates, hydroxynaph-
thoates, benzenesulfonates, ascorbates, glycerophos-
phates, or ketoglutarates salts of (−) 2-[4-(2-Ethyl-6-
oxo-4-phenyl-1,6-dihydropyrimidin-1-ylmethyl
(heptyl)carboxamido)phenyl sulfanyl]-2-methyl
propanoic acid;

Li, Na, K, Ca, Mg, Fe, Cu, Zn, Mn; N,N'-diacetylethyl-
enediamine, betaine, caffeine, 2-diethylaminoethanol,
2-dimethylaminoethanol, N-ethylmorpholine, N-eth-
ylpiperidine, glucamine, glucosamine, hydrabamine,
isopropylamine, methylglucamine, morpholine, pipera-
zine, piperidine, procaine, purines, theobromine, tri-
ethylamine, trimethylamine, tripropylamine,
tromethamine, diethanolamine, meglumine, ethylene-
diamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (.+−.) 2-{4-[2-(2-Ethyl-6-oxo-4-phenyl-1,6-dihydropyrimidin-1-yl)ethoxy]anilino}pentanoic acid; acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaplithoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy]anilino}propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethoxy]anilino}propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenoxy]-2-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, -histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenoxy]-2-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenoxy]-2-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethyl (heptyl)carboxamido)phenoxy]methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenoxy]methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylaamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenoxy]methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylnorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy]anilino}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy]anilino}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethoxy]anilino}-2-methyl propanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, sen, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy]anilino}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy]anilino}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethoxy]anilino}pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethyl (heptyl)carboxamido)phenylsulfanyl]pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenylsulfanyl]pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenylsulfanyl]pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylsulfanyl]phenoxy}acetic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, -.trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylsulfanyl]phenoxy}acetic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl) ethylsulfanyl}phenoxy}acetic acid;

Li, Na, K, Ca, Mg, Fe, Cu, Zn, Mn; N,N'-diacetylethylenediamine, -betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, -meglumine, ethylenediamine, N,N'-diphenylethylenediamine-, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethyl (heptyl)carboxamido)phenyl sulfanyl]butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine;

unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenyl sulfanyl]butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6-oxo-4-phenyl-1,6-dihydropyrimidin-1-ylmethyl (heptyl)carboxamido)phenyl sulfanyl]butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethyl (heptyl)carboxamido)phenyl sulfanyl]-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethyl (heptyl)carboxamido)phenyl sulfanyl]-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-[4-(2-Ethyl-6- oxo-4-phenyl-1,6-dihydropyrimidin-1-ylmethyl (heptyl)carboxamido)phenyl sulfanyl]-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl)ethoxy] phenylsulfanyl}-2-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylaamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl)ethoxy] phenylsulfanyl}-2-methyl butanoic acid;

Li, Na, K, Ca, Mg, Fe, Cu, Zn, Mn; N,N'-diacetylethylenedi-amine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl)ethoxy] phenylsulfanyl}-2-methyl butanoic acid; caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-[4-(2-Ethyl-6-oxo-4-phenyl-1,6-dihydropyrimidin-1-ylmethylcarboxamido) phenylsulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylaamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-[4-(2-Ethyl-6-oxo-4-phenyl-1,6-dihydropyrimidin-1-ylmethylcarboxamido)phenyl sulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−).2-[4-(2-Ethyl-6-oxo-4-phenyl-1,6-dihydropyrimidin-1-ylmethylcarboxamido)phenyl sulfanyl]-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihydropyrimidin-1-yl) ethylamino]phenyl sulfanyl}butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, -meglumine, ethylenediamine, N,N'-diphenylethylenediamine-, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylamino]phenyl sulfanyl}butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl) ethylamino]phenyl sulfanyl}butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediamine, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{4-[2-(2-Ethyl-6-oxo-4-phenyl-1,6-dihyd opyrimidin-1-yl) ethylamino]phenylsulfanyl}-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylamino]phenylsulfanyl}-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl) ethylaminol]phenylsulfany}-4-methyl pentanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (±) 2-{[2-(2-Ethyl-6-oxo-4-phenyl-1,6-dihydropyrimidin-1-yl)ethylamino] phenylsulfanyl}-3-methyl butanoic acid;

Li, Na, K, Ca, Mg, Fe, Cu, Zn, Mn; N,N'-diacetylethylenediamine, betaine, caffeine, 2-diethylaminoethanol, 2-dimethylaminoethanol, N-ethylmorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (+) 2-{4-[2-(2-Ethyl-6-oxo-4-phenyl-1,6-dihydropyrimidin-1-yl) ethylamino]phenylsulfanyl}-3-methyl butanoic acid; and Li, Na, K, Ca, Mg, Fe, Cu, Zn, Mn; N,N'-diacetylethylenediamine, betaine, caffeine, 2-diethylaminoethanol, 2-dimethylaminoethanol, N-ethylnorpholine, N-ethylpiperidine, glucamine, glucosamine, hydrabamine, isopropylamine, methylglucamine, morpholine, piperazine, piperidine, procaine, purines, theobromine, triethylamine, trimethylamine, tripropylamine, tromethamine, diethanolamine, meglumine, ethylenediamine, N,N'-diphenylethylenediamine, N,N'-dibenzylethylenediami-ne, N-benzyl phenylethylamine, choline, choline hydroxide, dicyclohexylamine, metformin, benzylamine, phenylethylamine, dialkylamine, trialkylamine, thiamine, aminopyrimidine, aminopyridine, purine, spermidine; alkylphenylamine, glycinol, phenyl glycinol; glycine, alanine, valine, leucine, isoleucine, norleucine, tyrosine, cystine, cysteine, methionine, proline, hydroxy proline, histidine, ornithine, lysine, arginine, serine, threonine, phenylalanine; unnatural amino acids; D-isomers or substituted amino acids; guanidine, substituted guanidine wherein the substituent is selected from nitro, amino, alkyl, alkenyl, or alkynyl; ammonium or substituted ammonium salts and aluminum salts; sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, or ketoglutarates salts of (−) 2-{4-[2-(2-Ethyl-6-oxo-4-phenyl-1,6-dihydropyrimidin-1-yl) ethylamino]phenylsulfany}-3-methyl butanoic acid.

6. A pharmaceutical composition which comprises a compound of formula (I)

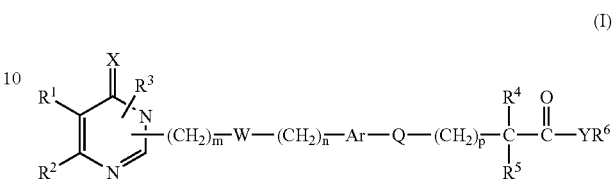

as defined in claim 1 and a pharmaceutically acceptable carrier, diluent, excipient or solvate.

7. A composition which comprises a compound of formula (I) as defined in claim 1, and an HMG CoA reductase inhibitor, ezetimibe, orlistat, fibrate, nicotinic acid, cholestyramine, cholestipol, probucol or a mixture thereof and a pharmaceutically acceptable carrier, diluent, excipient or solvate.

8. A pharmaceutical composition as claimed in claim 6 in the form of a tablet, capsule, powder, syrup, solution or suspension.

9. A pharmaceutical composition which comprises a compound as claimed in claim 4 and a pharmaceutically acceptable carrier, diluent, excipient or solvate.

10. A pharmaceutical composition which comprises a compound as claimed in claim 5 and a pharmaceutically acceptable carrier, diluent, excipient or solvate.

11. A compositon which comprises a compound as claimed in claim 4 and an HMG CoA reductase inhibitor, ezetimibe, orlistat, fibrate, nicotinic acid, cholestyramine, cholestipol, probucol or a mixture thereof and a pharmaceutically acceptable carrier, diluent, excipient or solvate.

12. A pharmaceutical composition as claimed in claim 7 in the form of a tablet, capsule, powder, syrup solution or suspension.

13. A pharmaceutical composition as claimed in claim 9 in the form of a tablet, capsule, powder, syrup, solution or suspension.

14. A pharmaceutical composition as claimed in claim 10 in the form of a tablet, capsule, powder, syrup, solution or suspension.

15. A pharmaceutical composition as claimed in claim 11 in the form of a tablet, capsule, powder, syrup, solution or suspension.

* * * * *